(12) United States Patent
Onuma

(10) Patent No.: US 10,640,483 B2
(45) Date of Patent: May 5, 2020

(54) SALTS OF INDAZOLE DERIVATIVE AND CRYSTALS THEREOF

(71) Applicant: Eisai R&D Management Co., Ltd., Tokyo (JP)

(72) Inventor: Keiko Onuma, Tsukuba (JP)

(73) Assignee: EISAI R&D MANAGEMENT CO., LTD., Tokyo (JP)

( * ) Notice: Subject to any disclaimer, the term of this patent is extended or adjusted under 35 U.S.C. 154(b) by 0 days.

(21) Appl. No.: 16/096,136

(22) PCT Filed: Nov. 27, 2017

(86) PCT No.: PCT/JP2017/042335
§ 371 (c)(1),
(2) Date: Oct. 24, 2018

(87) PCT Pub. No.: WO2018/097273
PCT Pub. Date: May 31, 2018

(65) Prior Publication Data
US 2019/0144419 A1    May 16, 2019

(30) Foreign Application Priority Data
Nov. 28, 2016   (JP) ................. 2016-229635

(51) Int. Cl.
C07D 401/06 (2006.01)
A61P 35/00 (2006.01)

(52) U.S. Cl.
CPC ............ C07D 401/06 (2013.01); A61P 35/00 (2018.01); *C07B 2200/13* (2013.01)

(58) Field of Classification Search
CPC .... C07D 401/06; A61P 35/00; C07B 2200/13
See application file for complete search history.

(56) References Cited

U.S. PATENT DOCUMENTS

| | | | |
|---|---|---|---|
| 5,552,412 A | 9/1996 | Cameron et al. | |
| 8,063,249 B1 | 11/2011 | Kushner et al. | |
| 8,299,112 B2 | 10/2012 | Smith et al. | |
| 8,455,534 B2 | 6/2013 | Smith et al. | |
| 8,785,501 B2 | 7/2014 | Witt-Enderby et al. | |
| 9,399,646 B2 | 7/2016 | Smith et al. | |
| 9,796,683 B2 | 10/2017 | Bock et al. | |
| 2002/0103229 A1 | 8/2002 | Bhagwat et al. | |
| 2013/0231333 A1 | 9/2013 | Smith et al. | |
| 2013/0336962 A1 | 12/2013 | Anderson et al. | |
| 2014/0199236 A1 | 7/2014 | Chen et al. | |
| 2015/0105403 A1 | 4/2015 | Smith et al. | |
| 2016/0347717 A1 | 12/2016 | Bock et al. | |
| 2018/0127378 A1* | 5/2018 | Bock .................... | C07D 231/56 |
| 2018/0141913 A1 | 5/2018 | Bock et al. | |

FOREIGN PATENT DOCUMENTS

| | | |
|---|---|---|
| EA | 000815 B1 | 4/2000 |
| EP | 0 802 184 A1 | 10/1997 |
| GB | 2483736 A | 3/2012 |
| JP | 2013-513639 A | 4/2013 |
| RU | 2130454 C1 | 5/1999 |
| WO | 9010638 A1 | 9/1990 |
| WO | 2007058626 A1 | 5/2007 |
| WO | 2009120999 A2 | 10/2009 |
| WO | 2011068211 A1 | 6/2011 |
| WO | 2011073117 A1 | 6/2011 |
| WO | 2011129837 A1 | 10/2011 |
| WO | 2012037410 A2 | 3/2012 |
| WO | 2012037411 A2 | 3/2012 |
| WO | 2013056178 A2 | 4/2013 |
| WO | 2013142266 A1 | 9/2013 |
| WO | 2014205136 A1 | 12/2014 |
| WO | 2014205138 A1 | 12/2014 |
| WO | 2015000868 A1 | 1/2015 |
| WO | 2015136016 A2 | 9/2015 |
| WO | 2016055982 A1 | 4/2016 |

(Continued)

OTHER PUBLICATIONS

Office Action dated Jul. 9, 2019 by the Brazilian Patent and Trademark Office in corresponding Brazilian Patent Application No. BR 11 2019 008489-4 and an English Translation of the Office Action. (21 pages).
International Search Report and Written Opinion for PCT/US16/34764, dated Aug. 30, 2016.
Search History accompanying International Search Report for PCT/US2016/34764 dated Aug. 1, 2016.
PubChem, Compound Summary for CID 69281185, dated Dec. 1, 2012.
PubChem, Compound Summary for CID 89780731, dated Feb. 13, 2015.
International Search Report and Written Opinion for PCT/US2016/34774, dated Sep. 7, 2016.

(Continued)

*Primary Examiner* — Timothy R Rozof
(74) *Attorney, Agent, or Firm* — Buchanan Ingersoll & Rooney PC

(57) ABSTRACT

The present invention provides salts of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide represented by the formula I and acids, and crystals thereof, possessing a potential to be used as drug substance in pharmaceuticals.

[Chem. 1]

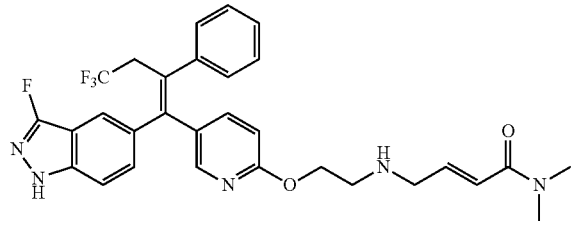

formula I

25 Claims, 22 Drawing Sheets
Specification includes a Sequence Listing.

(56) References Cited

FOREIGN PATENT DOCUMENTS

| WO | 2016097071 A1 | 6/2016 |
|---|---|---|
| WO | 2016196346 A1 | 12/2016 |
| WO | 2018/097273 A1 | 5/2018 |

OTHER PUBLICATIONS

Search History accompanying International Search Report for PCT/US16/34774 dated Jul. 16, 2016.
International Search Report and Written Opinion for PCT/US2016/034782, dated Aug. 23, 2016.
Search History accompanying International Search Report for PCT/US2016/034782 dated Jul. 25, 2016.
Non-Final Office action in U.S. Appl. No. 15/167,373, dated Dec. 23, 2016.
Response to Non-Final Office action in U.S. Appl. No. 15/167,373, filed Mar. 22, 2017.
Notice of Allowance in U.S. Appl. No. 15/167,373, dated Jun. 21, 2017.
Mattras, et al., "Identification by MALDI-TOF Mass Spectrometry of 17α-Bromoacetamidopropylestradiol Covalent Attachment Sites on Estrogen Receptor α", Biochemistry, 2002, pp. 15713-15727, vol. 41, No. 52.
Reese, et al., "Mutagenesis of Cysteines in the Hormone Binding Domain of the Human Estrogen Receptor", The Journal of Biological Chemistry, Jun. 1991, pp. 10880-10887, vol. 266, No. 17.
Fisher, et al., "Endometrial Cancer in Tamoxifen-Treated Breast Cancer Patients: Findings From the National Surgical Adjuvant Breast and Bowel Project (NSABP) B-14", Journal of the National Cancer Institute, Apr. 1994, pp. 527-537, vol. 86, No. 7.
Li, et al., "Endocrine-Therapy-Resistant ESR1 Variants Revealed by Genomic Characterization of Breast-Cancer Derived Xenografts", Cell Reports, Sep. 2013, pp. 1116-1130, vol. 4.
Jeselsohn, et al., "Emergence of Constitutively Active Estrogen Receptor-α Mutations in Pretreated Advanced Estrogen Receptor-Positive Breast Cancer", Clin Cancer Res, Apr. 2014, pp. 1757-1767, vol. 20, No. 7.
Merenbakh-Lamin, et al., "D538G Mutation in Estrogen Receptor-α: A Novel Mechanism for Acquired Endocrine Resistance in Breast Cancer", Cancer Res, Dec. 2013, pp. 6856-6864, vol. 72, No. 23.
Osborne, et al., "Role of the Estrogen Receptor Coactivator AIB1 (SRC-3) and HER-2/neu in Tamoxifen Resistance in Breast Cancer", Journal of the National Cancer Institute, Mar. 2003, pp. 353-361, vol. 95, No. 5.
Osborne, et al., "Mechanisms of Endocrine Resistance in Breast Cancer", Annu. Rev. Med., 2011, pp. 233-247, vol. 62.
Segal, et al., "Estrogen Receptor Mutations in Breast Cancer—New Focus on an Old Target", Clin Cancer Res, Apr. 2014, pp. 1724-1726, vol. 20, No. 7.
Shou, et al., "Mechanisms of Tamoxifen Resistance: Increased Estrogen Receptor-HER2/neu Cross-Talk in ER/HER2-Positive Breast Cancer", Journal of the National Cancer Institute, Jun. 2004, pp. 926-935, vol. 96, No. 12.
Toy, et al., "ESR1 ligand-binding domain mutations in hormone-resistant breast cancer", Nature Genetics, Dec. 2013, pp. 1439-1445, vol. 45, No. 12.
Van Leeuwen, et al., "Risk of endometrial cancer after tamoxifen treatment of breast cancer", The Lancet, Feb. 1994, pp. 448-452, vol. 343.
Yu, et al., "Ex vivo culture of circulating breast tumor cells for individualized testing of drug susceptibility", Science Mag, Jul. 2014, pp. 216-220, vol. 345, issue 6193.
Robinson, et al., "Activating ESR1 mutations in hormone-resistant metastatic breast cancer", Nature Genetics, Dec. 2013, pp. 1446-1451, vol. 45, No. 12.
Lai, et al., "Identification of GDC-0810 (ARN-810), an Orally Bioavailable Selective Estrogen Receptor Degrader (SERD) that Demonstrates Robust Activity in Tamoxifen-Resistant Breast Cancer Xenografts", Journal of Medicinal Chemistry, 2015, pp. 4888-4904, vol. 58.

Keely, et al., "Design, Synthesis and Biochemical Evaluation of Estrogen Receptor Ligand Conjugates as Tumour Targeting Agents", Letters in Drug Design & Discovery, 2012, pp. 295-304, vol. 9, No. 3.
McDonnell, "The Molecular Pharmacology of SERMs", TEM, 1999, pp. 301-311, vol. 10, No. 8.
Wang, et al., "A second binding site for hydroxytamoxifen within the coactivator-binding groove of estrogen receptor 3", PNAS, pp. 9908-9911, Jun. 2006, vol. 103, No. 26.
Coser, et al., "Global analysis of ligand sensitivity of estrogen inducible and suppressible genes in MCF7BUS breast cancer cells by DNA microarray", PNAS, pp. 9908-9911, Jun. 2006, vol. 103, No. 26.
The Cancer Genome Atlas Research Network, "Integrated genomic characterization of endometrial cancinoma", Nature, 2013, pp. 1-5, vol. 000.
"International Search Report and Written Opinion", International Search Report and Written Opinion for PCT/US2017/063047 dated Feb. 28, 2018.
Notice of Allowance of JP Patent Application No. P2017-226501, date of dispatch May 22, 2018.
Office Action for JP Patent Application No. P2017-226501, date of dispatch May 8, 2018.
Official Notification for JP Patent Application No. P2017-226501, date of dispatch May 10, 2018.
Official Notification for JP Patent Application No. P2017-226501, date of dispatch Apr. 16, 2018.
International Search Report and Written Opinion for PCT/JP2017/042335 filed Nov. 27, 2017, dated Feb. 20, 2018.
Harlow, K.W., et al., Identification of Cysteine 530 as the Covalent Attachment Site of an Affinity-labeling Estrogen (Ketononestrol Aziridine) and Antiestrogen(Tamoxifen Aziridine) in the Human Estrogen Receptor, The Journal of Biological Chemistry, 1989, 17476-17485, vol. 264, No. 29, Issue of Oct. 15, The American Society for Biochemistry and Molecular Biology, Inc.
International Search Report (PCT/ISA/210) and Written Opinion (PCT/ISA/237) dated Feb. 22, 2018, by the European Patent Office as the International Searching Authority for International Application No. PCT/US2017/062978.
Kandoth et al., "Integrated genomic characterization of endometrial carcinoma", Nature, May 2013, pp. 67-73, 497 (7447).
Notice of Allowance and Fees Due in U.S. Appl. No. 15/821,367, dated Sep. 18, 2018.
Notice of Allowance and Fees Due in U.S. Appl. No. 15/821,367, dated Sep. 26, 2018.
Notice of Allowance and Fees Due in U.S. Appl. No. 15/821,367, dated Jan. 17, 2019.
Abandonment in U.S. Appl. No. 15/821,367, dated May 6, 2019.
FDA guidance, "In Vitro Metabolism- and Transporter-Mediated Drug-Drug Interaction Studies Guidance for Industry", Draft Guidance, Oct. 24, 2017, p. 24, lines 854-858.
Grimm et al., "The conduct of in vitro studies to address time-dependent inhibition of drug-metabolizing enzymes: a perspective of the Pharmaceutical Research and Manufacturers of America," Drug Metab Dispos.37, pp. 1355-1370, 2009.
Wick, et al., "Abstract P3-03-04: Establishment and characterization of ESR1-mutant breast cancer PDX model", Cancer Res 2016, 76 (4 Suppl), Abstract nr P3-03-04.
Wick, et al., "Abstract P3-04-26: Establishment and characterization of ST941/C; an ESR 1-mutant ER+ breast cancer cell line and xenograft from a patient with acquired resistance to endocrine therapy", AACR, Cancer Res 2017, 77.
International Preliminary Report on Patenttability (Form PCT/IB/373) dated May 28, 2019, by the International Bureau of WIPO, and the Written Opinion of the International Searching Authority (Form PCT/ISA/237) dated Feb. 20, 2018, by the Japan Patent Office for International Application No. PCT/JP2017/042335. (7 pages).
Notification of Transmittal of the International Search Report (Form PCT/ISA/220) and the Written Opinion of the International Searching Authority (Form PCT/ISA/237) dated Aug. 6, 2019, by the Japan Patent Office for International Application No. PCT/JP2019/019947. (10 pages).

(56) References Cited

OTHER PUBLICATIONS

Office Action dated Oct. 18, 2019, by the Russian Patent Office for the Russian Patent Application No. 2017146408/04(079322) and an English Translation of the Office Action. (12 pages).
Search Report dated Oct. 15, 2019, by the Russian Patent Office for the Russian Patent Application No. 2017146408/04(079322) and an English Translation of the Search Report. (4 pages).
Copending U.S. Appl. No. 16/349,479, filed May 13, 2019.
Non-Final Office Action in U.S. Appl. No. 15/713,107, dated Dec. 21, 2018.
Final Office Action in U.S. Appl. No. 15/716,107, dated Jul. 23, 2019.
Office Action dated Oct. 18, 2019, by the Russian Patent Office in corresponding Russian Patent Application No. 2017146408/04(079322) and an English Translation of the Office Action. (16 pages).
European Patent Application No. 17873875.3, Response Submission dated Dec. 17, 2019. (30 pages).

\* cited by examiner

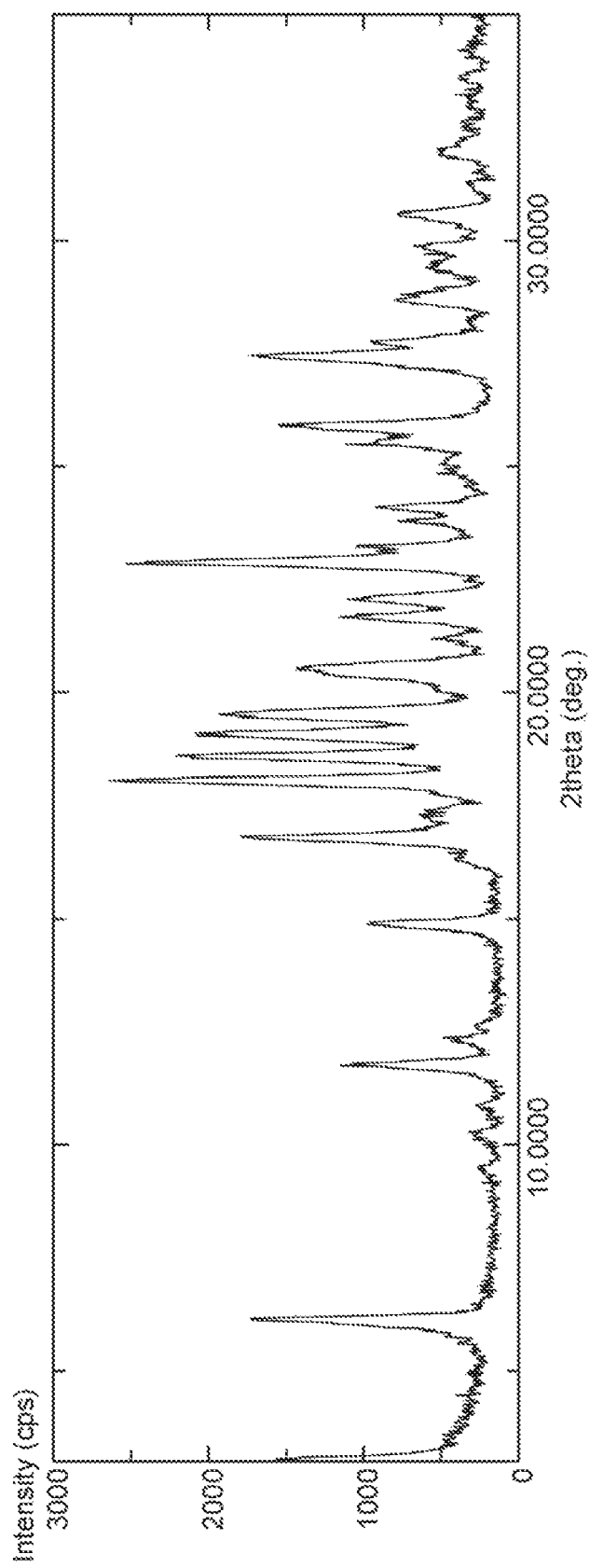
[Fig. 1]

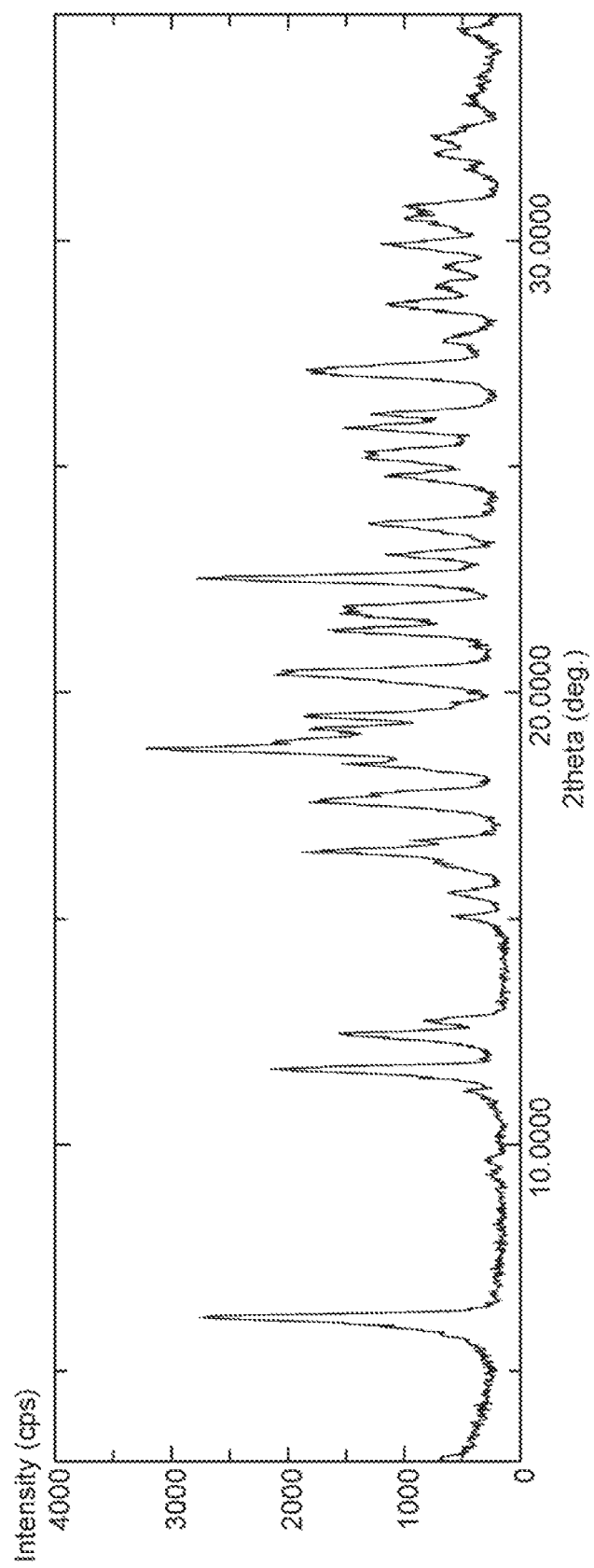

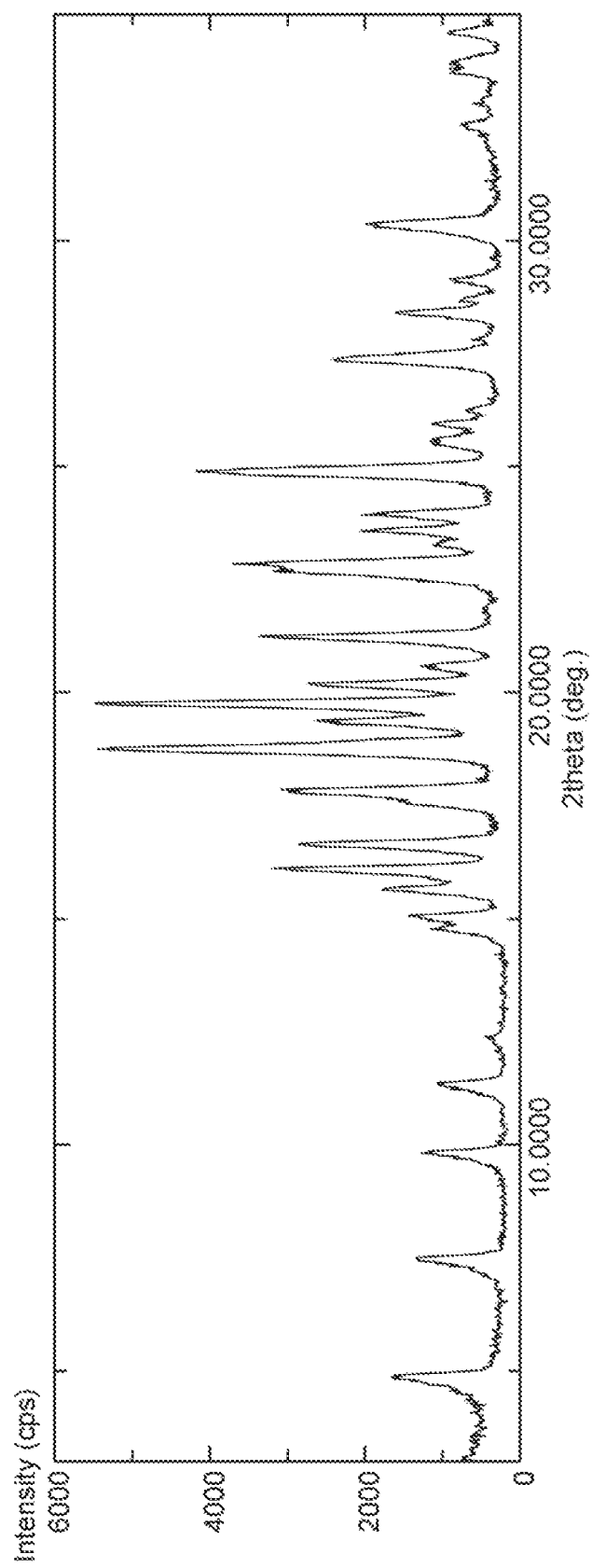
[Fig. 3]

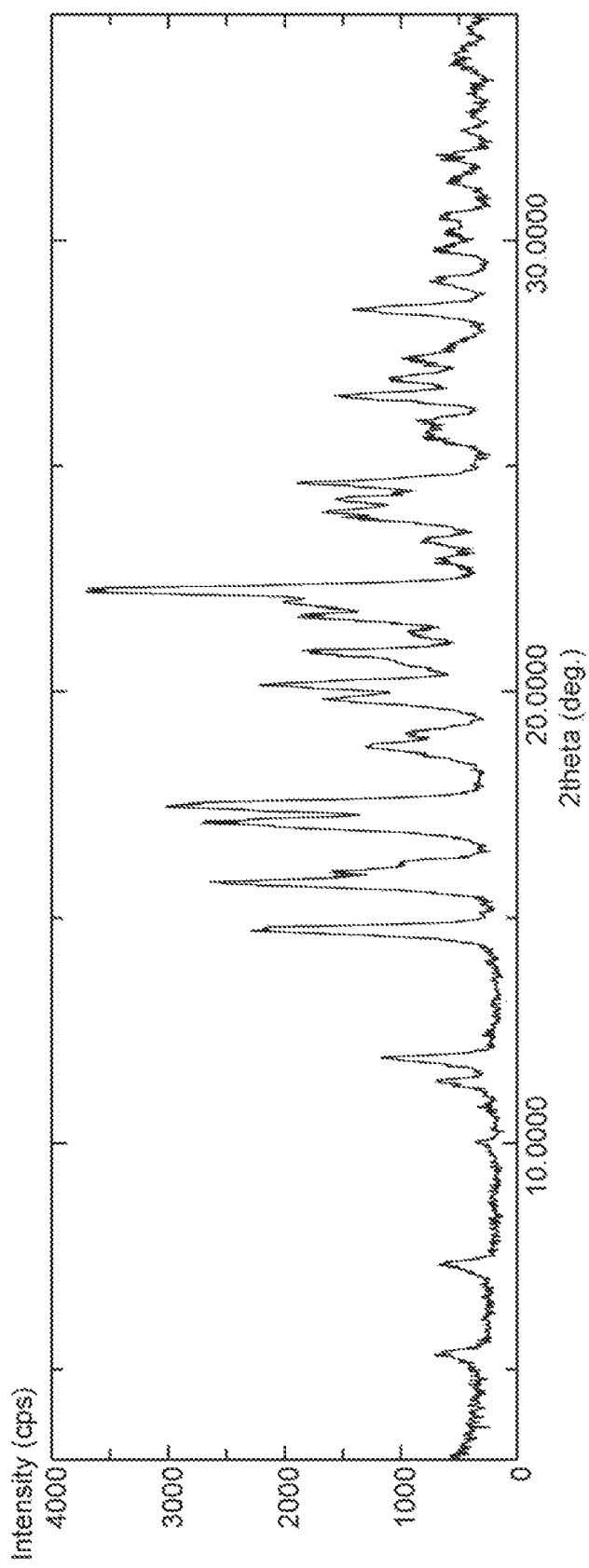
[Fig. 4]

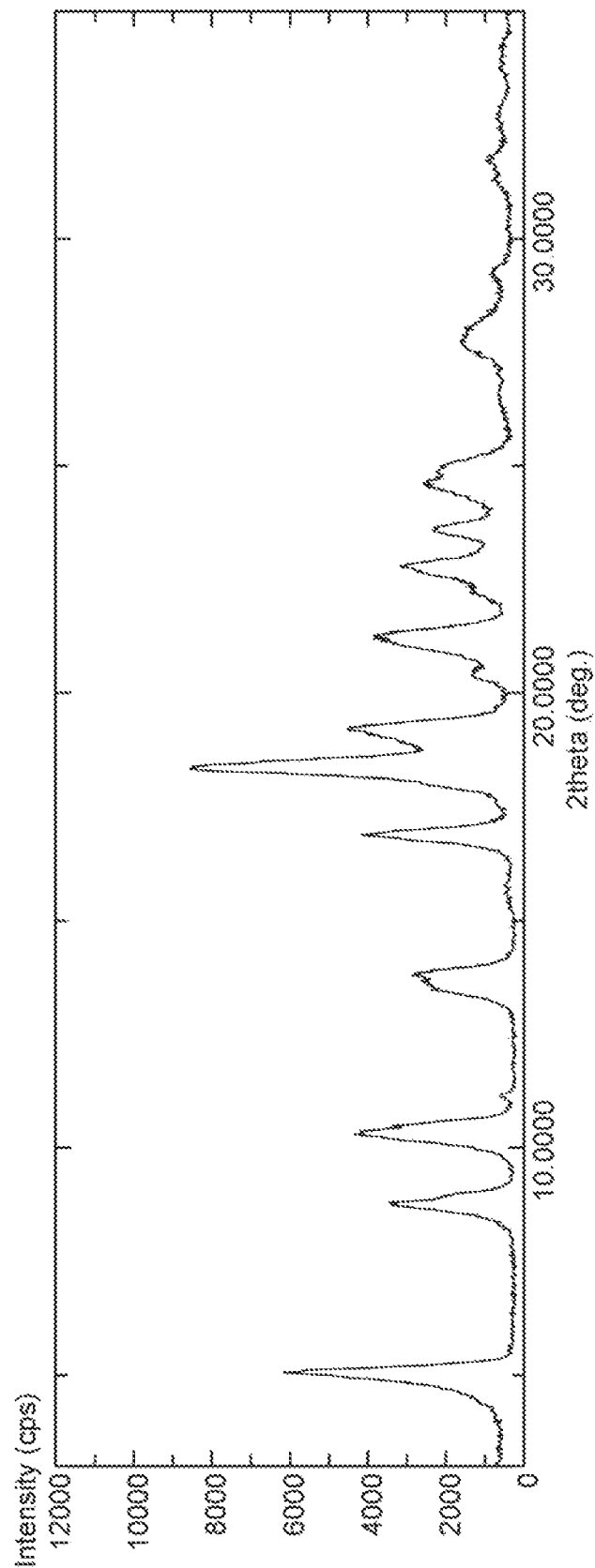

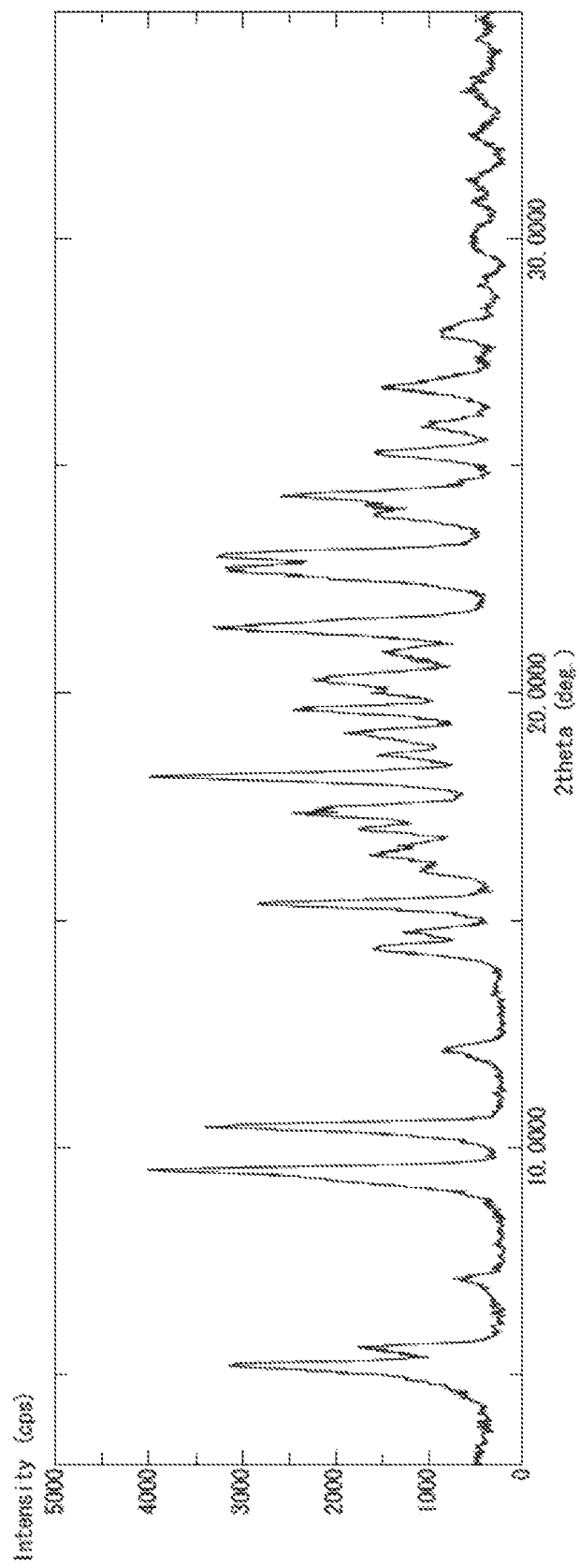

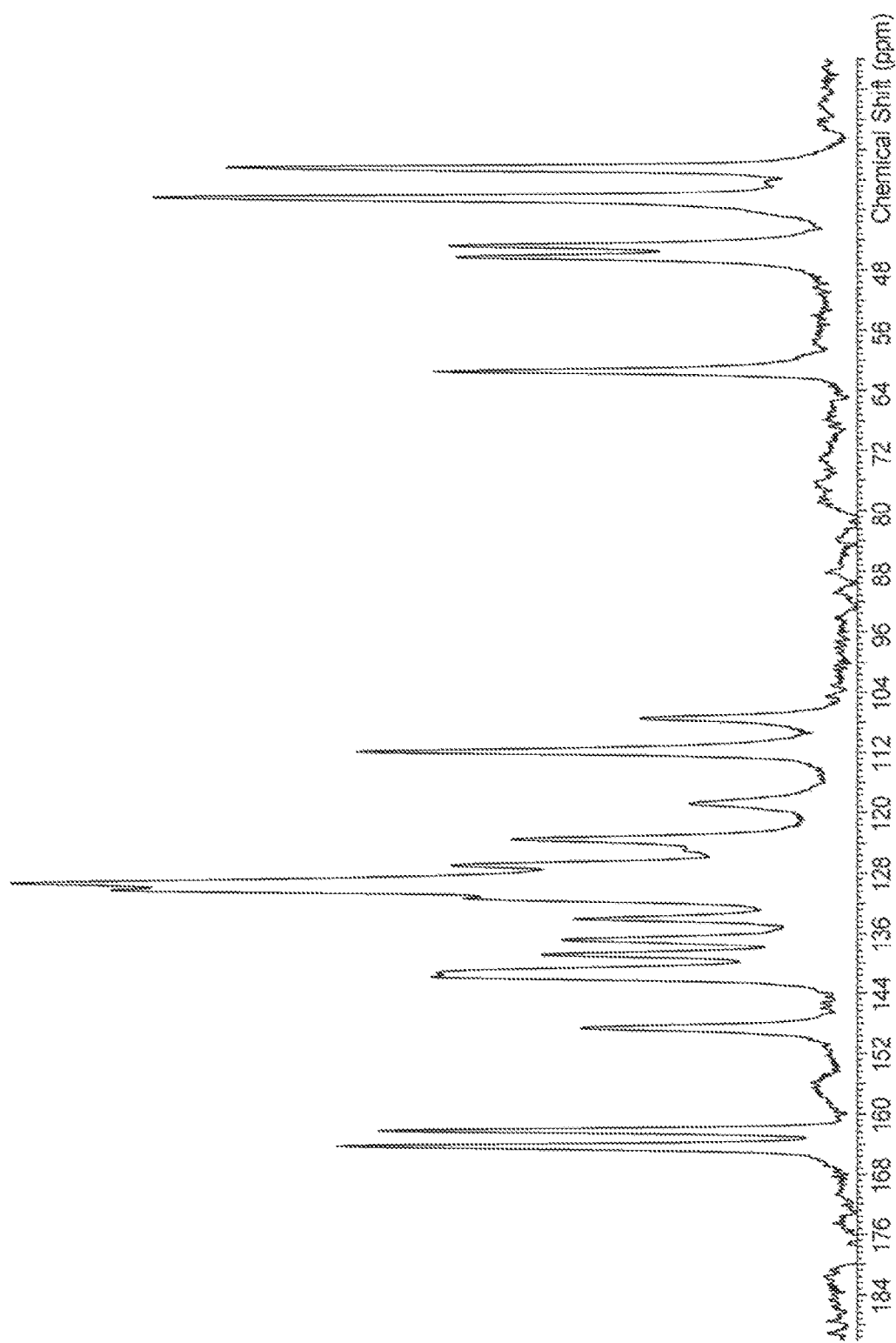
[Fig. 7]

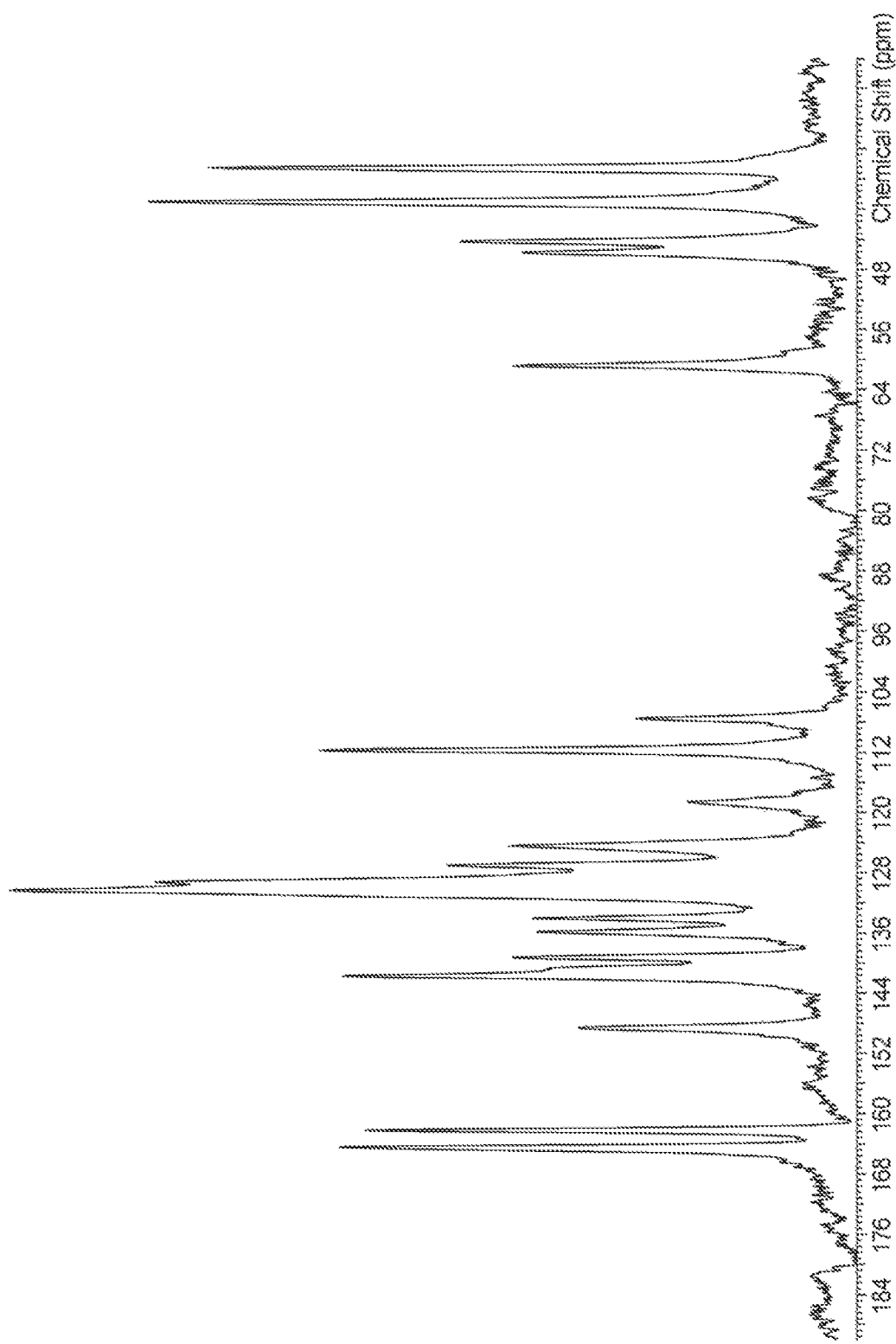

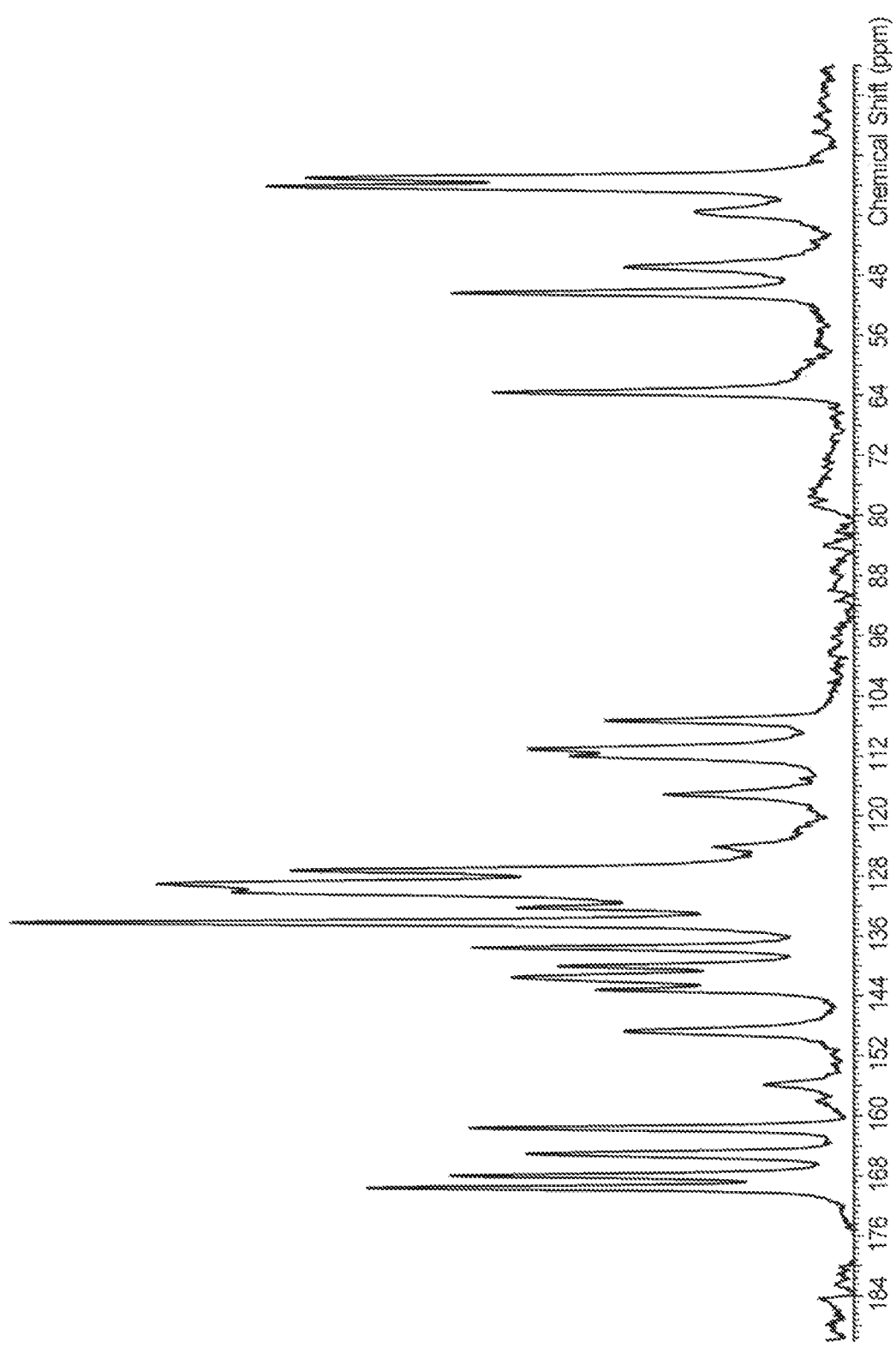
[Fig. 9]

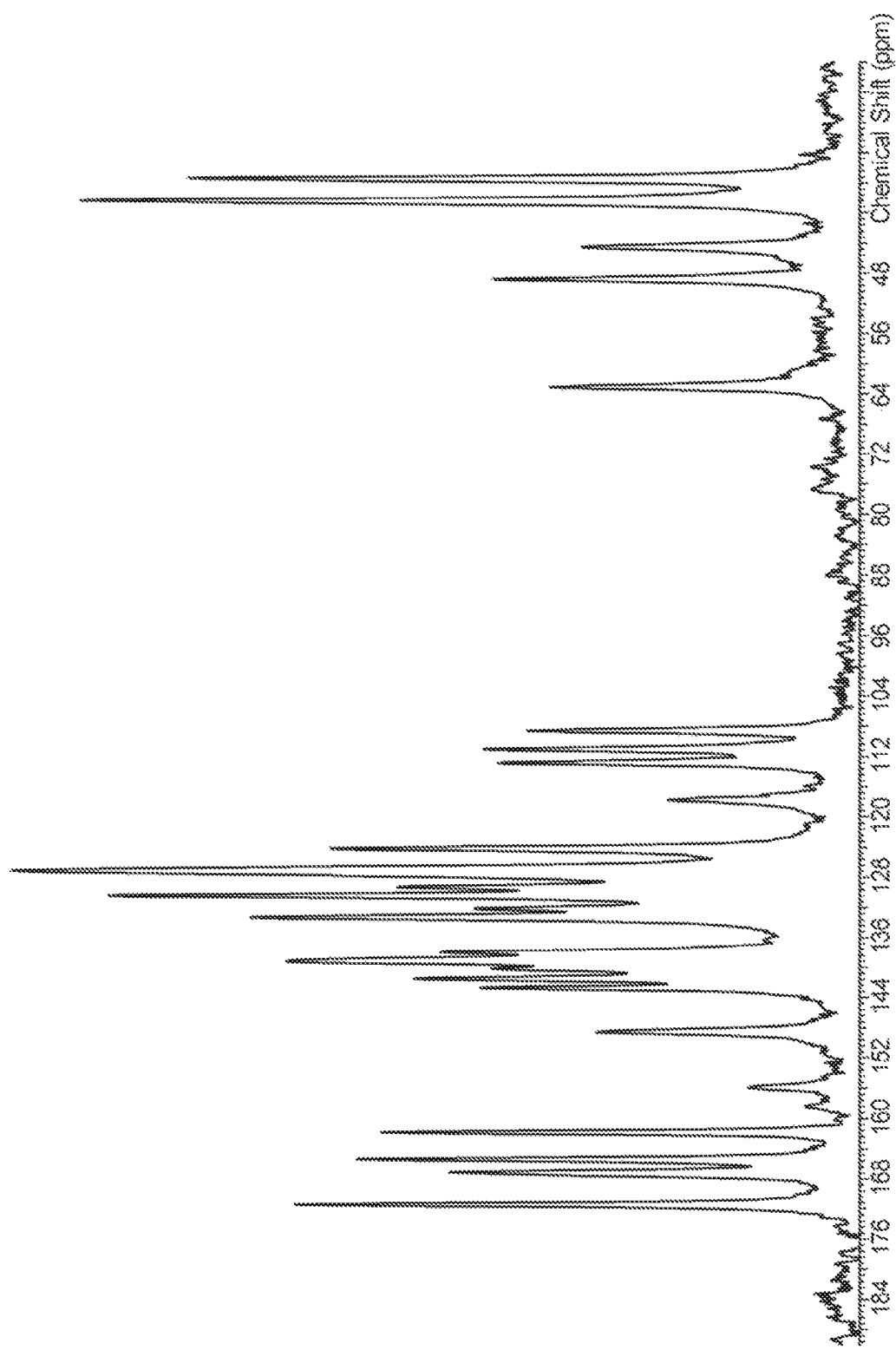

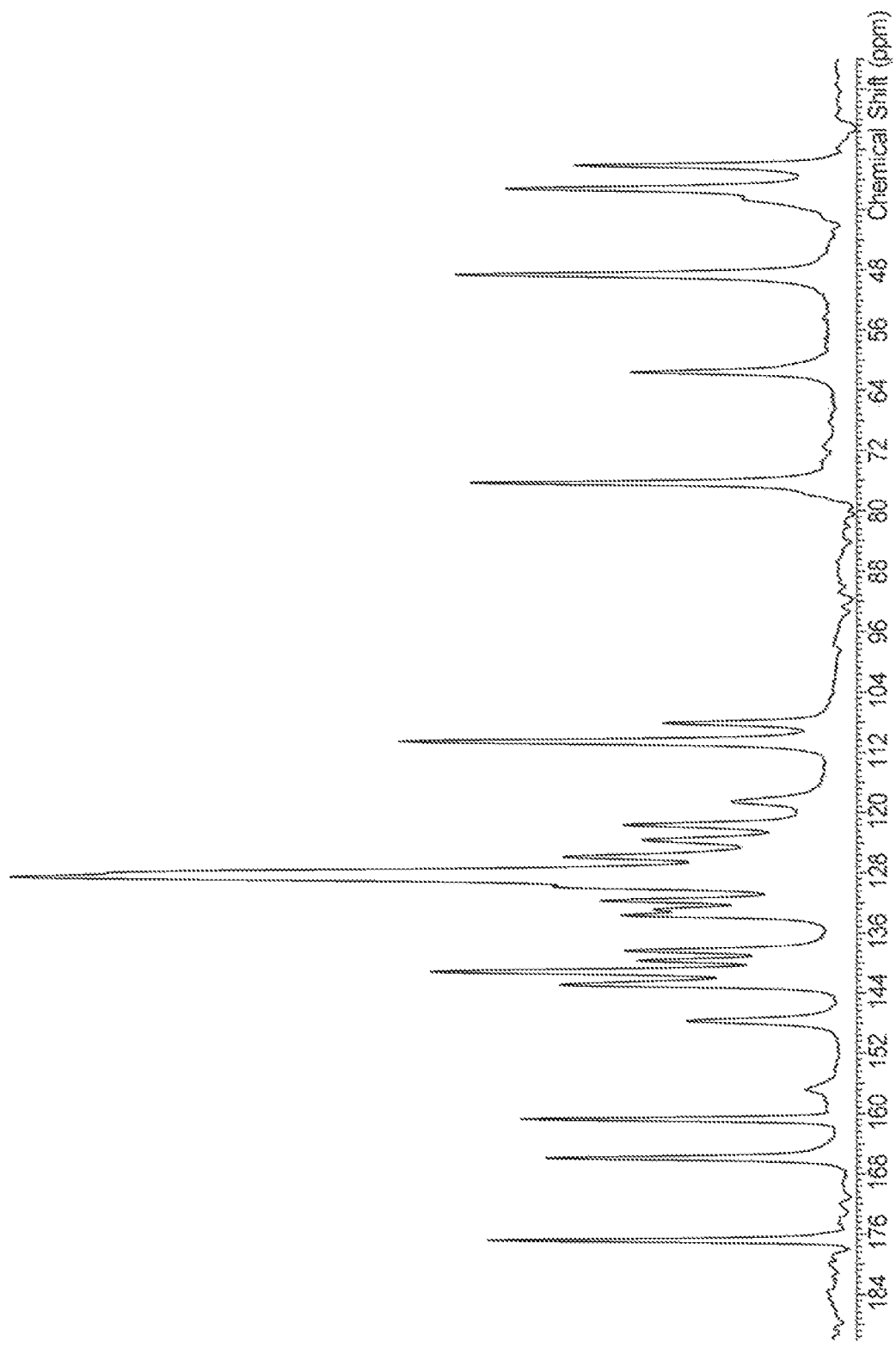
[Fig. 11]

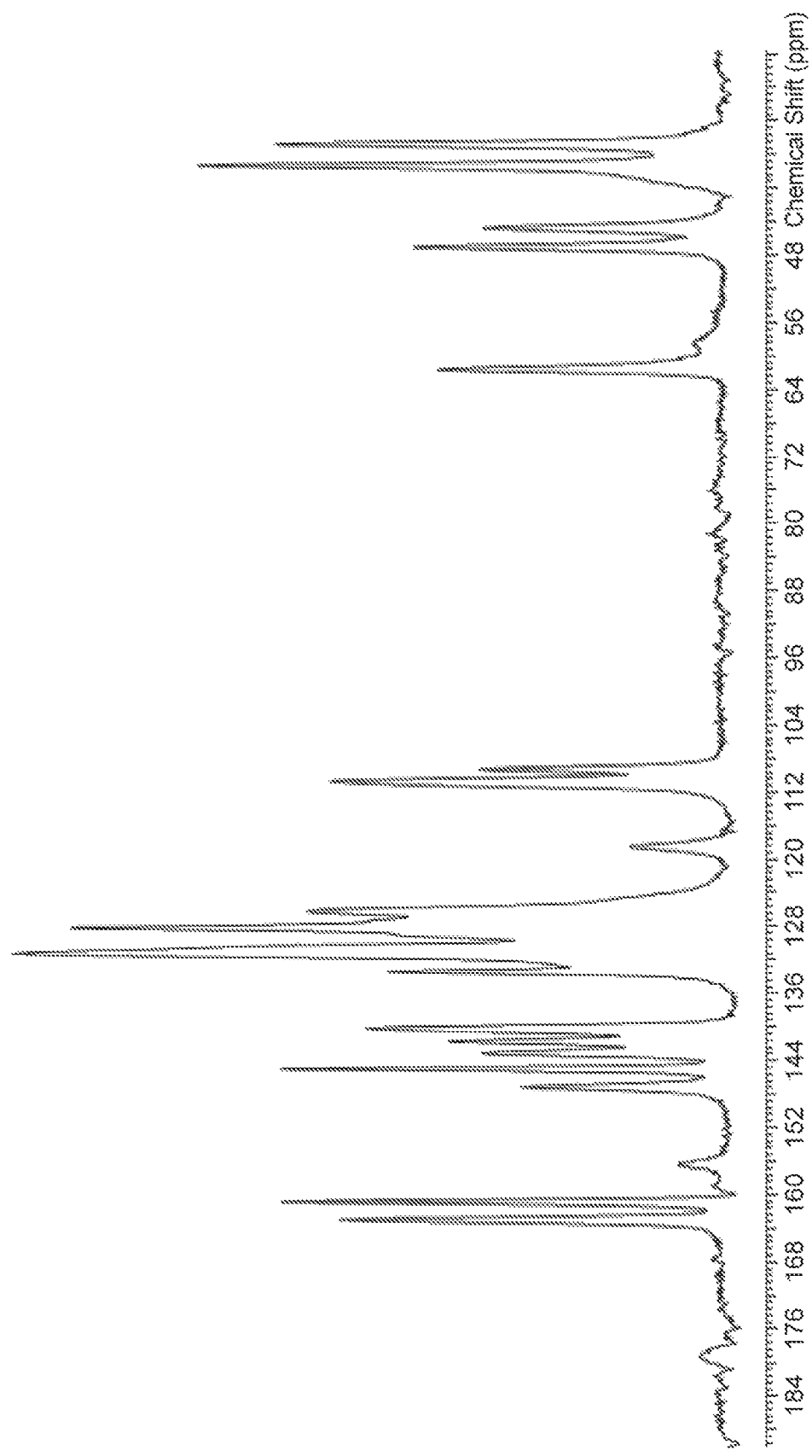
[Fig. 12]

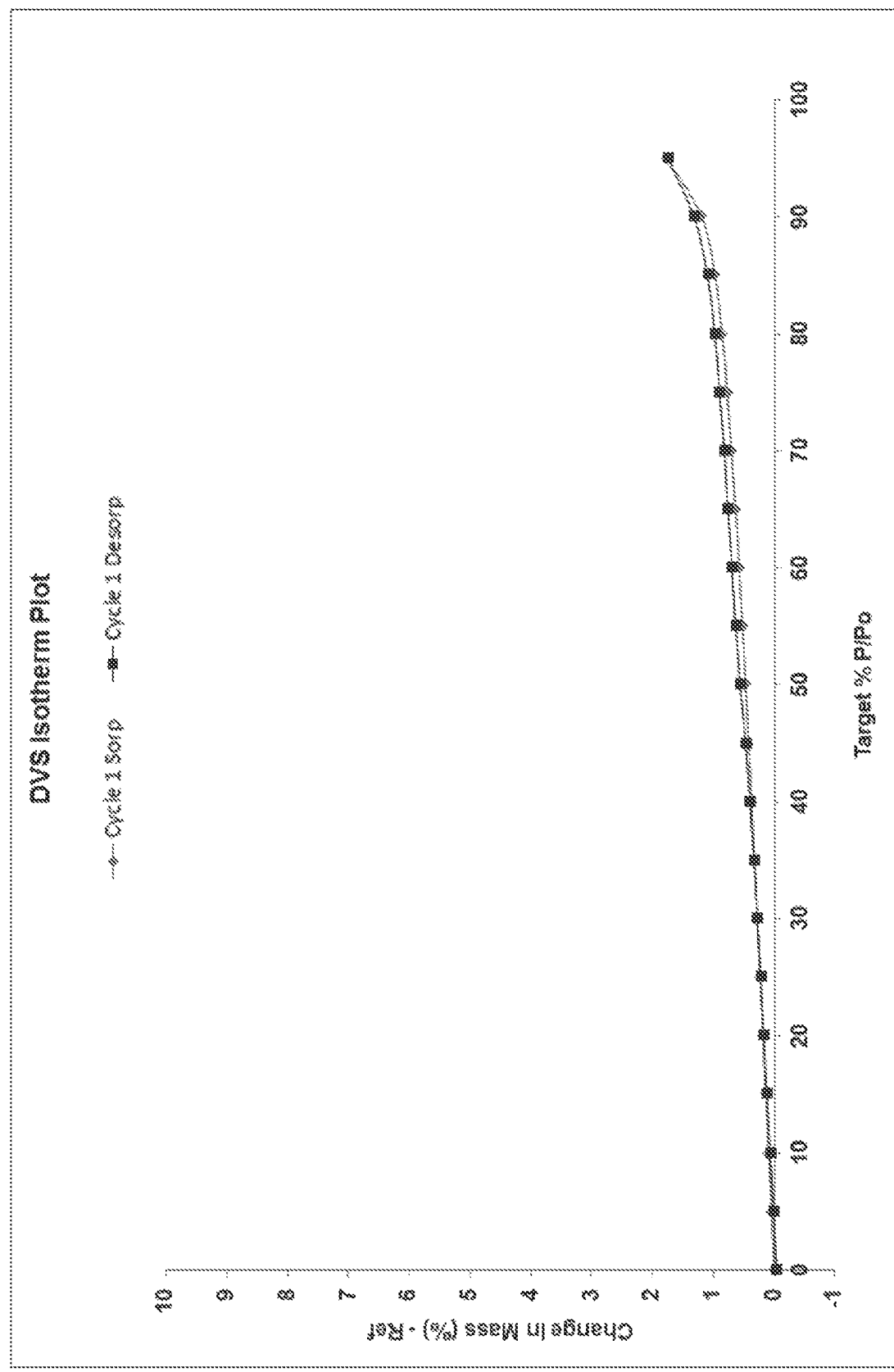
[Fig. 13]

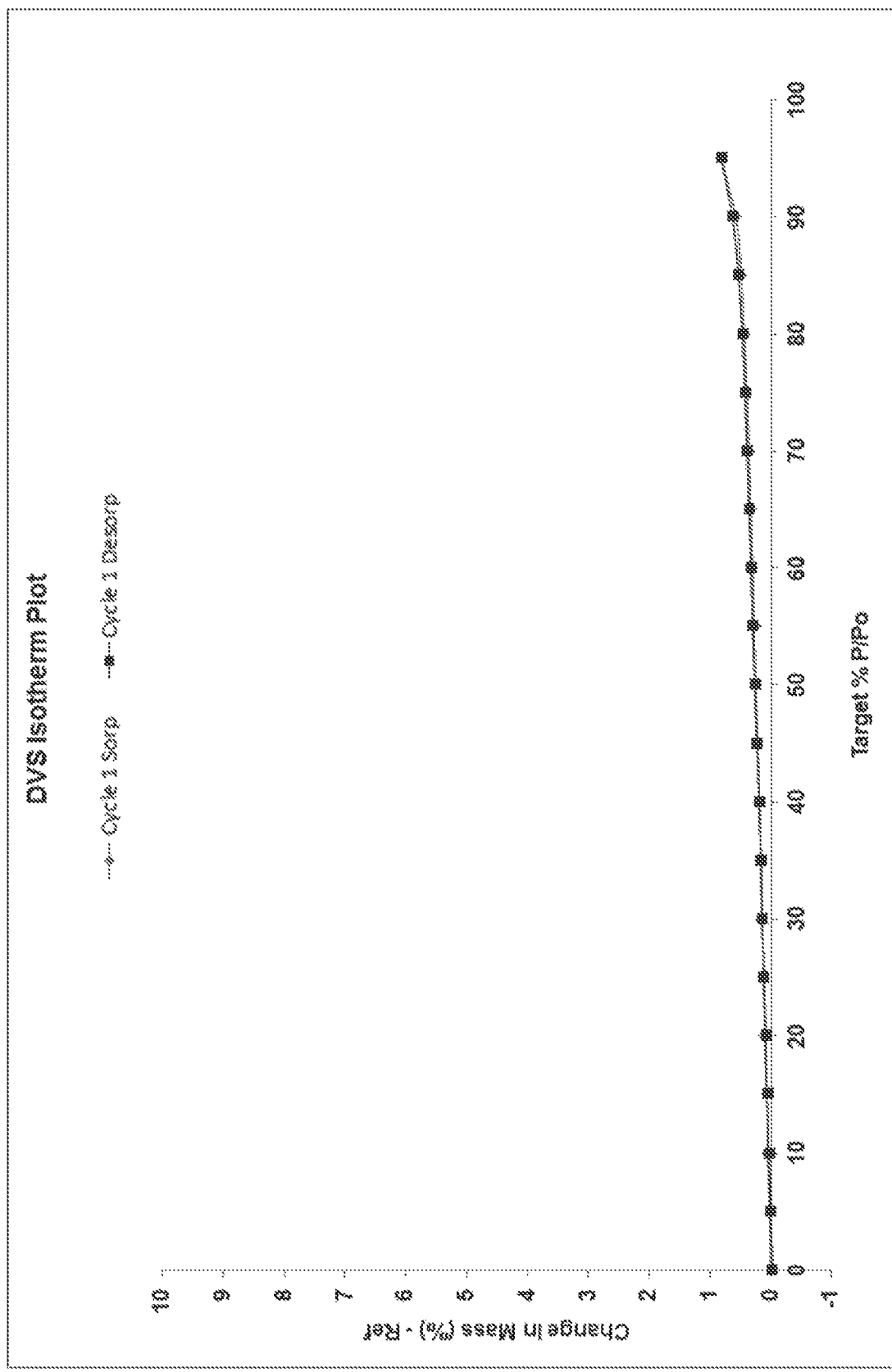

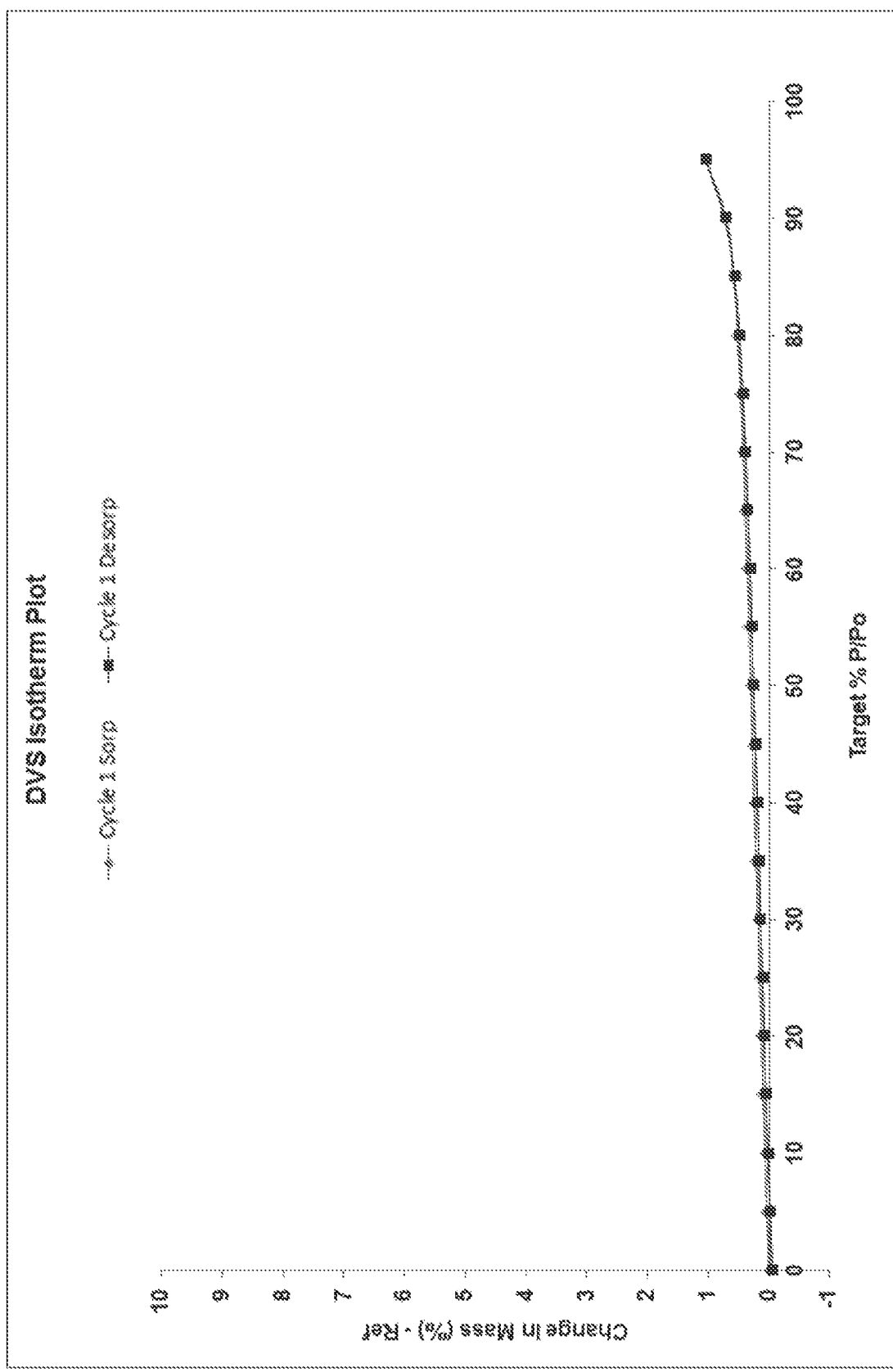
[Fig. 15]

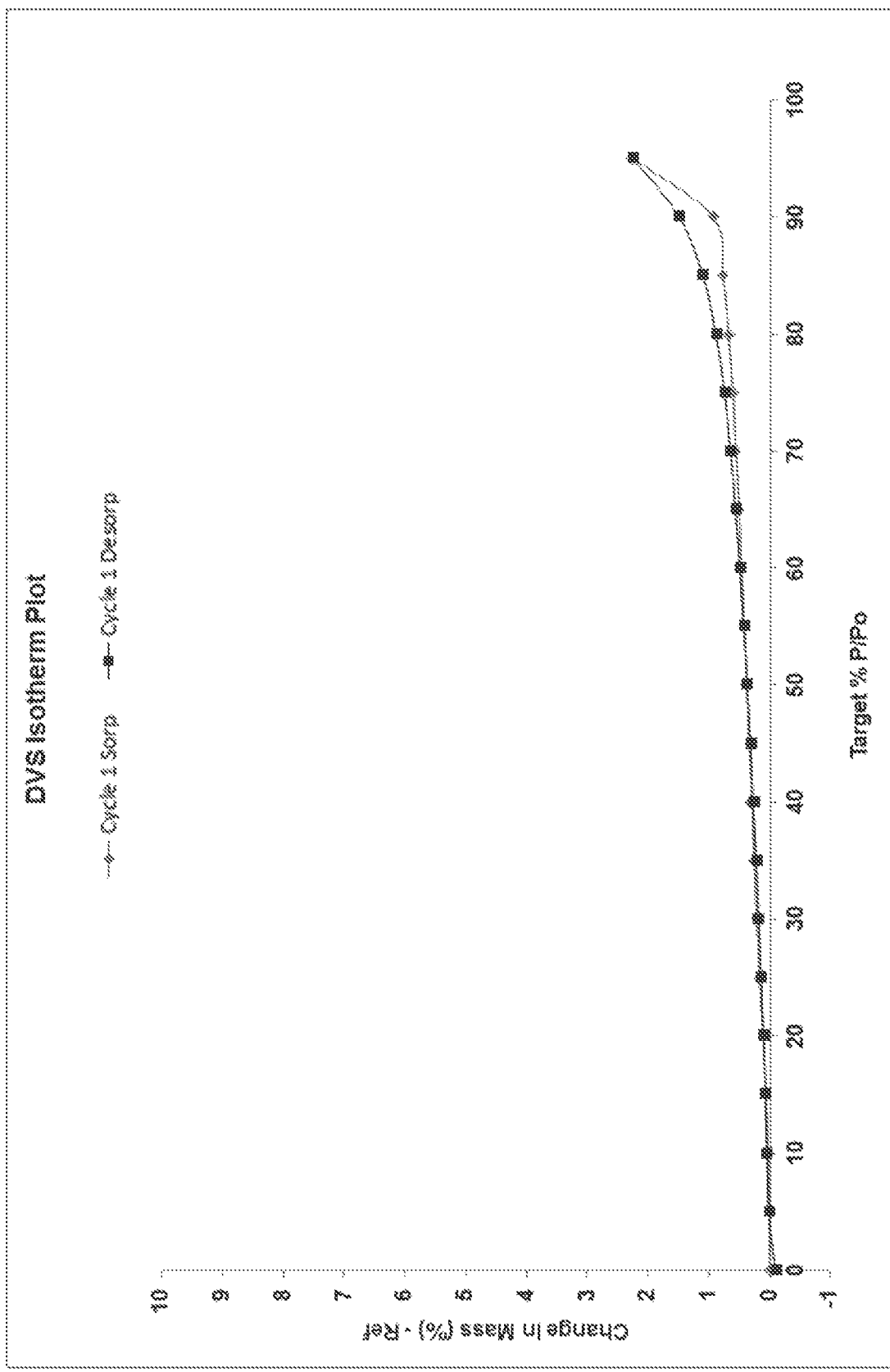

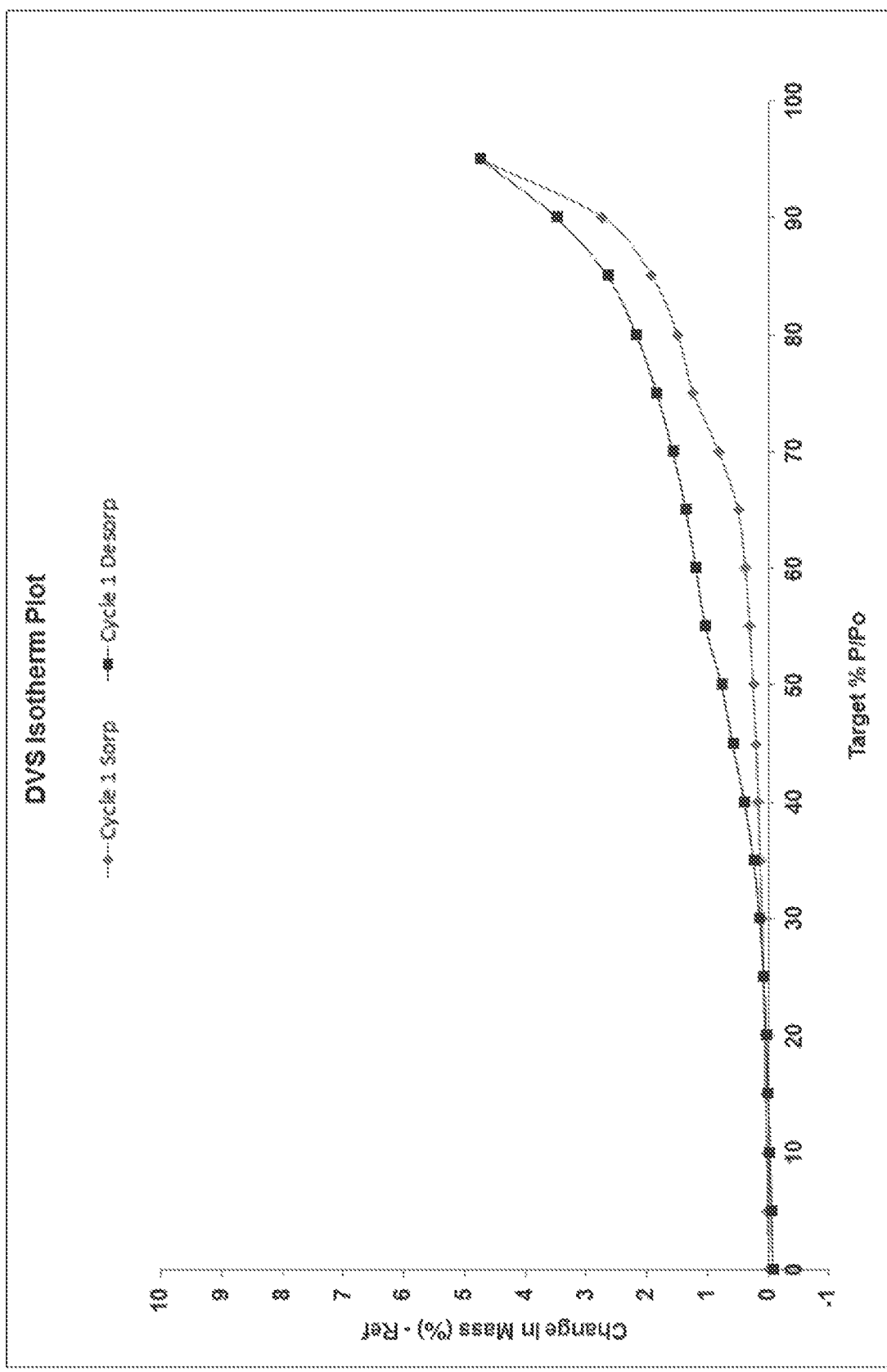
[Fig. 17]

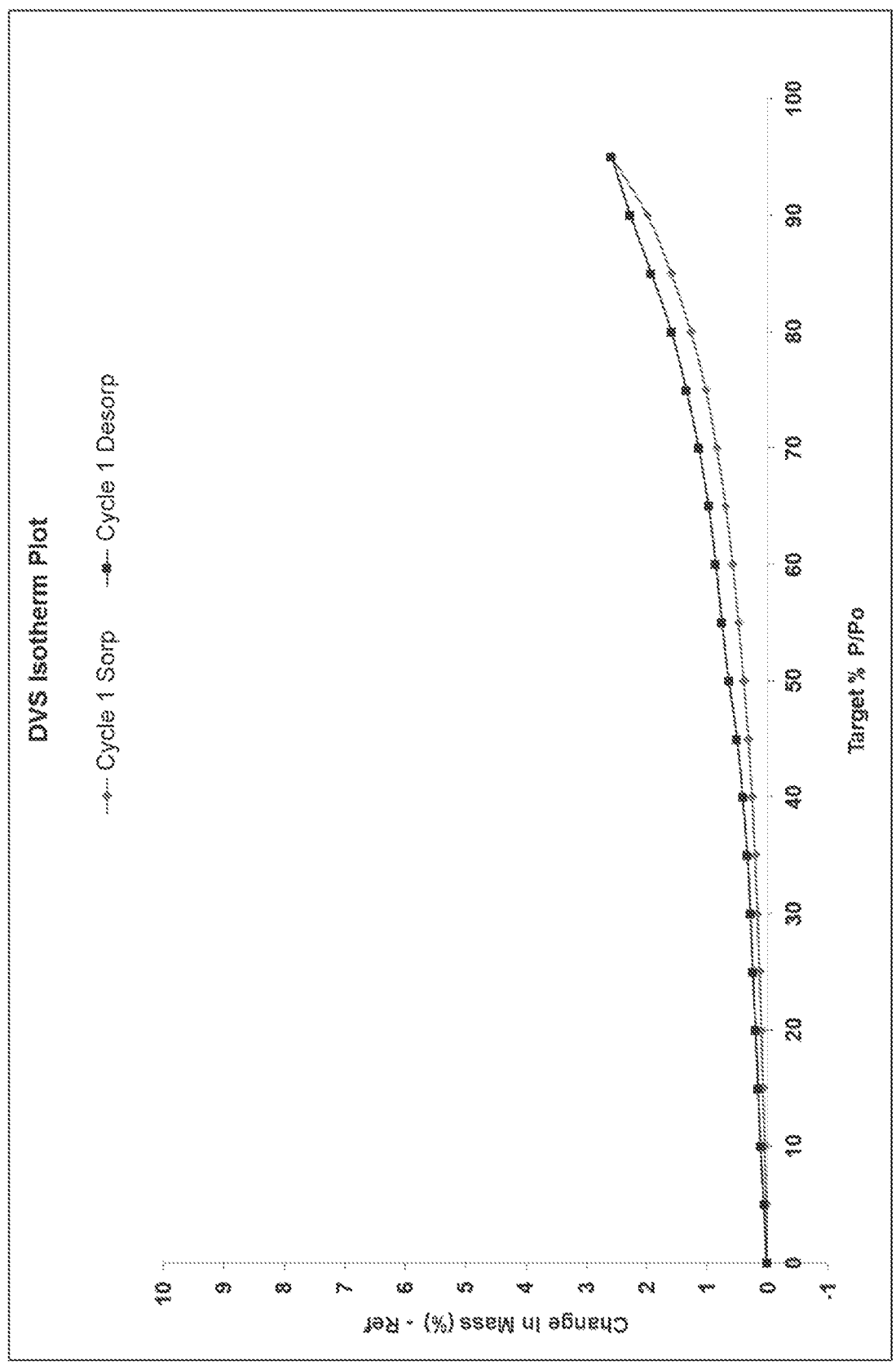
[Fig. 18]

[Fig. 19]
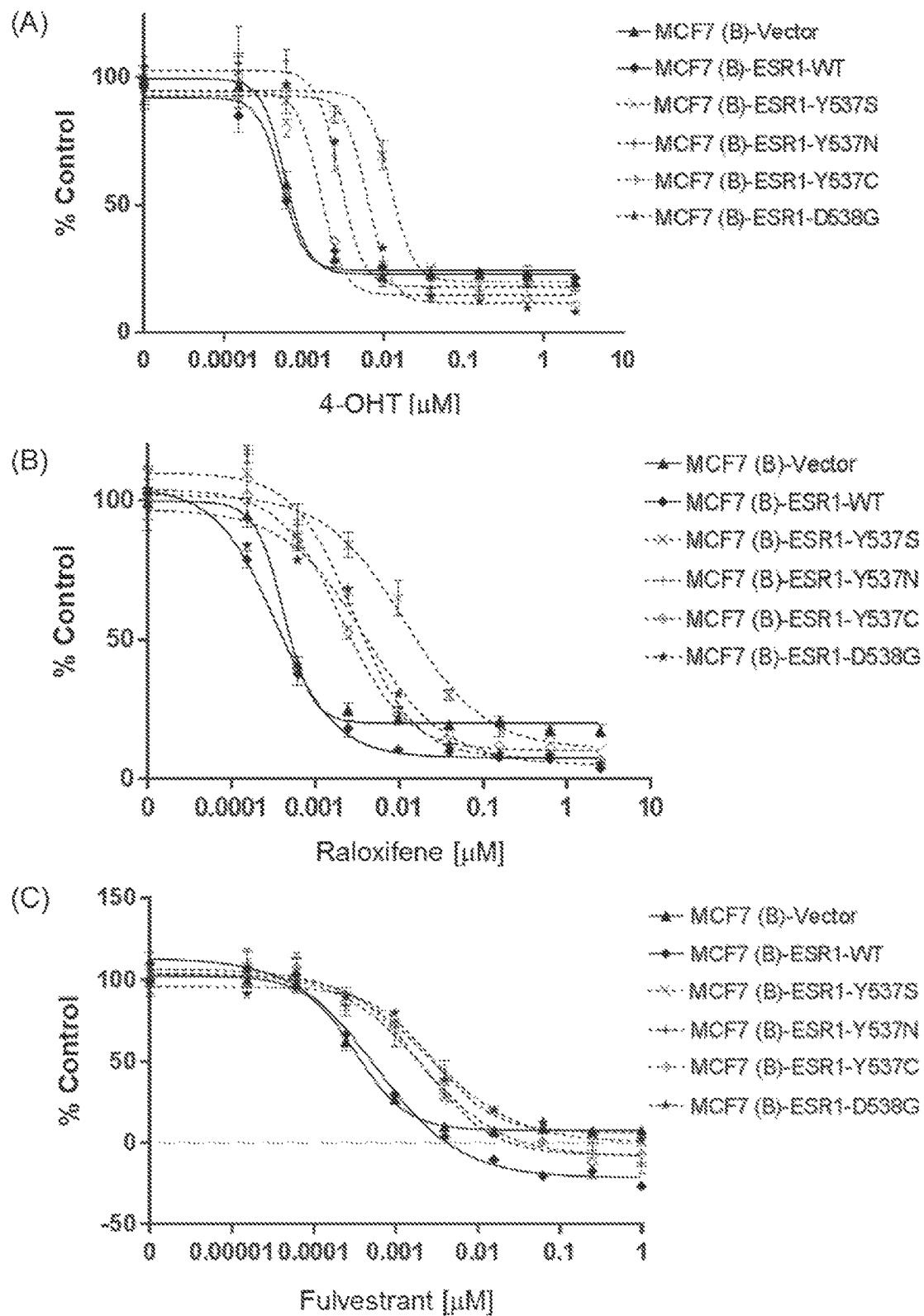

[Fig. 20]
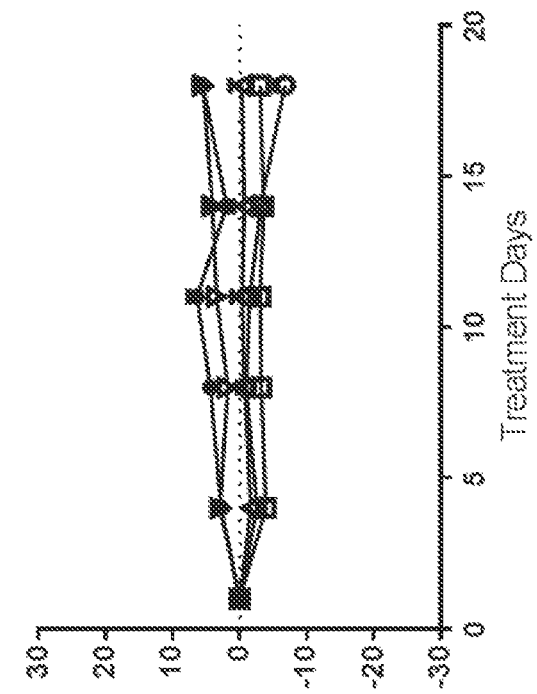
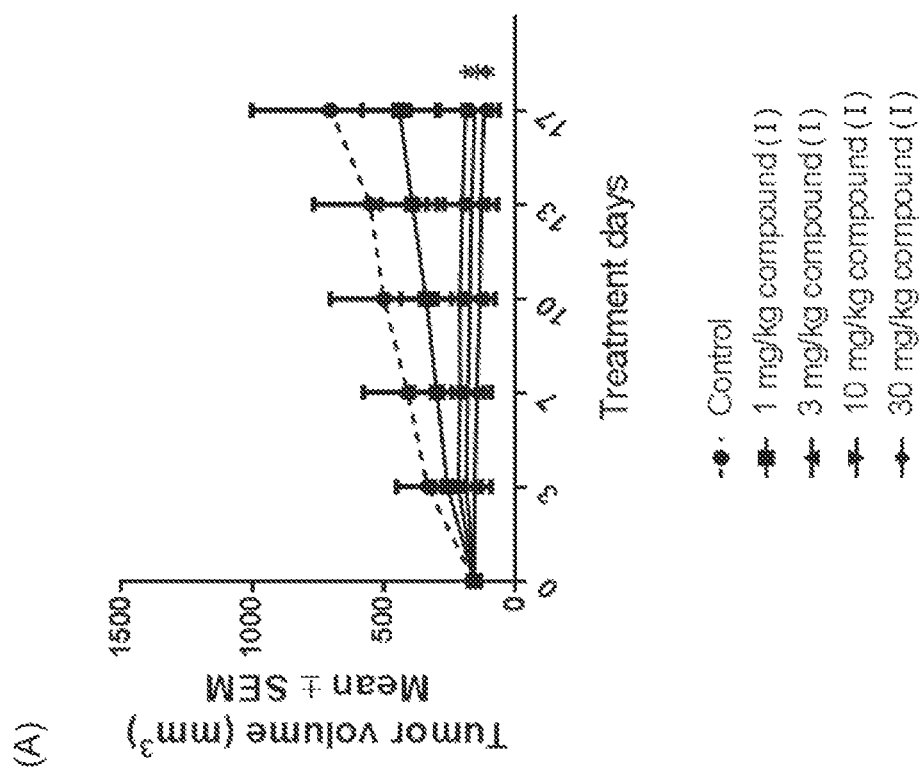

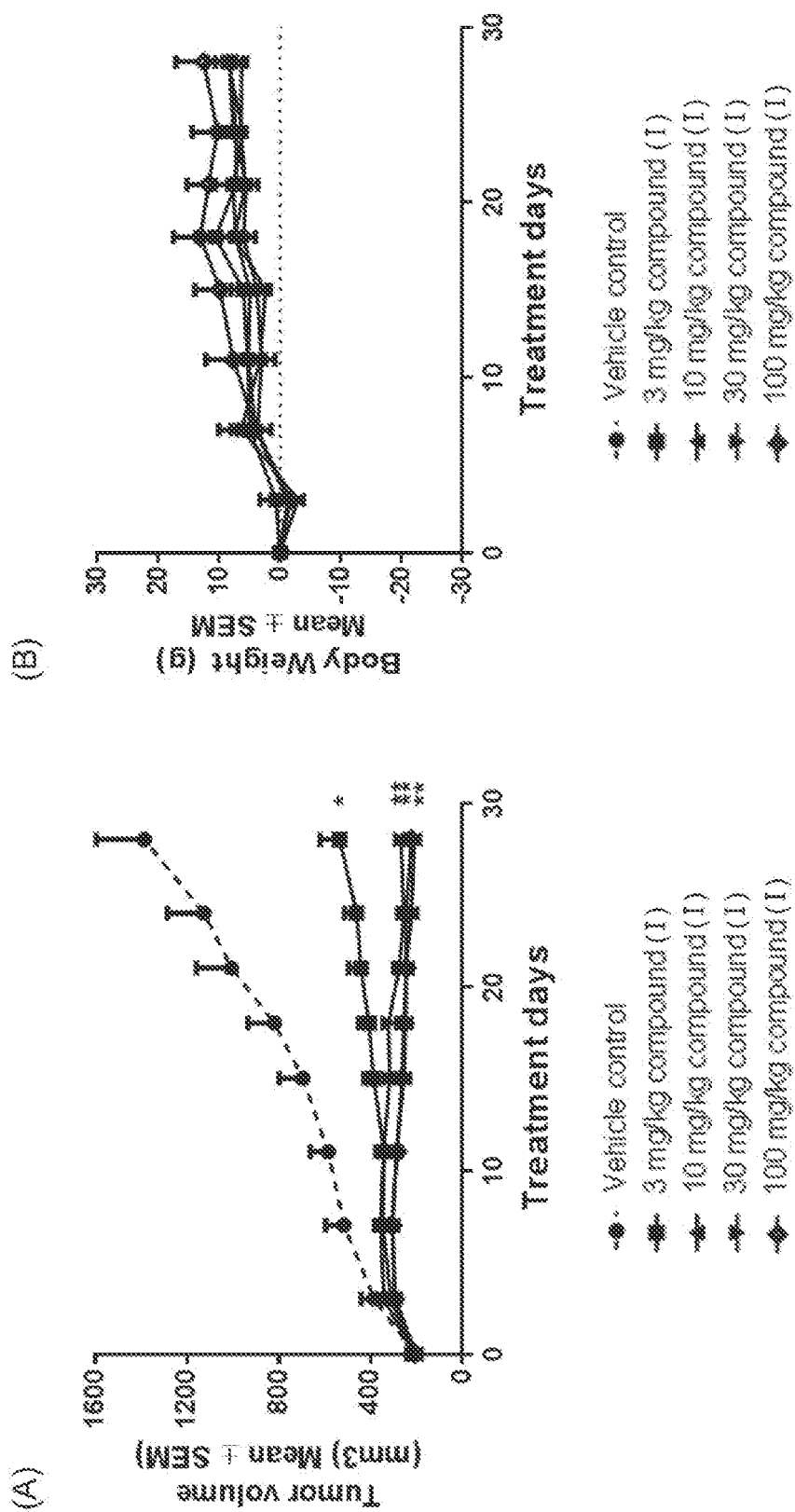
[Fig. 21]

[Fig. 22]
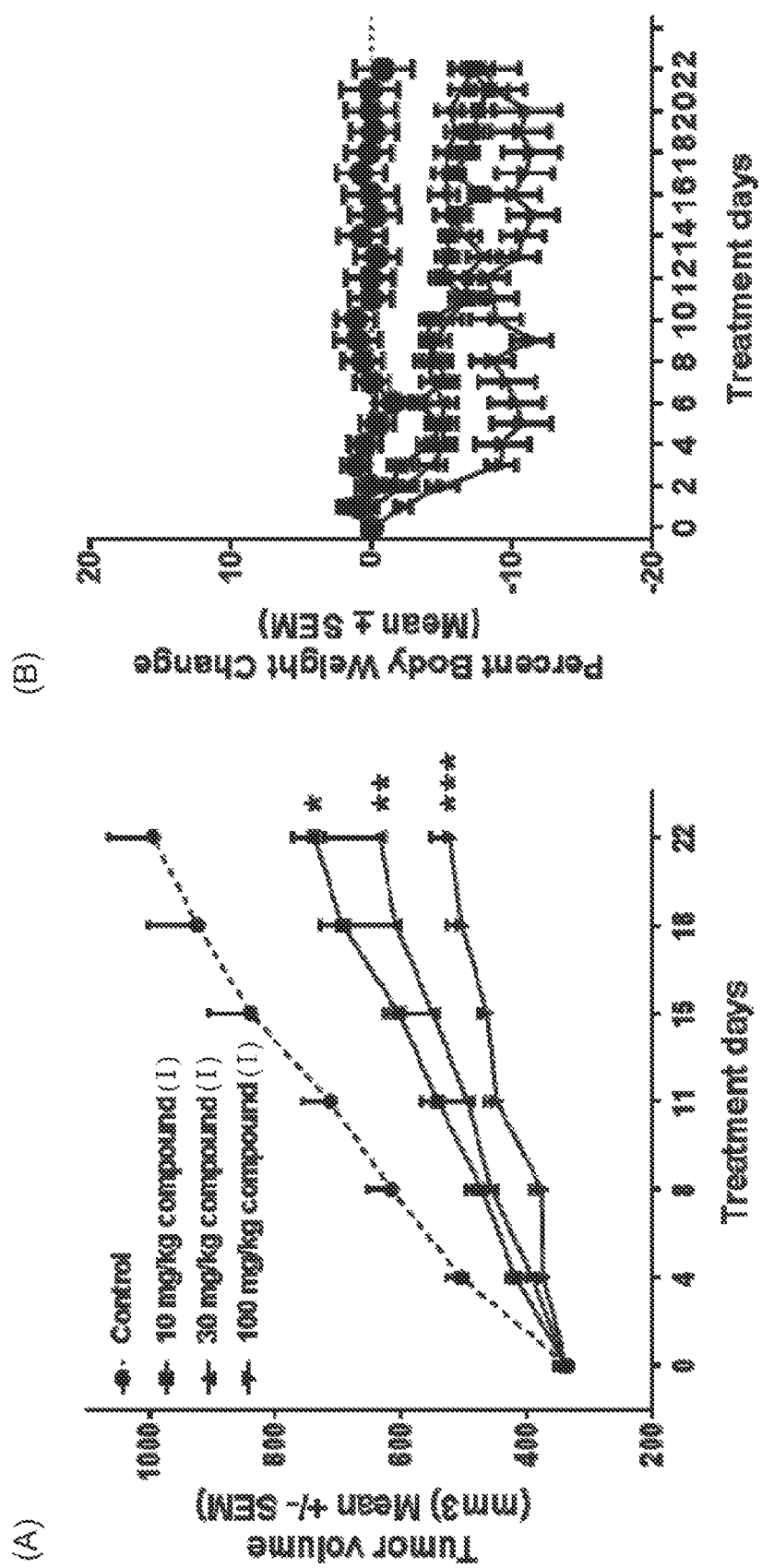

SALTS OF INDAZOLE DERIVATIVE AND CRYSTALS THEREOF

TECHNICAL FIELD

The present invention relates to salts of an indazole derivative and crystals thereof.

BACKGROUND ART

Breast cancer is the most commonly diagnosed malignancy among women today with nearly 200,000/1.7 million new cases diagnosed in the US/worldwide each year respectively. Since about 70% of breast tumors are positive for the estrogen receptor alpha (ERα)—a key oncogenic driver in this subset of tumors—several classes of therapies have been developed to antagonize ERα function, including 1) selective estrogen receptor downregulators (SERDs) of which fulvestrant is an example, 2) selective estrogen receptor modulators (SERMs) of which tamoxifen is an example and 3) aromatase inhibitors that reduce systemic levels of estrogen. These therapies have been largely effective in the clinic reducing occurrence and progression of ERα+ breast tumors. However there are on-target liabilities associated with these different classes of compounds. For example, tamoxifen has been shown to activate signaling activity in the endometrium leading to an increase in risk of endometrial cancers in the clinic (Fisher et al., (1994) J. Natl. Cancer Inst. April 6; 86 (7): 527-37; van Leeuwen et al., (1994) Lancet February 19; 343 (8895): 448-52). In contrast, since fulvestrant is a pure antagonist, it can lead to loss of bone density in post-menopausal women as ERα activity is critical for bone building. In addition to on-target side effects, clinical resistance is also beginning to emerge to these classes of ERα antagonists highlighting the need to develop next-generation compounds.

Several mechanisms of resistance have been identified using in vitro and in vivo models of resistance to various endocrine therapies. These include increased ERα/HER2 "crosstalk" (Shou et al., (2004) J. Natl. Cancer Inst. June 16; 96 (12): 926-35), aberrant expression of ERα coactivators/corepressors (Osborne et al., (2003) J. Natl. Cancer Inst. March 5; 95(5): 353-61) or loss of ERα altogether to allow ER-independent growth (Osborne C K, Schiff R (2011) Annu. Rev. Med. 62: 233-47).

In the hopes of identifying clinically relevant mechanisms of resistance, great effort has also recently gone into deeply characterizing the genetics of endocrine-therapy resistant metastases isolated from patients. Several independent labs have recently published the multitude of genetic lesions observed in the resistant vs the primary tumors (Li et al., (2013) Cell Rep. September 26; 4(6): 1116-30; Robinson et al., (2013) Nat. Genet. December; 45 (12): 1446-51; Toy et al., (2013) Nat. Genet. 2013 December; 45(12):1439-45). Among these are the highly recurrent mutations in the ligand-binding domain of ESR1 (gene which encodes ERα protein) found to be significantly enriched in about 20% of resistant tumors relative to endocrine therapy naive tumors (Jeselsohn et al., (2014) Clin. Cancer Res. April 1; 20 (7): 1757-67; Toy et al., (2013) Nat. Genet. 2013 December; 45 (12): 1439-45; Robinson et al., (2013) Nat. Genet. December; 45 (12): 1446-51; Merenbakh-Lamin et al., (2013) Cancer Res. December 1; 73 (23): 6856-64; Yu et al., (2014) Science July 11; 345 (6193): 216-20; Segal and Dowsett (2014), Clin. Cancer Res. April 1; 20 (7): 1724-6), suggesting the potential for these mutations to functionally drive clinical resistance. In contrast to the enrichment in ESR1 mutations observed in therapy-resistant tumors, mutations in other cancer-related genes failed to show such a robust enrichment strongly implying the importance of ERα mutations in promoting resistance (Jeselsohn et al., (2014) Clin. Cancer Res. April 1; 20 (7): 1757-67).

ER+ breast cancer patients on average are treated with seven independent therapies including chemotherapies and various anti-estrogen therapies such as tamoxifen, fulvestrant and aromatase inhibitors. Recent genomic profiling has revealed that the ERα pathway remains a critical driver of tumor growth in the resistant setting as activating mutations in ERα have emerged. Thus, it is critical that more potent ER-directed therapies be developed that can overcome resistance in the clinical setting. Hence, there is a need for novel compounds that can potently suppress the growth of both wild-type (WT) and ERα-mutant positive tumors.

SUMMARY OF INVENTION

Technical Problem

A compound represented by the formula I, namely, (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide (hereafter referred to as compound (I)), suppresses the growth of both wild-type (WT) and ER α-mutant positive tumors.

[Chem.1]

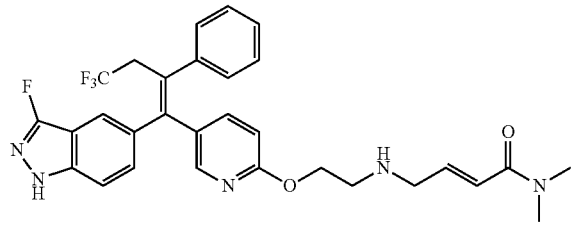

formula I

Generally, the physical properties of a compound, salts thereof, and their crystals used as a pharmaceutical product largely influence on the bioavailability of a drug, the purity of an active pharmaceutical ingredient, prescription of a preparation and the like. An object of the present invention is therefore to provide salts of compound (I) or crystals thereof with a potential to be used as drug substance in pharmaceuticals.

Solution to Problem

The present inventor has found salts of compound (I) or crystals thereof with a potential to be used as drug substance in pharmaceuticals, thereby completing the invention.

Specifically, the present invention provides the following <1> to <38>.

<1> A salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, and an acid selected from the group consisting of hydrobromic acid, maleic acid, mandelic acid and benzenesulfonic acid.

[Chem.2]

formula I

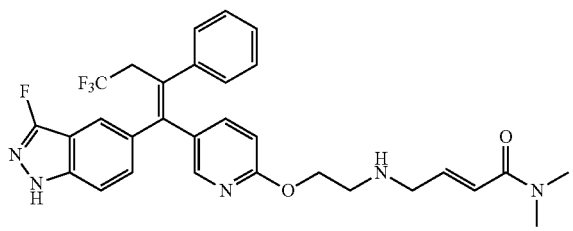

<2> A crystal of hydrochloride salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having one or more diffraction peaks at diffraction angles (2θ±0.2°) selected from the group consisting of 6.1°, 11.8°, 16.8°, 18.1° and 19.5° in a powder X-ray diffractometry.

[Chem.3]

formula I

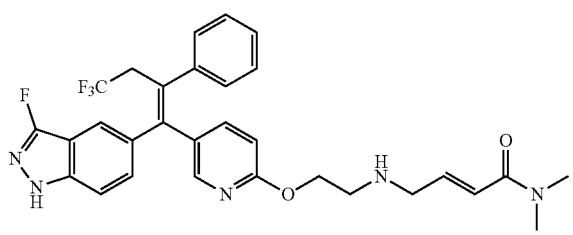

<3> The crystal according to <2> above, characterized by having a diffraction peak at a diffraction angle (2θ±0.2° of 18.1° in a powder X-ray diffractometry.
<4> The crystal according to <2> above, characterized by having diffraction peaks at diffraction angles (2θ±0.2° of 6.1°, 11.8° and 18.1° in a powder X-ray diffractometry.
<5> A crystal of hydrochloride salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having peaks at chemical shifts (±0.5 ppm) of 164.3 ppm, 162.2 ppm and 111.9 ppm in a solid state $^{13}$C NMR spectrum.

[Chem.4]

formula I

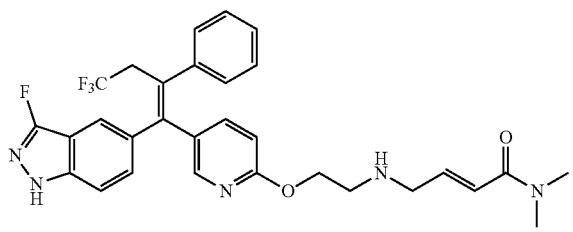

<6> A crystal of hydrochloride salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having a powder X-ray diffraction pattern substantially the same as the powder X-ray diffraction pattern shown in FIG. 1.

[Chem.5]

formula I

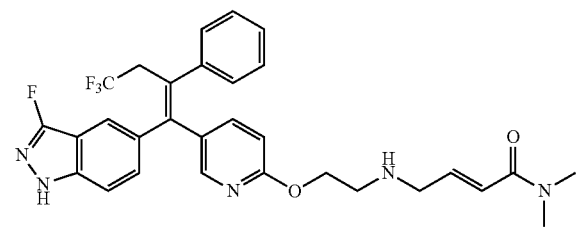

<7> A crystal of hydrochloride salt of (E)-N,N-dimethyl-4-((2-(5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having a solid state $^{13}$C NMR spectrum substantially the same as the solid state $^{13}$C NMR spectrum shown in FIG. 7.

[Chem.6]

formula I

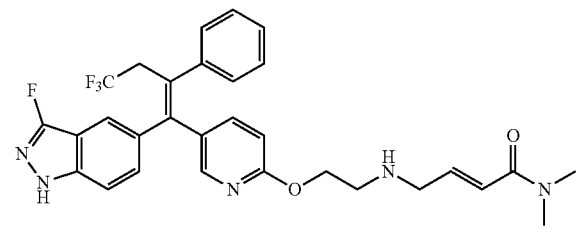

<8> A crystal of hydrobromide salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having one or more diffraction peaks at diffraction angles (2θ±0.2°) selected from the group consisting of 6.2°, 11.7°, 18.7°, 20.4° and 22.5° in a powder X-ray diffractometry.

[Chem.7]

formula I

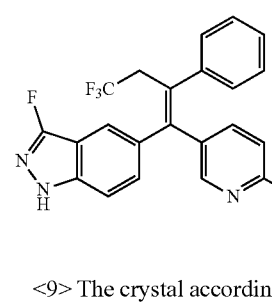

<9> The crystal according to <8> above, characterized by having a diffraction peak at a diffraction angle (2θ±0.2° of 18.7° in a powder X-ray diffractometry.
<10> The crystal according to <8> above, characterized by having diffraction peaks at diffraction angles (2θ±0.2°) of 6.2°, 18.7° and 22.5° in a powder X-ray diffractometry.

<11> A crystal of hydrobromide salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having peaks at chemical shifts (±0.5 ppm) of 164.5 ppm, 162.2 ppm and 111.7 ppm in a solid state $^{13}$C NMR spectrum.

[Chem.8]

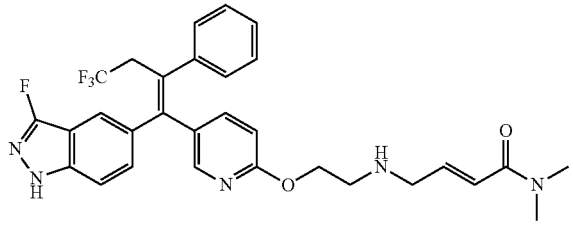

formula I

<12> A crystal of hydrobromide salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having a powder X-ray diffraction pattern substantially the same as the powder X-ray diffraction pattern shown in FIG. 2.

[Chem. 9]

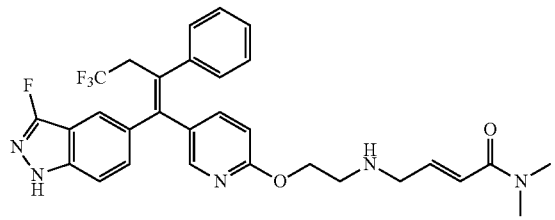

formula I

<13> A crystal of hydrobromide salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having a solid state $^{13}$C NMR spectrum substantially the same as the solid state $^{13}$C NMR spectrum shown in FIG. 8.

[Chem. 10]

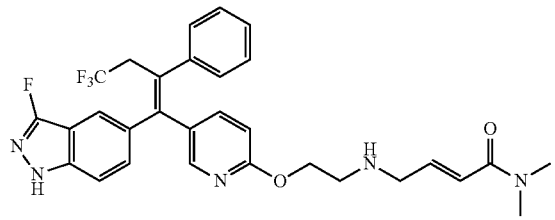

formula I

<14> A crystal form A of maleate salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having one or more diffraction peaks at diffraction angles (2θ±0.2° selected from the group consisting of 16.7°, 17.9°, 21.2°, 22.9° and 24.9° in a powder X-ray diffractometry.

[Chem. 11]

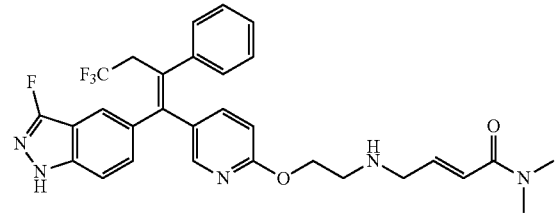

formula I

<15> The crystal according to <14> above, characterized by having a diffraction peak at a diffraction angle (2θ±0.2° of 24.9° in a powder X-ray diffractometry.

<16> The crystal according to <14> above, characterized by having diffraction peaks at diffraction angles (2θ±0.2°) of 17.9°, 22.9° and 24.9° in a powder X-ray diffractometry.

<17> A crystal form A of maleate salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having peaks at chemical shifts (±0.5 ppm) of 169.6 ppm, 107.3 ppm and 50.3 ppm in a solid state $^{13}$C NMR spectrum.

[Chem. 12]

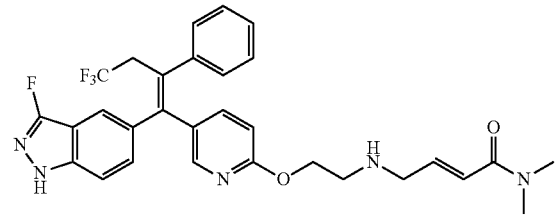

formula I

<18> A crystal form A of maleate salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having a powder X-ray diffraction pattern substantially the same as the powder X-ray diffraction pattern shown in FIG. 3.

[Chem. 13]

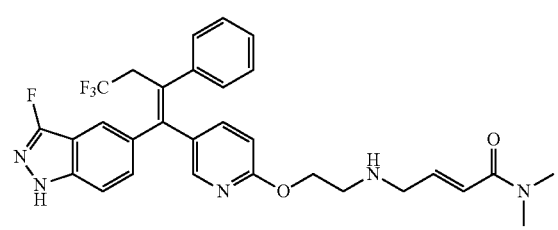

formula I

<19> A crystal form A of maleate salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having a solid state $^{13}$C NMR spectrum substantially the same as the solid state $^{13}$C NMR spectrum shown in FIG. 9.

[Chem. 14]

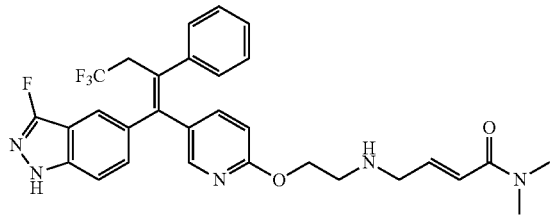

formula I

<20> A crystal form B of maleate salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having one or more diffraction peaks at diffraction angles (2θ±0.2°) selected from the group consisting of 14.8°, 20.2°, 22.3° and 26.5° in a powder X-ray diffractometry.

[Chem. 15]

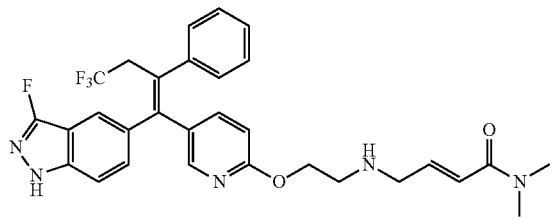

formula I

<21> The crystal according to <20> above, characterized by having a diffraction peak at a diffraction angle (2θ±0.2°) of 22.3° in a powder X-ray diffractometry.

<22> The crystal according to <20> above, characterized by having diffraction peaks at diffraction angles (2θ±0.2°) of 14.8°, 20.2° and 22.3° in a powder X-ray diffractometry.

<23> A crystal form B of maleate salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having peaks at chemical shifts (±0.5 ppm) of 171.4 ppm, 108.6 ppm and 48.8 ppm in a solid state $^{13}$C NMR spectrum.

[Chem. 16]

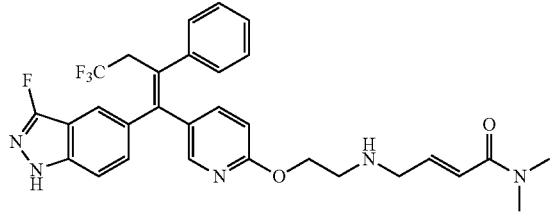

formula I

<24> A crystal form B of maleate salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having a powder X-ray diffraction pattern substantially the same as the powder X-ray diffraction pattern shown in FIG. 4.

[Chem. 17]

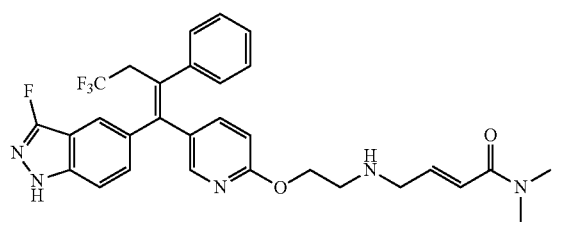

formula I

<25> A crystal form B of maleate salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having a solid state $^{13}$C NMR spectrum substantially the same as the solid state $^{13}$C NMR spectrum shown in FIG. 10.

[Chem. 18]

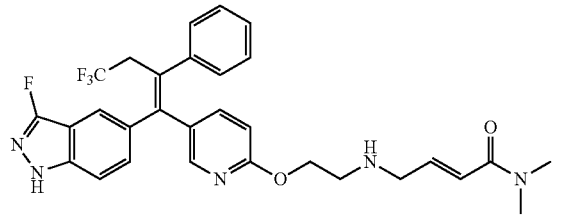

formula I

<26> A crystal of L-mandelate salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having one or more diffraction peaks at diffraction angles (2θ±0.2°) selected from the group consisting of 5.1°, 8.8°, 10.3°, 16.9° and 18.3° in a powder X-ray diffractometry.

[Chem. 19]

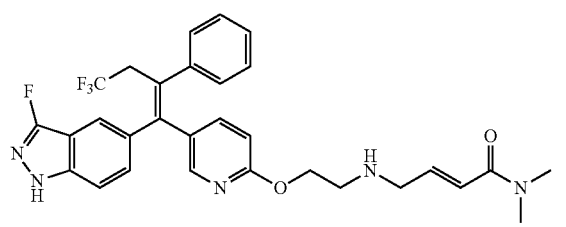

formula I

<27> The crystal according to <26> above, characterized by having a diffraction peak at a diffraction angle (2θ±0.2°) of 18.3° in a powder X-ray diffractometry.

<28> The crystal according to <26> above, characterized by having diffraction peaks at diffraction angles (2θ±0.2°) of 5.1°, 10.3° and 18.3° in a powder X-ray diffractometry.

<29> A crystal of L-mandelate salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having peaks at chemical shifts (±0.5 ppm) of 165.9 ppm, 160.7 ppm and 110.5 ppm in a solid state $^{13}$C NMR spectrum.

[Chem. 20]

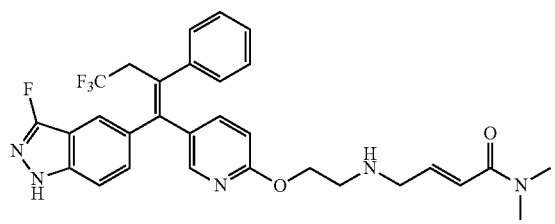

formula I

<30> A crystal of L-mandelate salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having a powder X-ray diffraction pattern substantially the same as the powder X-ray diffraction pattern shown in FIG. 5.

[Chem. 21]

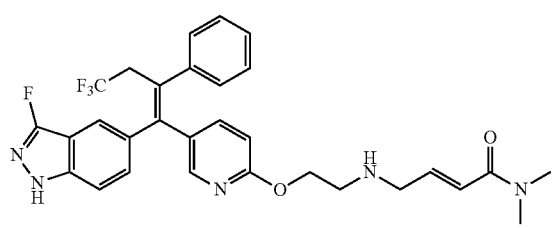

formula I

<31> A crystal of L-mandelate salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having a solid state $^{13}$C NMR spectrum substantially the same as the solid state $^{13}$C NMR spectrum shown in FIG. 11.

[Chem. 22]

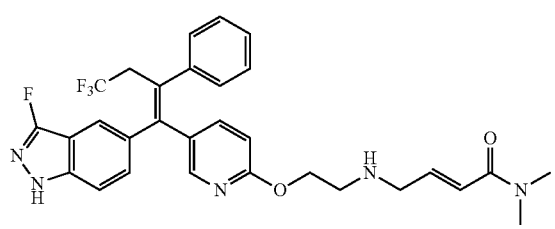

formula I

<32> A crystal of benzenesulfonate salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having one or more diffraction peaks at diffraction angles (2θ±0.2°) selected from the group consisting of 5.2°, 9.5°, 10.5°, 21.4° and 24.4° in a powder X-ray diffractometry.

[Chem. 23]

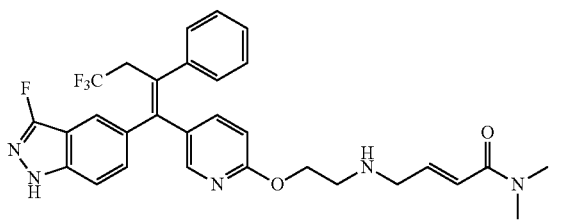

formula I

<33> The crystal according to <32> above, characterized by having a diffraction peak at a diffraction angle (2θ±0.2°) of 9.5° in a powder X-ray diffractometry.

<34> The crystal according to <32> above, characterized by having diffraction peaks at diffraction angles (2θ±0.2°) of 5.2°, 9.5° and 10.5° in a powder X-ray diffractometry.

<35> A crystal of benzenesulfonate salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having peaks at chemical shifts (±0.5 ppm) of 163.0 ppm, 147.2 ppm and 145.0 ppm in a solid state $^{13}$C NMR spectrum.

[Chem.24]

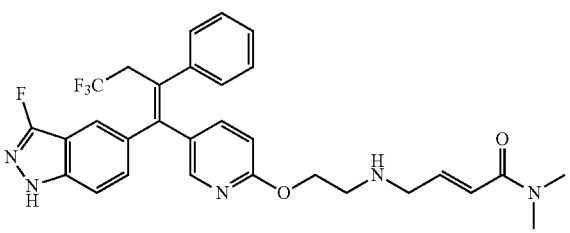

formula I

<36> A crystal of benzenesulfonate salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having a powder X-ray diffraction pattern substantially the same as the powder X-ray diffraction pattern shown in FIG. 6.

[Chem.25]

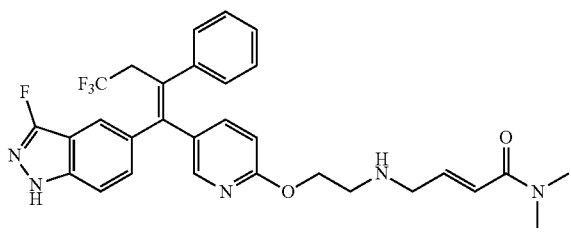

formula I

<37> A crystal of benzenesulfonate salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, characterized by having a solid state $^{13}$C NMR spectrum substantially the same as the solid state $^{13}$C NMR spectrum shown in FIG. 12.

[Chem.26]

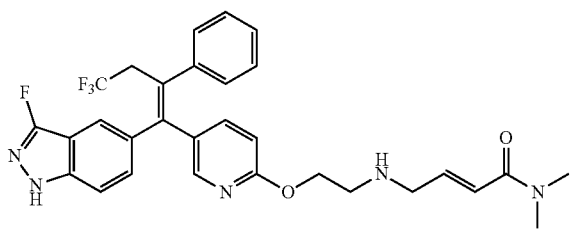

formula I

<38> A pharmaceutical composition comprising the salt or the crystal thereof according to any one of <1> to <37> above.

Advantageous Effects of Invention

The salts of compound (I) and the crystals thereof provided by the present invention possess properties such as hygroscopicity as shown in the examples described in later and a potential to be used as drug substance in pharmaceuticals.

BRIEF DESCRIPTION OF DRAWINGS

FIG. 1 shows a powder X-ray diffraction pattern of the crystal of the compound (I) hydrochloride salt obtained in Example 1. The abscissa shows the diffraction angle (2θ) and the ordinate shows the peak intensity.

FIG. 2 shows a powder X-ray diffraction pattern of the crystal of the compound (I) hydrobromide salt obtained in Example 2. The abscissa shows the diffraction angle (2θ) and the ordinate shows the peak intensity.

FIG. 3 shows a powder X-ray diffraction pattern of the crystal form A of the compound (I) maleate salt obtained in Example 3. The abscissa shows the diffraction angle (2θ) and the ordinate shows the peak intensity.

FIG. 4 shows a powder X-ray diffraction pattern of the crystal form B of the compound (I) maleate salt obtained in Example 4. The abscissa shows the diffraction angle (2θ) and the ordinate shows the peak intensity.

FIG. 5 shows a powder X-ray diffraction pattern of the crystal of the compound (I) L-mandelate salt obtained in Example 5. The abscissa shows the diffraction angle (2θ) and the ordinate shows the peak intensity.

FIG. 6 shows a powder X-ray diffraction pattern of the crystal of the compound (I) benzenesulfonate salt obtained in Example 6. The abscissa shows the diffraction angle (2θ) and the ordinate shows the peak intensity.

FIG. 7 shows a solid state $^{13}$C NMR spectrum of the crystal of the compound (I) hydrochloride salt obtained in Example 1. The abscissa shows the chemical shift (ppm) and the ordinate shows the peak intensity.

FIG. 8 shows a solid state $^{13}$C NMR spectrum of the crystal of the compound (I) hydrobromide salt obtained in Example 2. The abscissa shows the chemical shift (ppm) and the ordinate shows the peak intensity.

FIG. 9 shows a solid state $^{13}$C NMR spectrum of the crystal form A of the compound (I) maleate salt obtained in Example 3. The abscissa shows the chemical shift (ppm) and the ordinate shows the peak intensity.

FIG. 10 shows a solid state $^{13}$C NMR spectrum of the crystal form B of the compound (I) maleate salt obtained in Example 4. The abscissa shows the chemical shift (ppm) and the ordinate shows the peak intensity.

FIG. 11 shows a solid state $^{13}$C NMR spectrum of the crystal of the compound (I) L-mandelate salt obtained in Example 5. The abscissa shows the chemical shift (ppm) and the ordinate shows the peak intensity.

FIG. 12 shows a solid state $^{13}$C NMR spectrum of the crystal of the compound (I) benzenesulfonate salt obtained in Example 6. The abscissa shows the chemical shift (ppm) and the ordinate shows the peak intensity.

FIG. 13 is a graph showing hygroscopicity of the crystal of the compound (I) hydrochloride salt obtained in Example 1. The abscissa shows the relative humidity and the ordinate shows the weight change.

FIG. 14 is a graph showing hygroscopicity of the crystal of the compound (I) hydrobromide salt obtained in Example 2. The abscissa shows the relative humidity and the ordinate shows the weight change.

FIG. 15 is a graph showing hygroscopicity of the crystal form A of the compound (I) maleate salt obtained in Example 3. The abscissa shows the relative humidity and the ordinate shows the weight change.

FIG. 16 is a graph showing hygroscopicity of the crystal form B of the compound (I) maleate salt obtained in Example 4. The abscissa shows the relative humidity and the ordinate shows the weight change.

FIG. 17 is a graph showing hygroscopicity of the crystal of the compound (I) L-mandelate salt obtained in Example 5. The abscissa shows the relative humidity and the ordinate shows the weight change.

FIG. 18 is a graph showing hygroscopicity of the crystal of the compound (I) benzenesulfonate salt obtained in Example 6. The abscissa shows the relative humidity and the ordinate shows the weight change.

FIG. 19 shows in vitro proliferation effects of wild-type and mutant ER-bearing MCF7 lines to clinical therapies 4-hydroxytamoxifen (4-OHT), raloxifene and fulvestrant, where phenotypic resistance observed in mutant-bearing lines relative to control lines to existing clinical compounds, whereby MCF7 cells engineered to overexpress various ERα$^{MUT}$ showed partial resistance to various endocrine therapies.

FIG. 20 is a graph showing antitumor and body weight effects of oral compound (I) in MCF7 xenograft bearing female Balb/c nude mice.

FIG. 21 is a graph showing antitumor and body weight effects of oral compound (I) in PDX-Y537S xenograft bearing athymic nude (Crl:NU(NCr)-Foxn1nu) female mice.

FIG. 22 is a graph showing the anti-tumor and body weight effects of the compound (I) in the ER+ WHIM20 PDX model bearing a homozygous Y537S mutation.

DESCRIPTION OF EMBODIMENTS

A salt of the compound (I) of the present invention, a crystal thereof, and production methods thereof will be described in detail.

As used herein, a "salt" refers to a chemical entity made up of the compound (I) as the basic component and a specific number of equivalents of an acid to the compound (I). Here, the term "a salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I, and an acid selected from the group consisting of hydrobromic acid, maleic acid, mandelic acid and benzenesulfonic acid" is used for the same meaning as "a salt of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide represented by the formula I formed with an acid selected from the group consisting of hydrobromic acid, maleic acid, mandelic acid and benzenesulfonic acid".

Examples of a "salt" used herein include salts with organic carboxylic acids, with organic sulfonic acids and with inorganic acids, and in particular, pharmaceutically acceptable salts are preferred.

Examples of organic carboxylic acids include acetic acid, oxalic acid, maleic acid, mandelic acid, tartaric acid, fumaric acid, citric acid, malonic acid, succinic acid and malic acid. Preferred examples of organic carboxylic acids include maleic acid, mandelic acid (preferably L-mandelic acid), tartaric acid and malonic acid.

Examples of organic sulfonic acids include methanesulfonic acid, trifluoromethane-sulfonic acid, ethanesulfonic acid, benzenesulfonic acid, p-toluenesulfonic acid and camphorsulfonic acid. Preferred examples of organic sulfonic acids include methanesulfonic acid, benzenesulfonic acid and p-toluenesulfonic acid.

Examples of inorganic acids include hydrofluoric acid, hydrochloric acid, hydrobromic acid, hydroiodic acid, sulfuric acid, nitric acid, perchloric acid, phosphoric acid, carbonic acid and bicarbonic acid. Preferred examples of inorganic acids include hydrochloric acid, hydrobromic acid, sulfuric acid, nitric acid and phosphoric acid.

A salt of the compound (I) may also be a solvate. As used herein, a solvate of the salt of compound (I) means a solid formed from the salt of the compound (I) together with solvent molecules. Examples of the solvent in the solvate include: a ketone solvent such as acetone, methyl ethyl ketone or cyclohexanone; an ester solvent such as ethyl acetate or methyl acetate; an ether solvent such as 1,2-dimethoxyethane or methyl-tert-butyl ether; an alcohol solvent such as methanol, ethanol, 1-propanol or isopropanol; a polar solvent such as N-methyl-2-pyrrolidone, N,N-dimethylformamide or dimethyl sulfoxide; and water.

As used herein, a "crystal" refers to a crystal of the salt of compound (I). Accordingly, a crystal of hydrochloride salt of compound (I), for example, means a crystal of the salt formed between compound (I) and hydrochloric acid.

Examples of crystals preferred herein include:

(a) a crystal of hydrochloride salt of compound (I), having a diffraction peak at a diffraction angle (2θ±0.2°) of 18.1° in a powder X-ray diffractometry;

(b) a crystal of hydrochloride salt of compound (I), having diffraction peaks at diffraction angles (2θ±0.2°) of 6.1°, 11.8° and 18.1° in a powder X-ray diffractometry;

(c) a crystal of hydrochloride salt of compound (I), having diffraction peaks at diffraction angles (2θ±0.2°) of 6.1°, 11.8°, 16.8°, 18.1° and 19.5° in a powder X-ray diffractometry;

(d) a crystal of hydrochloride salt of compound (I), having one or more diffraction peaks at diffraction angles (2θ±0.2°) of 6.1°, 11.8°, 14.9°, 16.8°, 18.1°, 19.1°, 19.5°, 21.7°, 25.9° and 27.4° in a powder X-ray diffractometry;

(e) a crystal of hydrobromide salt of compound (I), having a diffraction peak at a diffraction angle (2θ±0.2°) of 18.7° in a powder X-ray diffractometry;

(f) a crystal of hydrobromide salt of compound (I), having diffraction peaks at diffraction angles (2θ±0.2°) of 6.2°, 18.7° and 22.5° in a powder X-ray diffractometry;

(g) a crystal of hydrobromide salt of compound (I), having diffraction peaks at diffraction angles (2θ±0.2°) of 6.2°, 11.7°, 18.7°, 20.4° and 22.5° in a powder X-ray diffractometry;

(h) a crystal of hydrobromide salt of compound (I), having one or more diffraction peaks at diffraction angles (2θ±0.2°) of 6.2°, 11.7°, 12.5°, 16.5°, 17.6°, 18.7°, 20.4°, 21.4°, 22.5° and 27.1° in a powder X-ray diffractometry;

(i) a crystal form A of maleate salt of compound (I), having a diffraction peak at a diffraction angle (2θ±0.2°) of 24.9° in a powder X-ray diffractometry;

(j) a crystal form A of maleate salt of compound (I), having diffraction peaks at diffraction angles (2θ±0.2°) of 17.9°, 22.9° and 24.9° in a powder X-ray diffractometry;

(k) a crystal form A of maleate salt of compound (I), having diffraction peaks at diffraction angles (2θ±0.2°) of 16.7°, 17.9°, 21.2°, 22.9° and 24.9° in a powder X-ray diffractometry;

(l) a crystal form A of maleate salt of compound (I), having one or more diffraction peaks at diffraction angles (2θ±0.2°) of 4.9°, 9.8°, 16.1°, 16.7°, 17.9°, 19.4°, 21.2°, 22.9°, 24.9° and 30.4° in a powder X-ray diffractometry;

(m) a crystal form B of maleate salt of compound (I), having a diffraction peak at a diffraction angle (2θ±0.2°) of 22.3° in a powder X-ray diffractometry;

(n) a crystal form B of maleate salt of compound (I), having diffraction peaks at diffraction angles (2θ±0.2°) of 14.8°, 20.2° and 22.3° in a powder X-ray diffractometry;

(o) a crystal form B of maleate salt of compound (I), having diffraction peaks at diffraction angles (2θ±0.2°) of 14.8°, 20.2°, 22.3° and 26.5° in a powder X-ray diffractometry;

(p) a crystal form B of maleate salt of compound (I), having one or more diffraction peaks at diffraction angles (2θ±0.2°) of 14.8°, 15.8°, 17.1°, 17.5°, 20.2°, 20.9°, 22.3°, 24.6°, 26.5° and 28.5° in a powder X-ray diffractometry;

(q) a crystal of L-mandelate salt of compound (I), having a diffraction peak at a diffraction angle (2θ±0.2°) of 18.3° in a powder X-ray diffractometry;

(r) a crystal of L-mandelate salt of compound (I), having diffraction peaks at diffraction angles (2θ±0.2°) of 5.1°, 10.3° and 18.3° in a powder X-ray diffractometry;

(s) a crystal of L-mandelate salt of compound (I), having diffraction peaks at diffraction angles (2θ±0.2°) of 5.1°, 8.8°, 10.3°, 16.9° and 18.3° in a powder X-ray diffractometry;

(t) a crystal of L-mandelate salt of compound (I), having one or more diffraction peaks at diffraction angles (2θ±0.2°) of 5.1°, 8.8°, 10.3°, 13.8°, 16.9°, 18.3°, 19.2°, 21.2°, 22.8° and 24.6° in a powder X-ray diffractometry;

(u) a crystal of benzenesulfonate salt of compound (I), having a diffraction peak at a diffraction angle (2θ±0.2°) of 9.5° in a powder X-ray diffractometry;

(v) a crystal of benzenesulfonate salt of compound (I), having diffraction peaks at diffraction angles (2θ±0.2° of 5.2°, 9.5° and 10.5° in a powder X-ray diffractometry;

(w) a crystal of benzenesulfonate salt of compound (I), having diffraction peaks at diffraction angles (2θ±0.2°) of 5.2°, 9.5°, 10.5°, 21.4° and 24.4° in a powder X-ray diffractometry;

(x) a crystal of benzenesulfonate salt of compound (I), having one or more diffraction peaks at diffraction angles (2θ±0.2°) of 5.2°, 9.5°, 10.5°, 12.1°, 15.4°, 17.4°, 20.3°, 21.4°, 23.1° and 24.4° in a powder X-ray diffractometry;

(aa) a crystal of hydrochloride salt of compound (I), having peaks at chemical shifts (±0.5 ppm) of 164.3 ppm, 162.2 ppm and 111.9 ppm in a solid state $^{13}$C NMR spectrum;

(bb) a crystal of hydrochloride salt of compound (I), having peaks at chemical shifts (±0.5 ppm) of 164.3 ppm, 162.2 ppm, 148.6 ppm, 138.9 ppm and 111.9 ppm in a solid state $^{13}$C NMR spectrum;

(cc) a crystal of hydrochloride salt of compound (I), having peaks at chemical shifts (±0.5 ppm) of 164.3 ppm, 162.2 ppm, 148.6 ppm, 138.9 ppm, 136.8 ppm, 134.0 ppm, 111.9 ppm, 61.5 ppm, 38.4 ppm and 34.4 ppm in a solid state $^{13}$C NMR spectrum;

(dd) a crystal of hydrobromide salt of compound (I), having peaks at chemical shifts (±0.5 ppm) of 164.5 ppm, 162.2 ppm and 111.7 ppm in a solid state $^{13}$C NMR spectrum;

(ee) a crystal of hydrobromide salt of compound (I), having peaks at chemical shifts (±0.5 ppm) of 164.5 ppm, 162.2 ppm, 148.6 ppm, 139.3 ppm and 111.7 ppm in a solid state $^{13}$C NMR spectrum;

(ff) a crystal of hydrobromide salt of compound (I), having peaks at chemical shifts (±0.5 ppm) of 164.5 ppm, 162.2 ppm, 148.6 ppm, 139.3 ppm, 135.8 ppm, 134.0 ppm, 111.7 ppm, 60.9 ppm, 39.0 ppm and 34.5 ppm in a solid state $^{13}$C NMR spectrum;

(gg) a crystal form A of maleate salt of compound (I), having peaks at chemical shifts (±0.5 ppm) of 169.6 ppm, 107.3 ppm and 50.3 ppm in a solid state $^{13}$C NMR spectrum;

(hh) a crystal form A of maleate salt of compound (I), having peaks at chemical shifts (±0.5 ppm) of 169.6 ppm, 168.0 ppm, 107.3 ppm, 50.3 ppm and 46.9 ppm in a solid state $^{13}$C NMR spectrum;

(ii) a crystal form A of maleate salt of compound (I), having peaks at chemical shifts (±0.5 ppm) of 169.6 ppm, 168.0 ppm, 134.2 ppm, 117.1 ppm, 112.0 ppm, 107.3 ppm, 63.6 ppm, 50.3 ppm, 46.9 ppm and 36.1 ppm in a solid state $^{13}$C NMR spectrum;

(jj) a crystal form B of maleate salt of compound (I), having peaks at chemical shifts (±0.5 ppm) of 171.4 ppm, 108.6 ppm and 48.8 ppm in a solid state $^{13}$C NMR spectrum;

(kk) a crystal form B of maleate salt of compound (I), having peaks at chemical shifts (±0.5 ppm) of 171.4 ppm, 167.1 ppm, 108.6 ppm, 48.8 ppm and 44.5 ppm in a solid state $^{13}$C NMR spectrum;

(ll) a crystal form B of maleate salt of compound (I), having peaks at chemical shifts (±0.5 ppm) of 171.4 ppm, 167.1 ppm, 133.3 ppm, 117.8 ppm, 112.8 ppm, 108.6 ppm, 63.1 ppm, 48.8 ppm, 44.5 ppm and 38.3 ppm in a solid state $^{13}$C NMR spectrum;

(mm) a crystal of L-mandelate salt of compound (I), having peaks at chemical shifts (±0.5 ppm) of 165.9 ppm, 160.7 ppm and 110.5 ppm in a solid state $^{13}$C NMR spectrum;

(nn) a crystal of L-mandelate salt of compound (I), having peaks at chemical shifts (±0.5 ppm) of 176.8 ppm, 165.9 ppm, 160.7 ppm, 147.7 ppm and 110.5 ppm in a solid state $^{13}$C NMR spectrum;

(oo) a crystal of L-mandelate salt of compound (I), having peaks at chemical shifts (±0.5 ppm) of 176.8 ppm, 165.9 ppm, 160.7 ppm, 147.7 ppm, 141.2 ppm, 110.5 ppm, 76.3 ppm, 48.6 ppm, 37.2 ppm and 34.1 ppm in a solid state $^{13}$C NMR spectrum;

(pp) a crystal of benzenesulfonate salt of compound (I), having peaks at chemical shifts (±0.5 ppm) of 163.0 ppm, 147.2 ppm and 145.0 ppm in a solid state $^{13}$C NMR spectrum;

(qq) a crystal of benzenesulfonate salt of compound (I), having peaks at chemical shifts (±0.5 ppm) of 163.0 ppm, 160.9 ppm, 147.2 ppm, 145.0 ppm and 109.3 ppm in a solid state $^{13}$C NMR spectrum; and (rr) a crystal of benzenesulfonate salt of compound (I), having peaks at chemical shifts (±0.5 ppm) of 163.0 ppm, 160.9 ppm, 147.2 ppm, 145.0 ppm, 140.2 ppm, 133.4 ppm, 109.3 ppm, 47.1 ppm, 37.3 ppm and 34.8 ppm in a solid state $^{13}$C NMR spectrum.

The peaks in a powder X-ray diffractometry, described above, are characteristic for each of the crystal of hydrochloride salt of compound (I), the crystal of hydrobromide salt of compound (I), the crystal form A of maleate salt of compound (I), the crystal form B of maleate salt of compound (I), the crystal of L-mandelate salt of compound (I), and the crystal of benzenesulfonate salt of compound (I).

Generally, errors in diffraction angles (2θ) within the range of ±0.2° may arise in powder X-ray diffractometry, and thus the above-described values of diffraction angles need to be considered to include values within the range of approximately ±0.2°. Included in the present invention are, therefore, not only crystals with peaks at exactly the same diffraction angles in powder X-ray diffractometry, but also crystals with peaks within an error range of approximately ±0.2° of the diffraction angles. Hence, "having a diffraction peak at a diffraction angle (2θ±0.2°) of 18.1°" as used herein, for example, means "having a diffraction peak at a diffraction angle (2θ) of 17.9° to 18.3°". The same is also applied to other diffraction angles.

Generally, peak intensities and half-value widths of diffraction angles (2θ) in powder X-ray diffraction are different for each measurement because of differences in measurement conditions and dispersions of size and shape of each particle of powder crystal and not always stable even though forms of crystals are same. Therefore, in case of comparing a powder X-ray diffraction pattern, when diffraction angles (2θ) are the same but peak intensities, relative peak intensities and half-value widths are different, those differences does not imply that the measured forms of crystals differ from each other. Thus, a crystal of salt having a powder X-ray diffraction pattern, which has aforementioned differences with respect to characteristic diffraction peaks of a certain crystal of salt according to the present invention, means that the crystal has the same crystal form of the crystal of salt according to the present invention.

As used herein, "having a powder X-ray diffraction pattern substantially the same as the powder X-ray diffraction pattern shown in FIG. 1" means it includes not only the case of having exactly the same powder X-ray diffraction pattern as shown in FIG. 1, but also the case that peak intensities, relative peak intensities and half-value widths are different, or the case of having the characteristic peaks within an error range of approximately ±0.2° of the diffraction angles. Thus every crystal having such the powder X-ray diffraction pattern means that the crystal is identical to the crystal according to the present invention.

The peaks in solid state $^{13}C$ NMR spectrum, described above, are characteristic for each of the crystal of hydrochloride salt of compound (I), the crystal of hydrobromide salt of compound (I), the crystal form A of maleate salt of compound (I), the crystal form B of maleate salt of compound (I), the crystal of L-mandelate salt of compound (I), and the crystal of benzenesulfonate salt of compound (I).

As used herein, "having peaks at chemical shifts of 164.3 ppm, 162.2 ppm and 111.9 ppm" means "having peaks each substantially equivalent to the peaks at chemical shifts of 164.3 ppm, 162.2 ppm and 111.9 ppm, when solid state $^{13}C$ NMR spectrometry is performed under a conventional measurement condition or substantially the same condition as in the present specification".

When determining whether "having peaks substantially equivalent to" or not, the above-described values of the chemical shifts need to be considered to include values within the range of approximately ±0.5 ppm since generally errors in chemical shifts (ppm) within the range of ±0.5 ppm may arise in a solid state $^{13}C$ NMR spectrum. Included in the present invention are, therefore, not only crystals with exactly the same chemical shifts in a solid state $^{13}C$ NMR spectrum, but also crystals with chemical shifts within an error range of approximately ±0.5 ppm. Hence, "having a peak at chemical shift of 164.3 ppm" as used herein, for examples, means "having a peak at a chemical shift of 163.8 ppm to 164.8 ppm". The same is also applied to other chemical shifts in solid state $^{13}C$ NMR spectra.

As used herein, "having a solid state $^{13}C$ NMR spectrum substantially the same as the solid state $^{13}C$ NMR spectrum shown in FIG. 7" means it includes not only the case of having exactly the same solid state $^{13}C$ NMR spectrum as shown in FIG. 7, but also the case that peak intensities are different, or the case of having the characteristic peaks within an error range of approximately ±0.5 ppm. Thus every crystal having such the solid state $^{13}C$ NMR spectrum means that the crystal is identical to the crystal according to the present invention.

Methods for producing a salt of the compound (I) and a crystal thereof will be described in detail.

(Production of Compound (I))

Compound (I) can be synthesized as described specifically in Production Example 1 below.

(Method for Producing a Salt of the Compound (I))

A salt of the compound (I) can be obtained by a conventional method for producing a salt. Specifically, it can be produced, for example, by suspending or dissolving compound (I) in a solvent, with heating if necessary, then by adding an acid to the obtained suspension or solution and by stirring or leaving the resultant suspension or solution for several minutes to several days at room temperature or with ice-bath cooling. A salt of the compound (I) may be obtained as crystals or amorphous substances according to the production methods. Examples of the solvents to be used in these methods include alcohol solvents such as ethanol, 1-propanol and isopropanol; acetonitrile; ketone solvents such as acetone and 2-butanone; ester solvents such as ethyl acetate; saturated hydrocarbon solvents such as hexane and heptane; ether solvents such as t-butyl methyl ether or water. Each of these solvents may be used alone, or two or more may be mixed and used.

(Method for Producing a Crystal of the Salt of Compound (I))

A crystal of the salt of compound (I) may be produced by the above-mentioned methods for producing a salt of the compound (I), or by heat-dissolving a salt of the compound (I) in a solvent and crystallizing it through cooling with stirring.

A salt of the compound (I) to be used in the crystallization may be in any form: it may be a solvate, a hydrate, an anhydrate, an amorphous substance, a crystalline substance (including those consisting of a plurality of crystalline polymorphs) or a combination thereof.

Examples of the solvents to be used in the crystallization include alcohol solvents such as methanol, ethanol, isopropanol and 1-propanol; acetonitrile; amide solvents such as N,N-dimethylformamide; ester solvents such as ethyl acetate; saturated hydrocarbon solvents such as hexane and heptane; ketone solvents such as acetone and 2-butanone; ether solvents such as t-butyl methyl ether or water. Furthermore, each of these solvents may be used alone, or two or more may be mixed and used.

The amount of the solvent to be used may be suitably selected, provided that the lower limit is the amount with which the free form of compound (I) or the salt thereof is dissolved by heating or the suspension can be stirred, and that the upper limit is the amount with which the yield of the crystal is not significantly reduced.

A seed crystal (e.g., the crystal of the desired salt of compound (I)) may be added or may not be added during the crystallization. The temperature at which the seed crystal is added is not particularly limited, but is preferably 0 to 80° C.

As the temperature to be employed when the salt of compound (I) is dissolved by heating, that at which compound (I) dissolves may be suitably selected depending on the solvent, but it is preferably within the range between the temperature at which the recrystallization solvent starts to reflux and 50° C., and more preferably 65 to 55° C.

Cooling during the crystallization could give substances containing different forms of crystals (polymorphism) in the case of rapid cooling. It is therefore desirable to perform the cooling while controlling the cooling rate as appropriate based on the consideration of its effect on the quality, grain size and the like of the crystal. Preferred is, for example, cooling at a cooling rate of 40 to 5° C./hour. More preferred is cooling at a cooling rate of, for example, 25 to 5° C./hour.

Furthermore, the final crystallization temperature may be selected suitably for the yield, quality and the like of the crystal, but is preferably 30 to −25° C.

The target crystal can be obtained by isolating the formed crystal through a conventional filtration procedure, washing the filtered-off crystal with a solvent if necessary, and further drying it. As the solvent to be used for washing the crystal, the same solvent as in the crystallization can be used.

Furthermore, each of these solvents may be used alone, or two or more may be mixed and used. Preferably, it is, for example, acetone, 2-butanone, ethyl acetate, t-butyl methyl ether, hexane or a mixed solvent of hexane/2-butanone.

The crystal isolated through the filtration procedure may be dried appropriately by leaving it in air or under nitrogen flow, or by heating.

As the drying time, the time until the amount of residual solvent becomes less than the predefined amount may be selected as appropriate depending on the amount of production, the drying apparatus, the drying temperature and the like. Furthermore, drying may be performed under airflow or under reduced pressure. The degree of pressure reduction may be selected as appropriate depending on the amount of production, the drying apparatus, the drying temperature and the like. The obtained crystal may be left in air as required after drying.

A pharmaceutical composition of the present invention could be prepared by mixing pharmaceutically acceptable additives with the salt of compound (I) or the crystal thereof. A pharmaceutical composition of the present invention could be prepared according to the known method such as a method described in the general rules for preparations of the Japanese Pharmacopoeia 17th edition.

A pharmaceutical composition of the present invention could be administered to patients appropriately depending on the dosage form.

A pharmaceutical composition of the present invention has usability as a therapeutic agent for treating cancers since the salt of compound (I) or the crystal thereof can potently suppress the growth of both wild-type (WT) and ER α-mutant positive tumors. Examples of cancers include breast cancer, uterine endometrial, ovarian carcinoma, sarcoma, thyroid carcinoma, prostate, lung adenocarcinoma, and hepato-cellular carcinoma. Preferred example of cancers includes breast cancer. More preferred example of cancers includes ER-positive breast cancer.

The dosage of the salt of compound (I) or the crystal thereof varies depending on the extent of the symptom, age, gender, body weight, dosage form, the type of the salt, the specific type of the disease and the like. In the case of adults, typically, about 30 μg to 10 g, preferably 100 μg to 5 g, and more preferably 100 μg to 1 g per day is orally administered, or about 30 μg to 1 g, preferably 100 μg to 500 mg, and more preferably 100 μg to 300 mg per day is administered by injection, in each case, in a single dose or in divided doses.

EXAMPLE

Hereinafter, the present invention will be described in detail with the production examples and examples. However, the present invention is not intended to be limited by these examples.

The following abbreviations may be used herein:
ACN: Acetonitrile
BOC: tert-Butyloxycarbonyl
CAN: Ceric ammonium nitrate
Conc.: concentrated
$Cs_2CO_3$: Cesium carbonate
DABCO: 1, 4-Diazabicyclo[2.2.2]octane
DCM: Dichloromethane
DHP: Dihydropyran
DIPEA: N, N-diisopropylethylamine, Hunig's base
DMA: Dimethylacetamide
DMF: Dimethylformamide
DMSO: Dimethylsulfoxide
DPEphos: (Oxydi-2, 1-phenylene)bis(diphenylphosphine)
EDCI.HCl: N-(3-Dimethylaminopropyl)-N-ethylcarbodiimide hydrochloride
EtOH: Ethanol
EtOAc: Ethyl acetate
$Et_3N$: Triethylamine
Ex.: Example
h: Hours
HATU: 1-[Bis(dimethylamino)methylene]-1H-1,2,3-triazolo[4,5-b]pyridinium 3-oxid hexafluorophosphate
HCl: Hydrochloric acid
HMPA: Hexamethylphosphoramide
HPLC: High-performance liquid chromatography
$H_2SO_4$: Sulfuric acid
IPA: Isopropyl alcohol
$K_2CO_3$: Potassium carbonate
KOH: Potassium hydroxide
LCMS: Liquid chromatography-mass spectrometry
MeOH: Methanol
$Na_2CO_3$: Sodium carbonate
NBS: n-Bromosuccinimide
nBuLi: n-Butyllithium
$NH_4Cl$: Ammonium chloride
$NH_4OH$: Ammonium hydroxide
NMR: nuclear magnetic resonance
on or o.n.: overnight
Pd/C: Palladium (0) on carbon
$Pd_2(dba)_3$: Tris(dibenzylideneacetone)dipalladium(0)
PPTS: Pyridinium p-toluenesulfonate
PTSA: p-Toluenesulfonic acid
RT or r.t.: room temperature
TBAF: Tetrabutylammonium fluoride
TEA: Triethylamine
TFA: Trifluoroacetic acid
THF: Tetrahydrofuran
TLC: Thin-layer chromatography
Pt/C: Platinum (0) on carbon
$^1H$ NMR: proton nuclear magnetic resonance The coupling constant is recorded in hertz (Hz). The abbreviations of splitting patterns are as follows:
s: singlet, d: doublet, t: triplet, q: quartet, m: multiplex, bs: broad singlet, br s: broad singlet, dd: doublet of doublets, dt: doublet of triplets, br d: broad doublet, br t: broad triplet Powder X-Ray Diffractometry The powder X-ray diffractometry of the crystal obtained by the method described in the following Examples was analyzed under the following measurement conditions.
Measurement Conditions
Apparatus: RINT TTR-III (Rigaku)
Sample pan: aluminum
X-ray: Cu K alpha
Detection: scintillation counter
Tube voltage: 50 kV
Tube current: 300 mA
Slit: divergence slit 0.5 mm (Height limiting slit 2 mm), scattering slit open, receiving slit open
Scan speed: 5°/minute
Step size: 2θ=0.02°
Scan range: 2θ=3° to 35°
Solid State $^{13}C$ NMR Spectrometry The solid state $^{13}C$ NMR spectrum of the crystal obtained by the method described in the following Examples was measured under the following measurement conditions
Measurement Conditions
Apparatus: AVANCE400 MHz (Bruker)

Measurement temperature: room temperature (22° C.)

Reference material: glycine (external standard: 176.03 ppm)

Measured nucleus: $^{13}C$ (100.6131 MHz)

Number of transients: 2048 (for the crystal of hydrochloride salt, the crystal of hydrobromide salt, the crystal form B of maleate salt, the crystal of L-mandelate salt and the crystal of benzenesulfonate salt), 12288 (for the crystal form A of maleate salt)

Pulse repetition time: 4 seconds

Contact time: 1 m second

Rotational speed: 5000 Hz

Pulse mode: TOSS measurement

Hygroscopicity

The crystal obtained by the method described in the following Examples was weighed into a sampling cup and then the sampling cup was placed inside an isothermal chamber at 25° C. The relative humidity (RH) was controlled from 0% to 95% using a gravimetric vapor sorption system and the weight change of the sample at each stage was measured under the condition described below.

Measurement Conditions

Sample temperature: 25° C.

First stage RH: 0%

Stop stage RH: 95%

Step number: 39 (0, 5, 10, 15, 20, 25, 30, 35, 40, 45, 50, 55, 60, 65, 70, 75, 80, 85, 90, 95, 90, 85, 80, 75, 70, 65, 60, 55, 50, 45, 40, 35, 30, 25, 20, 15, 10, 5, 0)

Equilibrium criterion: 0.002 wt % in 1 minute

Max equilibrium time: 360 minutes

Production Example 1

Preparation of (E)-N,N-dimethyl-4-((2-((5-((Z)-4,4,4-trifluoro-1-(3-fluoro-1H-indazol-5-yl)-2-phenyl-but-1-en-1-yl)pyridin-2-yl)oxy)ethyl)amino)but-2-enamide (compound (I))

Reference Production Example 1a

To a stirred solution of 5-bromo-1H-indazole (23.5 mmol) in dry dichloromethane (50 mL) at 23° C. was added dihydro pyran (9.9 g, 118 mmol) followed by addition of pyridinium p-toluene sulfonate (0.6 g, 2.4 mmol). The resulting mixture was stirred at room 23° C. temperature for 16 h. Upon completion by TLC, the reaction mixture was quenched with water (50 mL) and extracted with dichloromethane (2×100 mL). The combined organic extracts were washed with water, brine, dried over sodium sulphate and concentrated. The crude material was purified by column chromatography over 230-400 mesh silica using 4-5% ethyl acetate in hexane to afford 5-bromo-1-(tetrahydro-2H-pyran-2-yl)-1H-indazole (20 mmol, 86%) as a pale yellow oil.

Reference Production Example 1b

[Chem.27]

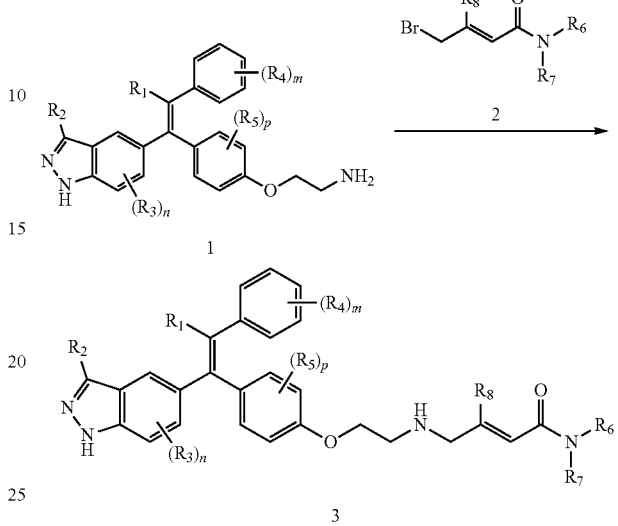

In the above scheme, $R_1$ is selected from the group consisting of methyl, ethyl, cyclobutyl, cyclopropyl, propyl, isopropyl, —$CH_2CF_3$, —$CH_2CH_2F$, and —$CH_2CH_2C$; $R_2$ is selected from the group consisting of H and F; n is 0-1; $R_3$ is F when n=1; m is 0-2; $R_4$ are the same or different and are independently selected from the group consisting of F, $CF_3$, Cl, isopropyl, —$OCH_3$, —$OCHF_2$, —$OCF_3$, ethyl and methyl; p is 0-1; $R_5$ is F when p=1; $R_6$ and $R_7$ are the same or different and are independently selected from the group consisting of methyl, ethyl, propyl, —$CH_2CH_2OH$ and

[Chem.28]

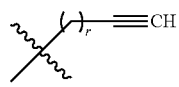

wherein r is 1 or 2; or, wherein $R_6$ and $R_7$ form a 4-6 membered heterocyclic ring with the N to which they are attached, wherein said heterocyclic ring optionally includes an oxygen atom, and wherein said heterocyclic ring is optionally substituted with F, or —$CH_2F$; and $R_8$ is selected from the group consisting of H and —$CH_3$.

To a stirred solution of 1 (1.24 mmol) in DMF (5 mL) was added at 0° C., (E)-4-bromo-N,N-dimethylbut-2-enamide (2, 1.24 mmol) and DIPEA (0.321 g, 2.49 mmol). The reaction mixture was stirred for 12-48 h at 23° C., was diluted with cold water (50 mL) and extracted with dichloromethane. The organic layer was washed with water followed by brine, dried over anhydrous sodium sulphate and concentrated under reduced pressure to give a crude mixture of 3.

Reference Production Example 1c

To a stirred solution of 4-iodophenol (227 mmol) in DMF (750 mL) was added potassium carbonate (188 g, 1.363 mol)

and stirred for 30 min at 23° C., to the above mixture tert-butyl (2-bromoethyl)carbamate (71.27 g, 318 mmol) was added. The contents were stirred at 70° C. for 12 h. After completion of reaction, reaction mixture was poured onto ice cold water, solid separated was filtered and dried under reduced pressure to obtain desired compound tert-butyl (2-(4-iodophenoxy)-ethyl)carbamate as an off-white solid (220 mmol, 97%).

Production Example 1a

Synthesis of 5-bromo-1-(tetrahydro-2H-pyran-2-yl)-1H-indazole

[Chem.29]

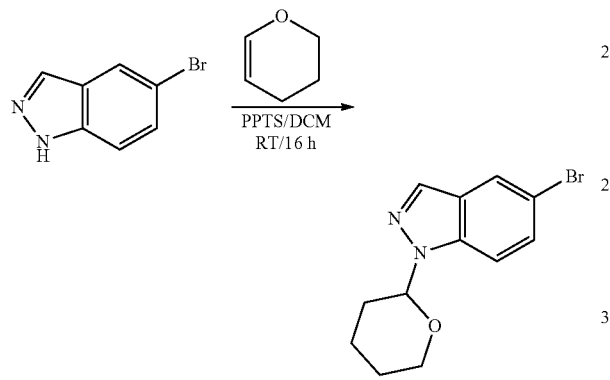

The reaction was carried out according to Reference Production Example 1a. The crude material was purified by column chromatography over 230-400 mesh silica using 4-5% ethyl acetate in hexane to afford the title compound of Production Example 1a (12.6 g, 86%) as a pale yellow oil.

Production Example 1b

Synthesis of 5-bromo-3-fluoro-1H-indazole

[Chem. 30]

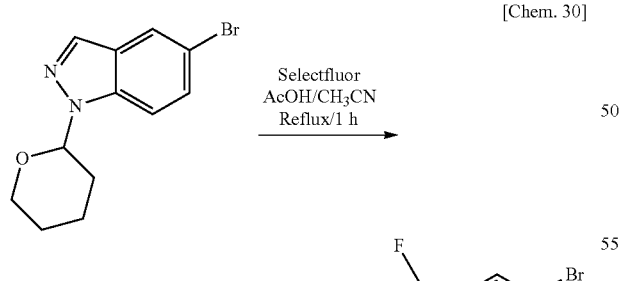

To a stirred solution of 5-bromo-1-(tetrahydro-2H-pyran-2-yl)-1H-indazole (10 g, 35.7 mmol, as prepared in Production Example 1a) in 100 mL of acetonitrile, were added acetic acid (4 mL) and selectfluor (25.2 g, 71.4 mmol) at room temperature. Reaction mixture was refluxed for 1 h. Upon completion by TLC, the reaction mixture was diluted with water (100 mL) and extracted with ethyl acetate (200 mL). The combined organic extracts were washed with water, brine, dried over anhydrous sodium sulphate and concentrated under reduced pressure. The crude product was purified over 230-400 mesh silica column chromatography using 1% ethyl acetate in n-hexane to afford 5-bromo-3-fluoro-1H-indazole (6 g, 78%) as a brown oil.

Production Example 1c

Synthesis of 5-bromo-3-fluoro-1-(tetrahydro-2H-pyran-2-yl)-1H-indazole

[Chem. 31]

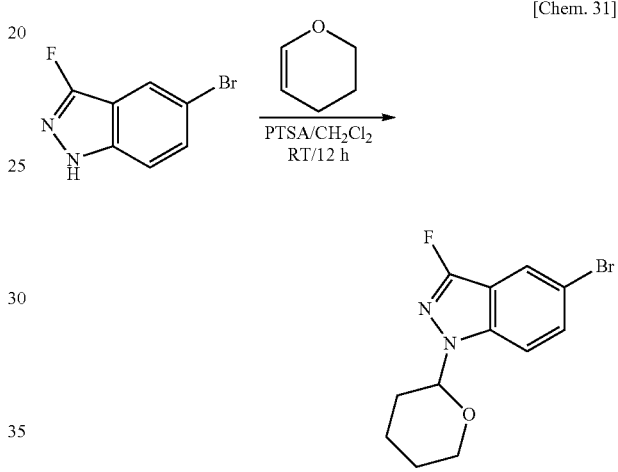

The reaction was carried out according to Reference Production Example 1a to give a crude product, which was purified over 230-400 mesh silica column chromatography using 1% ethyl acetate in n-hexane to afford the title compound of Production Example 1c (5 g, 60%) as a brown oil.

Production Example 1d

Synthesis of 3-fluoro-1-(tetrahydro-2H-pyran-2-yl)-5-((trimethylsilyl)ethynyl)-1H-indazole

[Chem. 32]

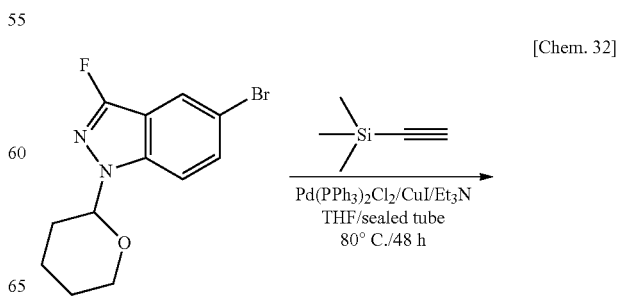

-continued

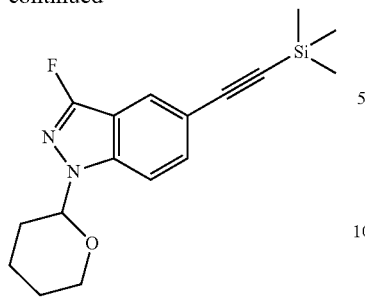

To a stirred solution of 5-bromo-3-fluoro-1-(tetrahydro-2H-pyran-2-yl)-1H-indazole (4.5 g, 15 mmol, as prepared in Production Example 1c) in 35 mL of THF:Et$_3$N (5:1) in a sealed tube, were added copper iodide (0.288 g, 1.5 mmol) at room temperature. This mixture was degassed with three vacuum/N$_2$ cycles, and were added ethynyltrimethylsilane (2.22 g, 22 mmol) followed by Pd(PPh$_3$)$_2$Cl$_2$ (0.5 g, 0.7 mmol). The pressure tube was sealed and heated at 80° C. for 48 h. Upon completion by TLC, the reaction mixture was diluted with water (250 mL) and extracted with EtOAc (2×100 mL). The combined organic extracts were washed with water, brine, dried over anhydrous sodium sulphate and concentrated under reduced pressure. The crude product was purified by combi-flash using 5% EtOAc in n-hexane to afford 3-fluoro-1-(tetrahydro-2H-pyran-2-yl)-5-((trimethylsilyl)ethynyl)-1H-indazole (3.2 g, 72%).

Production Example 1e

Synthesis of 5-ethynyl-3-fluoro-1-(tetrahydro-2H-pyran-2-yl)-1H-indazole

[Chem. 33]

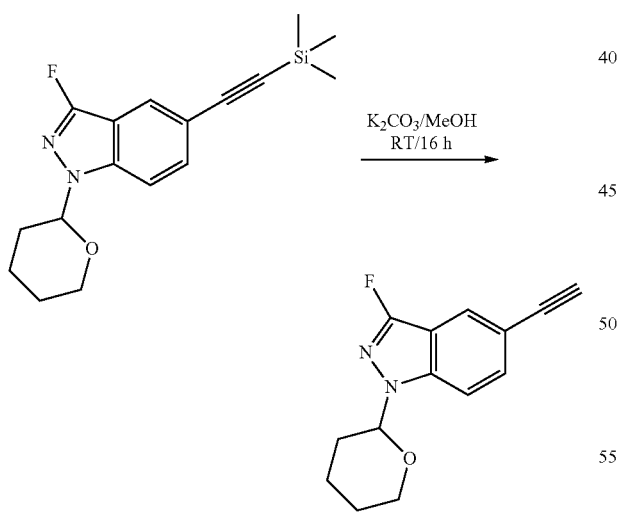

To a stirred solution of 3-fluoro-1-(tetrahydro-2H-pyran-2-yl)-5-((trimethylsilyl)ethynyl)-1H-indazole (3.2 g, 10 mmol) in methanol 32 mL was added potassium carbonate (0.151 g, mmol), reaction mixture was stirred for 16 h at room temperature. After completion of reaction, reaction mixture was diluted with ethyl acetate and the organic layer was washed with water followed by brine. The organic layer was dried over anhydrous Na$_e$ SO$_4$ and concentrated under reduced pressure to obtain the title compound of Production Example 1e (2.8 g, crude).

Production Example 1f

Synthesis of 3-fluoro-1-(tetrahydro-2H-pyran-2-yl)-5-(4,4,4-trifluorobut-1-yn-1-yl)-1H-indazole

[Chem. 34]

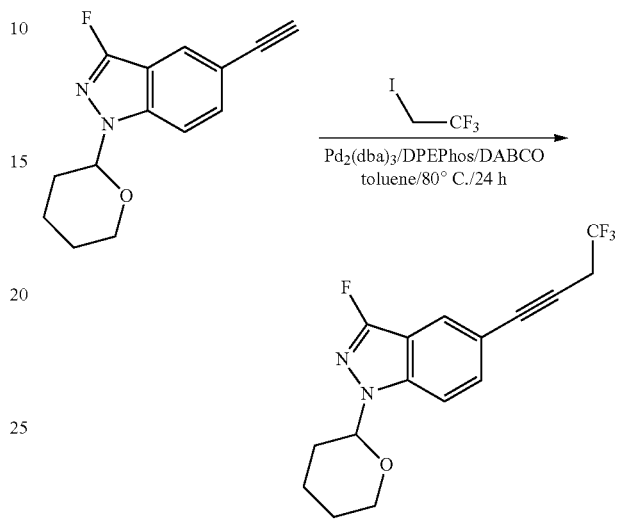

To a stirred solution of 5-ethynyl-3-fluoro-1-(tetrahydro-2H-pyran-2-yl)-1H-indazole (2.6 g, 10.6 mmol) in 20 mL of toluene, were added 1,1,1-trifluoro-2-iodoethane (4.47 g, 21.3 mmol) at room temperature. This mixture was degassed with three vacuum/N$_2$ cycles, and were added Pd$_2$(dba)$_3$ (0.487 g, 0.5 mmol) followed by DPEphos (1.14 g, 2.1 mmol) and DABCO (2.39 g, 21.3 mmol). Reaction mixture was heated at 80° C. for 24 h. Upon completion by TLC, the reaction mixture was diluted with water (250 mL) and extracted with EtOAc (2×100 mL). The combined organic extracts were washed with water, brine, dried over anhydrous sodium sulphate and concentrated under reduced pressure. The crude product was purified by column chromatography using 5% EtOAc in n-hexane to afford 3-fluoro-1-(tetrahydro-2H-pyran-2-yl)-5-(4,4,4-trifluorobut-1-yn-1-yl)-1H-indazole (1.6 g, 46%).

Production Example 1g

Synthesis of (E)-4-bromobut-2-enoic acid

[Chem.35]

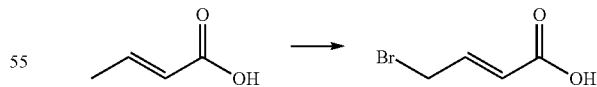

To a stirred solution of (E)-but-2-enoic acid (10.0 g, 116.0 mmol) in benzene (150 mL) was added N-Bromosuccinamide (31.4 g, 120.0 mmol) followed by Benzoyl peroxide (0.200 g, 1.4 mmol) at 23° C. The reaction mixture was heated to reflux for 4 h, which resulted in precipitation of succinamide crystals. The crystals were filtered off and the filtrate was concentrated. The crude was recrystallized with minimum amount of hexane and washed with hexane to afford (E)-4-bromobut-2-enoic acid (6.97 g, 37%) as a white solid.

Production Example 1h

Synthesis of (E)-4-bromo-N,N-dimethylbut-2-enamide

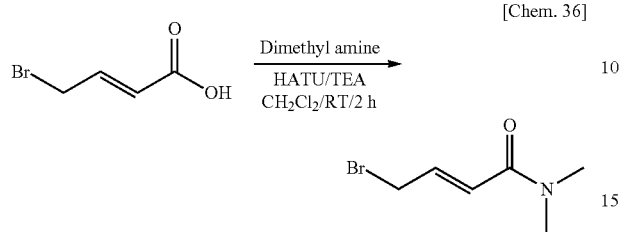

[Chem. 36]

(E)-4-bromobut-2-enoic acid (2 g, 12.2 mmol) was taken in dichloromethane (20 mL) and at 0° C. were added HATU (5.5 g, 14 mmol), triethyl amine (2.56 mL, 18.4 mmol) and stirred for 10 min at RT. To this mixture N,N-dimethyl amine (9.2 mL, 18 mmol) was added slowly and the contents were stirred at room temperature for 2 h. The volatiles were removed under reduced pressure and the residue was partitioned between water and ethyl acetate. The organic layer was washed with water, brine, dried over sodium sulphate and concentrated. The crude material was purified by column chromatography over 100-200 silica gel using 20% ethyl acetate in n-hexane to afford (E)-4-bromo-N,N-dimethylbut-2-enamide (0.4 g, 17%) as a pale green colour liquid.

Production Example 1i

Synthesis of tert-butyl (2-(4-iodophenoxy)ethyl)carbamate

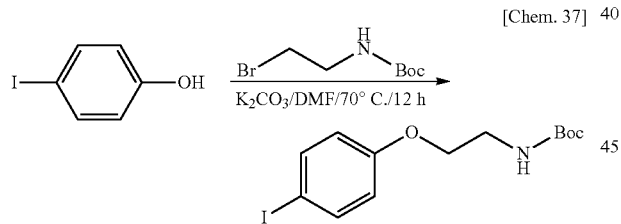

[Chem. 37]

The reaction was carried out according to Reference Production Example 1c to obtain the title compound of Production Example 1i as an off-white solid (80 g, 97%).

Production Example 1j

Synthesis of 2-(4-iodophenoxy)ethan-1-amine

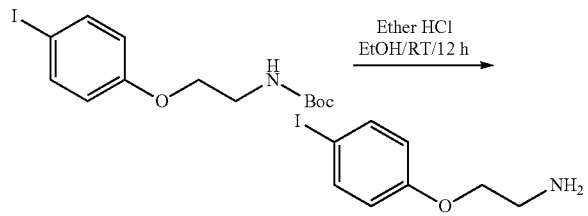

[Chem. 38]

To a stirred solution of tert-butyl (2-(4-iodophenoxy)ethyl)carbamate (25 g, 68.6 mmol, Production Example 1i) in ethanol (50 mL) was added at 0° C., 2M HCl in ether (250 mL). The reaction mixture was stirred for 12 h at room temperature. After completion of reaction, reaction mixture was basified with saturated NaHCO$_3$, extracted with 10% MeOH in DCM. Organic layer was concentrated under reduced pressure and the crude material was used in next step without further purification (16 g, 88%).

Production Example 1k

Synthesis of (E)-4-((2-(4-iodophenoxy)ethyl)amino)-N,N-dimethylbut-2-enamide

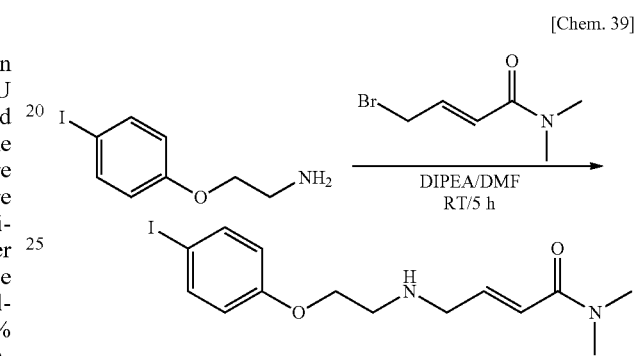

[Chem. 39]

The reaction was carried out according to Reference Production Example 1b, using (E)-4-bromo-N,N-dimethylbut-2-enamide (Production Example 1h) for compound 2 to give a crude product which was used in next step without further purification (18.8 g, crude).

Production Example 1l

Synthesis of tert-butyl (E)-(4-(dimethylamino)-4-oxobut-2-en-1-yl)(2-(4-iodophenoxy)ethyl)carbamate

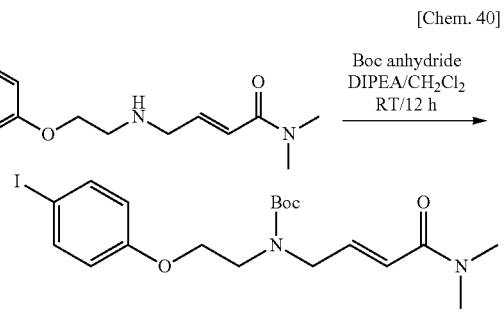

[Chem. 40]

To a stirred solution of (E)-4-((2-(4-iodophenoxy)ethyl)amino)-N,N-dimethylbut-2-enamide (18.8 g, 50.26 mmol) in dry dichloromethane (150 mL) was added DIPEA (6.4 g, 50.2 mmol) at 0° C., stirred for 15 min at 0° C. To the above reaction mixture, was added boc anhydride (13.1 g, 60.3 mmol), resulting mixture was stirred at room temperature for 12 h. Upon completion by TLC, the reaction mixture was cooled to 0° C., quenched with ice cold water (500 mL) and extracted with dichloromethane (500 mL). The combined organic extracts were washed with water, followed by brine, dried over anhydrous sodium sulphate and concentrated under reduced pressure. The crude material was purified by column chromatography over 230-400 mesh silica using 3% MeOH in dichloromethane as an eluent to afford tert-butyl (E)-(4-(dimethylamino)-4-oxobut-2-en-1-yl)(2-(4-iodophenoxy)ethyl)carbamate (9 g, 37.8%).

Production Example 1m

Synthesis of tert-butyl (2-((5-iodopyridin-2-yl)oxy)ethyl)carbamate

[Chem. 41]

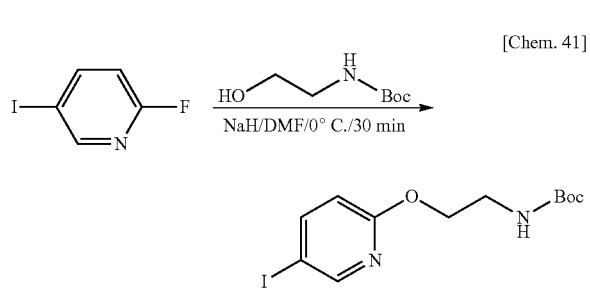

To a stirred solution of 2-fluoro-5-iodopyridine (5 g, 22.4 mmol) in DMF (25 mL) was added sodium hydride (0.7 g, 33.5 mmol) and stirred for 10 min at 0° C., to the above mixture tert-butyl (2-hydroxyethyl)carbamate (1.8 g, 11.2 mmol) was added. The contents were stirred at 0° C. for 30 min. After completion of reaction, reaction mixture was poured onto ice cold water, and extracted with ethyl acetate. The combined organic layers were washed with water followed by saturated NaCl solution, dried over anhydrous Na$_2$SO$_4$ and concentrated under reduced pressure. The crude material was purified by column chromatography over 230-400 mesh silica using 15% EtOAc in n-hexane as an eluent to obtain the desired compound tert-butyl (2-((5-iodopyridin-2-yl)oxy)ethyl)carbamate as an off-white solid (3.5 g, 43%).

Production Example 1n

Synthesis of tert-butyl (E)-(4-(dimethylamino)-4-oxobut-2-en-1-yl)(2-((5-iodopyridin-2-yl)oxy)ethyl)carbamate

[Chem. 42]

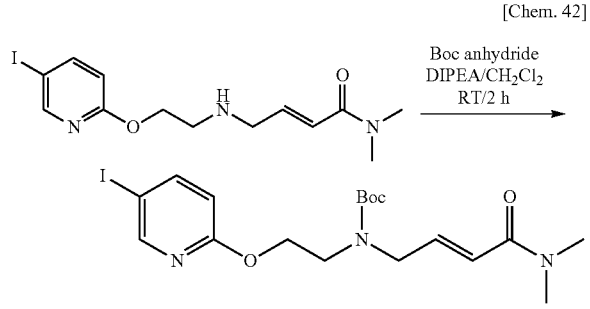

The reaction was carried out following the approach as described in Production Examples 1j to 1l, by substituting tert-butyl (2-((5-iodopyridin-2-yl)oxy)ethyl)carbamate for tert-butyl (2-(4-iodophenoxy)ethyl)carbamate to deliver the title compound (3.6 g, 47%).

Production Example 1o

Synthesis of tert-butyl ((E)-4-(dimethylamino)-4-oxobut-2-en-1-yl)(2-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)ethyl)carbamate

[Chem. 43]

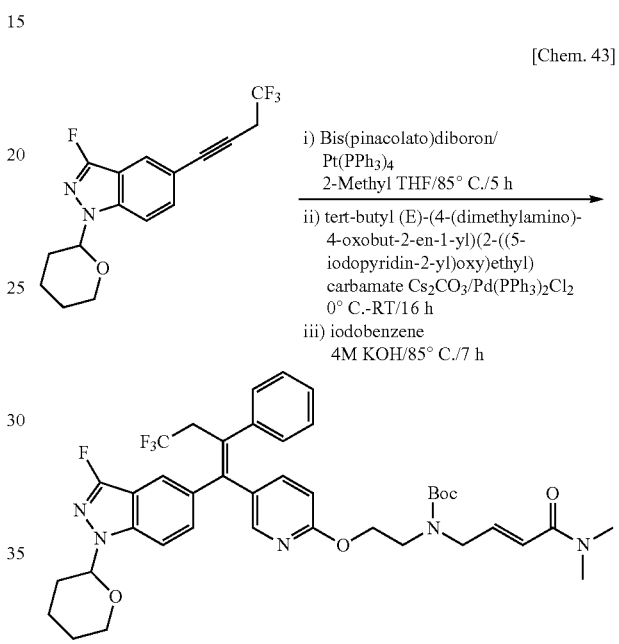

To a stirred solution of 3-fluoro-1-(tetrahydro-2H-pyran-2-yl)-5-(4,4,4-trifluorobut-1-yn-1-yl)-1H-indazole (0.66 g, 2.02 mmol, prepared as outlined in Production Example 1d through 1f) in 2-methyl THF (10 mL), was added bis (pinacolato)diboron (0.566 g, 2.22 mmol), tetrakis(triphenylphosphine)platinum (0) (0.025 g, 0.02 mmol) under nitrogen atmosphere, reaction mixture was stirred at 85° C. for 5 h. The solution was allowed to cool to room temperature and tert-butyl (E)-(4-(dimethylamino)-4-oxobut-2-en-1-yl)(2-((5-iodopyridin-2-yl)oxy)ethyl)carbamate (0.72 g, 1.51 mmol, prepared as outlined in Production Example 1n), bis(triphenylphosphine)palladium (II) dichloride (0.071 g, 0.1 mmol), cesium carbonate (1.3 g, 4.04 mmol) and 2-methyl THF (10 mL) were added. This mixture was degassed with nitrogen and water (0.12 mL) was added. This mixture was stirred at room temperature for 16 h. After completion of reaction, to the above reaction mixture 4M KOH (2.78 mL, 11.13 mmol) and iodobenzene (0.33 g, 1.61 mmol) were added. Reaction mixture was stirred at 85° C. for 7 h. After completion of reaction, reaction mixture was cooled to room temperature, diluted with water and extracted with EtOAc. The organic layer was dried over anhydrous sodium sulphate and concentrated under reduced pressure. The crude material was purified by combi-flash using 100% ethyl acetate as an eluent to afford tert-butyl ((E)-4-(dimethylamino)-4-oxobut-2-en-1-yl)(2-((5-((Z)-4,4,4-trifluoro-1-(3-fluoro-1-(tetrahydro-2H-pyran-2-yl)-1H-indazol-5-yl)-2-phenylbut-1-en-1-yl)pyridin-2-yl)oxy)ethyl)carbamate (0.35 g, 23%).

Production Example 1p

Synthesis of (E)-N,N-dimethyl-4-((2-((5-((Z)-4,4-trifluoro-1-(3-fluoro-1H-indazol-5-yl)-2-phenylbut-1-en-1-yl)pyridin-2-yl)oxy)ethyl)amino)but-2-enamide (compound (I))

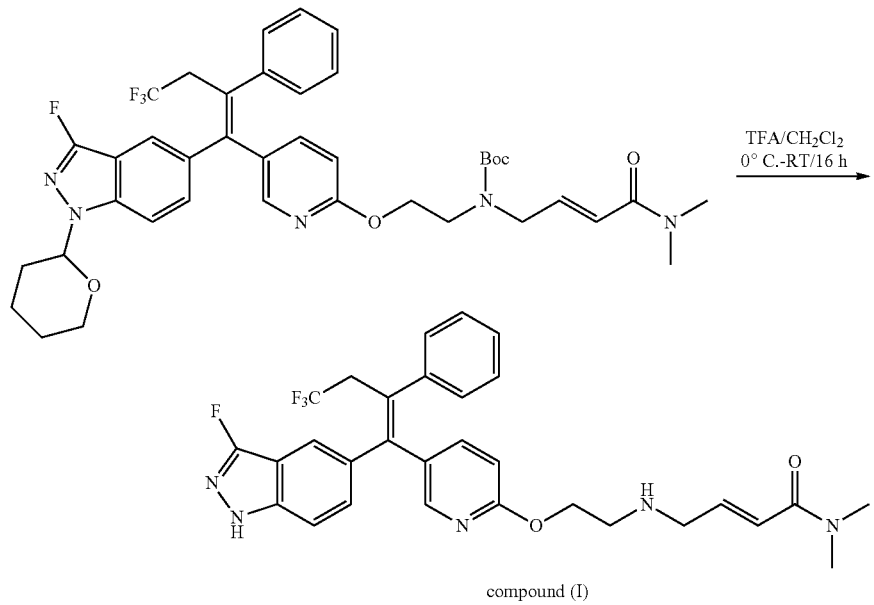

compound (I)

To a stirred solution of tert-butyl ((E)-4-(dimethylamino)-4-oxobut-2-en-1-yl)(2-((5-((Z)-4,4,4-trifluoro-1-(3-fluoro-1-(tetrahydro-2H-pyran-2-yl)-1H-indazol-5-yl)-2-phenyl-but-1-en-1-yl)pyridin-2-yl)oxy)ethyl)carbamate (0.35 g, 0.46 mmol) in dichloromethane (10 mL) was added TFA (1 mL) at 0° C. The reaction mixture was stirred for 16 h at room temperature. After completion of reaction, reaction mixture was basified with saturated NaHCO₃, extracted with ethyl acetate. Organic layer was concentrated under reduced pressure to afford crude compound, which was purified by preparative HPLC to afford desired compound (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide (0.03 g, 11%).

Compound (I): $^1$H NMR (400 MHz, Varian Mercury Plus, DMSO-$d_6$): δ 12.71 (s, 1H), 7.63 (s, 2H), 7.54 (m, 1H), 7.26-7.18 (m, 7H), 6.62-6.46 (m, 3H), 4.13 (t, J=5.8 Hz, 2H), 3.51-3.43 (m, 2H), 3.34-3.28 (m, 2H), 2.98 (s, 3H), 2.83 (s, 3H), 2.75 (t, J=5.8 Hz, 2H).

LCMS: 568.2 [M+H]⁺.

Production Example 1q

Synthesis of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide hydrochloride (hydrochloride salt of compound (I))

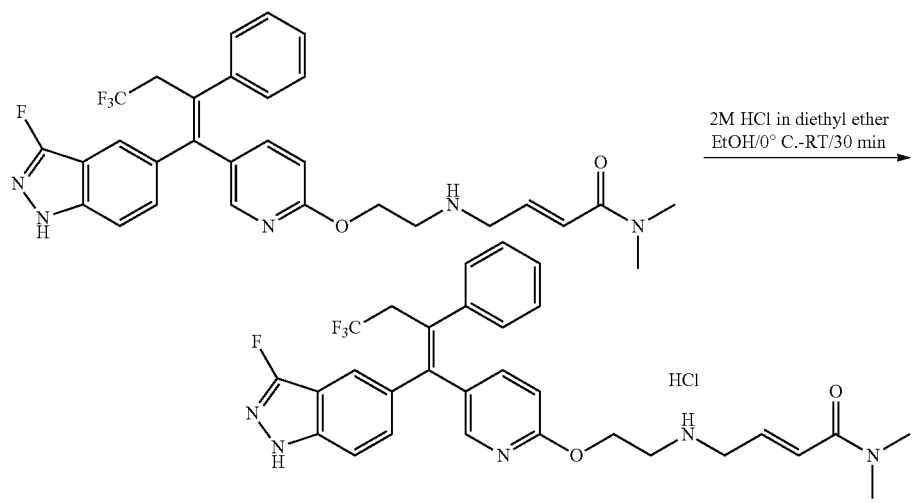

To a stirred solution of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide (4.1 g, 7.23 mmol) in ethanol (24 mL) was added 2M HCl in diethyl ether (7.5 mL) at 0° C. A white solid was observed in the reaction mixture after stirring for 30 min at room temperature. Reaction mixture was concentrated under vacuum at 35° C. and the solid obtained was co-distilled with dichloromethane under vacuum at 45° C. The solid obtained was washed with n-pentane and dried under vacuum at 50° C. for 4 h to obtain the title compound (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide hydrochloride (4.3 g, 98%).

$^1$H NMR (400 MHz, Varian Mercury Plus, DMSO-d$_6$): δ 12.74 (s, 1H), 9.26 (bs, 2H), 7.69-7.34 (m, 3H), 7.28-7.17 (m, 7H), 6.81 (d, J=15.2 Hz, 1H), 6.62-6.53 (m, 2H), 4.37 (t, J=4.4 Hz, 2H), 3.77-3.76 (m, 2H), 3.51-3.43 (m, 2H), 3.23 (bs, 2H), 3.03 (s, 3H), 2.86 (s, 3H).

LCMS: 568.3 [M+H]$^+$.

Example 1

Preparation of Crystal of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide hydrochloride To a solution of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide (500.31 mg) in 2-butanone (5 mL) was added a solution of hydrochloric acid (75.6 μL, 1 eq) in 2-butanone (5 mL). The mixture was stirred at room temperature for 4 days. The obtained solid was filtered off, washed with 2-butanone and dried overnight to give the titled crystal (514 mg, 97%). A powder X-ray diffraction pattern, a solid state $^{13}$C NMR spectrum and a graph showing hygroscopicity for the crystal obtained in Example 1 are shown in FIGS. 1, 7 and 13, respectively.

$^1$H NMR (600 MHz, Bruker AVANCE, DMSO-d$_6$): δ 12.71 (s, 1H), 9.02 (br s, 2H), 7.67 (d, J=1.9 Hz, 1H), 7.63 (s, 1H), 7.54 (dd, J=8.7, 1.5 Hz, 1H), 7.29 (dd, J=8.6, 2.4 Hz, 1H), 7.22-7.27 (m, 5H), 7.16-7.21 (m, 1H), 6.78 (d, J=15.2 Hz, 1H), 6.61 (d, J=9.0 Hz, 1H), 6.54 (dt, J=15.1, 6.5 Hz, 1H), 4.34 (t, J=5.0 Hz, 2H), 3.76 (br d, J=6.4 Hz, 2H), 3.45 (q, J=10.8 Hz, 2H), 3.23 (br t, J=4.3 Hz, 2H), 3.01 (s, 3H), 2.86 (s, 3H). Typical peaks in a solid state $^{13}$C NMR spectrum and typical diffraction peaks in a powder X-ray diffractometry for the crystal obtained in Example 1 are shown below. $^{13}$C NMR (100 MHz, solid state): δ 164.3, 162.2, 148.6, 138.9, 136.8, 134.0, 111.9, 61.5, 38.4, 34.4.

Powder X-ray diffraction angle (2θ±0.2°): 6.1°, 11.8°, 14.9°, 16.8°, 18.1°, 19.1°, 19.5°, 21.7°, 25.9°, 27.4°.

Example 2

Preparation of crystal of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide hydrobromide To a solution of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide (500.44 mg) in 2-butanone (5 mL) was added a solution of hydrobromic acid (100.3 μL, 1 eq) in 2-butanone (5 mL). The mixture was stirred at room temperature for 4 days. The obtained solid was filtered off, washed with 2-butanone and dried overnight to give the titled crystal (545 mg, 95%). A powder X-ray diffraction pattern, a solid state $^{13}$C NMR spectrum and a graph showing hygroscopicity for the crystal obtained in Example 2 are shown in FIGS. 2, 8 and 14, respectively.

$^1$H NMR (600 MHz, Bruker AVANCE, DMSO-d$_6$): δ 12.69 (s, 1H), 8.83 (br s, 2H), 7.68 (d, J=2.5 Hz, 1H), 7.63 (s, 1H), 7.55 (dd, J=8.7, 1.6 Hz, 1H), 7.29 (dd, J=8.7, 2.5 Hz, 1H), 7.22-7.27 (m, 5H), 7.17-7.20 (m, 1H), 6.77 (d, J=15.1 Hz, 1H), 6.61 (d, J=8.5 Hz, 1H), 6.53 (dt, J=15.2, 6.6 Hz, 1H), 4.33 (br t, J=5.0 Hz, 2H), 3.77 (br d, J=6.4 Hz, 2H), 3.45 (q, J=10.8 Hz, 2H), 3.25 (br t, J=4.6 Hz, 2H), 3.01 (s, 3H), 2.86 (s, 3H).

Typical peaks in a solid state $^{13}$C NMR spectrum and typical diffraction peaks in a powder X-ray diffractometry for the crystal obtained in Example 2 are shown below.

$^{13}$C NMR (100 MHz, solid state): δ 164.5, 162.2, 148.6, 139.3, 135.8, 134.0, 111.7, 60.9, 39.0, 34.5.

Powder X-ray diffraction angle (2θ±0.2°): 6.2°, 11.7°, 12.5°, 16.5°, 17.6°, 18.7°, 20.4°, 21.4°, 22.5°, 27.1°.

Example 3

Preparation of crystal form A of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide maleate To a solution of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide (100.25 mg) in 2-butanone (1 mL) was added a solution of maleic acid (10 mg/mL) in 2-butanone (2.05 mL). Then hexane (2 mL) was added to the solution, and the mixture was stirred at room temperature for 4 days. The obtained solid was filtered off, washed with 2-butanone to give the titled crystal (107 mg, 89%). A powder X-ray diffraction pattern, a solid state $^{13}$C NMR spectrum and a graph showing hygroscopicity for the crystal obtained in Example 3 are shown in FIGS. 3, 9 and 15, respectively.

$^1$H NMR (600 MHz, Bruker AVANCE, DMSO-d$_6$): δ 12.69 (s, 1H), 8.72 (br s, 1H), 7.68 (d, J=2.2 Hz, 1H), 7.63 (s, 1H), 7.55 (dd, J=8.6, 1.2 Hz, 1H), 7.29 (dd, J=8.6, 2.4 Hz, 1H), 7.22-7.27 (m, 5H), 7.16-7.21 (m, 1H), 6.76 (d, J=15.2 Hz, 1H), 6.60 (d, J=8.6 Hz, 1H), 6.53 (dt, J=15.1, 6.6 Hz, 1H), 6.01 (s, 2H), 4.30-4.36 (m, 2H), 3.76 (br d, J=6.4 Hz, 2H), 3.46 (q, J=10.7 Hz, 2H), 3.22-3.27 (m, 2H), 3.01 (s, 3H), 2.86 (s, 3H). Typical peaks in a solid state $^{13}$C NMR spectrum and typical diffraction peaks in a powder X-ray diffractometry for the crystal obtained in Example 3 are shown below.

$^{13}$C NMR (100 MHz, solid state): δ 169.6, 168.0, 134.2, 117.1, 112.0, 107.3, 63.6, 50.3, 46.9, 36.1.

Powder X-ray diffraction angle (2θ±0.2°): 4.9°, 9.8°, 16.1°, 16.7°, 17.9°, 19.4°, 21.2°, 22.9°, 24.9°, 30.4°.

Example 4

Preparation of crystal form B of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide maleate To a solution of (E)-N,N-dimethyl-4-((2-((5-((Z)-4,4,4-trifluoro-1-(3-fluoro-1H-indazol-5-yl)-2-phenyl but-1-en-1- yl)pyridin-2-yl)oxy)ethyl)amino)but-2-enamide (499.69 mg) in 2-butanone (6 mL) was added to a solution of maleic acid (102.06 mg, 1 eq) in 2-butanone (5 mL). The mixture was stirred at room temperature for 1 day. Hexane (6 mL) was added to the mixture and stirred at room temperature for 3 days. The obtained solid was filtered off, washed with 2-butanone and dried overnight to give the titled crystal (507 mg, 84%). A powder X-ray diffraction pattern, a solid state $^{13}$C NMR spectrum and a graph showing hygroscopicity for the crystal obtained in Example 4 are shown in FIGS. 4, 10 and 16, respectively.

$^1$H NMR (600 MHz, Bruker AVANCE, DMSO-$d_6$): δ 12.69 (s, 1H), 8.73 (br s, 2H), 7.68 (d, J=1.8 Hz, 1H), 7.63 (s, 1H), 7.54 (dd, J=8.7, 1.3 Hz, 1H), 7.29 (dd, J=8.7, 2.4 Hz, 1H), 7.22-7.27 (m, 5H), 7.16-7.20 (m, 1H), 6.76 (d, J=15.2 Hz, 1H), 6.60 (d, J=8.6 Hz, 1H), 6.53 (dt, J=15.2, 6.5 Hz, 1H), 6.01 (s, 2H), 4.30-4.35 (m, 2H), 3.76 (br d, J=6.3 Hz, 2H), 3.46 (q, J=10.8 Hz, 3H), 3.22-3.26 (m, 3H), 3.01 (s, 3H), 2.86 (s, 3H). Typical peaks in a solid state $^{13}$C NMR spectrum and typical diffraction peaks in a powder X-ray diffractometry for the crystal obtained in Example 4 are shown below.

$^{13}$C NMR (100 MHz, solid state): δ 171.4, 167.1, 133.3, 117.8, 112.8, 108.6, 63.1, 48.8, 44.5, 38.3.

Powder X-ray diffraction angle (2θ±0.2°): 14.8°, 15.8°, 17.1°, 17.5°, 20.2°, 20.9°, 22.3°, 24.6°, 26.5°, 28.5°.

Example 5

Preparation of crystal of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide L-mandelate To a solution of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide (375.57 mg) in 2-butanone (5 mL) was added a solution of L-mandelic acid (100.28 mg, 1 eq) in 2-butanone (5 mL). The mixture was stirred at room temperature for 1 day. 2-Butanone (4 mL) was added to the mixture and stirred at room temperature for 3 days. The obtained solid was filtered off, washed with 2-butanone and dried overnight to give the titled crystal (412 mg, 86%). A powder X-ray diffraction pattern, a solid state $^{13}$C NMR spectrum and a graph showing hygroscopicity for the crystal obtained in Example 5 are shown in FIGS. 5, 11 and 17, respectively.

$^1$H NMR (600 MHz, Bruker AVANCE, DMSO-$d_6$): δ 12.69 (br s, 1H), 7.64 (d, J=1.8 Hz, 1H), 7.62 (s, 1H), 7.53 (dd, J=8.7, 1.3 Hz, 1H), 7.38 (d, J=7.2 Hz, 2H), 7.29 (t, J=7.5 Hz, 2H), 7.21-7.27 (m, 7H), 7.15-7.20 (m, 1H), 6.56 (t, J=4.8 Hz, 1H), 6.54-6.55 (m, 1H), 6.52-6.54 (m, 1H), 4.85 (s, 1H), 4.17 (t, J=5.6 Hz, 2H), 3.46 (m, 2H), 3.40 (m, 2H), 2.97 (s, 3H), 2.86 (br t, J=5.6 Hz, 2H), 2.83 (s, 3H).

Typical peaks in a solid state $^{13}$C NMR spectrum and typical diffraction peaks in a powder X-ray diffractometry for the crystal obtained in Example 5 are shown below. 13C NMR (100 MHz, solid state): δ 176.8, 165.9, 160.7, 147.7, 141.2, 110.5, 76.3, 48.6, 37.2, 34.1.

Powder X-ray diffraction angle (2θ±0.2°): 5.1°, 8.8°, 10.3°, 13.8°, 16.9°, 18.3°, 19.2°, 21.2°, 22.8°, 24.6°.

Example 6

Preparation of crystal of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide benzenesulfonate To a solution of (E)-N,N-dimethyl-4-((2-((5-((Z)-4,4,4-trifluoro-1-(3-fluoro-1H-indazol-5-yl)-2-phenyl but-1-en-1-yl)pyridin-2-yl)oxy)ethyl)amino)but-2-enamide (501.14 mg) in ethyl acetate (3 mL) was added a solution of benzenesulfonic acid monohydrate (100 mg/mL) in ethyl acetate (1.6 mL). Then ethyl acetate (5 mL) was added to the solution, and the mixture was stirred at 45° C. for 3 days. The obtained solid was filtered off and dried for 3 days to give the titled crystal (572 mg, 87%). A powder X-ray diffraction pattern, a solid state $^{13}$C NMR spectrum and a graph showing hygroscopicity for the crystal obtained in Example 6 are shown in FIGS. 6, 12 and 18, respectively.

$^1$H NMR (600 MHz, Bruker AVANCE, DMSO-$d_6$): δ 12.69 (s, 1H), 8.72 (br s, 1H), 7.68 (d, J=2.1 Hz, 1H), 7.63 (s, 1H), 7.59 (dd, J=7.8, 1.8 Hz, 2H), 7.55 (dd, J=8.7, 1.4 Hz, 1H), 7.23-7.31 (m, 9H), 7.17-7.20 (m, 1H), 6.77 (d, J=15.2 Hz, 1H), 6.61 (d, J=8.6 Hz, 1H), 6.54 (dt, J=15.2, 6.6 Hz, 1H), 4.33 (t, J=5.1 Hz, 2H), 3.77 (d, J=6.3 Hz, 2H), 3.46 (q, J=10.8 Hz, 2H), 3.24 (t, J=5.0 Hz, 2H), 3.01 (s, 3H), 2.86 (s, 3H)

Typical peaks in a solid state $^{13}$C NMR spectrum and typical diffraction peaks in a powder X-ray diffractometry for the crystal obtained in Example 6 are shown below.

$^{13}$C NMR (100 MHz, solid state): δ 163.0, 160.9, 147.2, 145.0, 140.2, 133.4, 109.3, 47.1, 37.3, 34.8.

Powder X-ray diffraction angle (2θ±0.2°: 5.2°, 9.5°, 10.5°, 12.1°, 15.4°, 17.4°, 20.3°, 21.4°, 23.1°, 24.4°.

Solubility

The excess amount of the crystal obtained in Example 6 was added into 0.1 mol/L HCl solution in a test tube, and was dissolved at 37° C. with shaking for an hour. The concentration of the filtrate was measured to determine the solubility by using high performance liquid chromatography (HPLC). The solubility of the crystal obtained in Example 6 was 2 mg/mL.

The following test examples were carried out to examine the pharmacological effects of the compound (I).

(Test Example 1) Compounds that Inhibit ERα$^{WT/}$$_{MUT}$ Activity In Vitro

Cell Culture

MCF7 BUS cells (Coser, et al., (2003) PNAS 100 (24): 13994-13999) were maintained in Dulbecco's Modified Eagle Medium supplemented with 10% FBS, 4 mM L-glutamine and 1× non-essential amino acids. Lenti-X 293T cells (Clontech, Cat #632180) were routinely cultured in Dulbecco's Modified Eagle Medium supplemented with 10% FBS.

Site-Direct Mutagenesis and Cell Line Engineering

The QuikChange II XL Site-Directed Mutagenesis Kit (Agilent Technologies, Cat #200523) was used to generate Y537S, Y537C, Y537N and D538G mutations within the ERα exon 8. Wild-type ESR1 cDNA (GeneCopoeia Inc., Cat# GC-A0322, accession no. NM 000125) was used as a template with the following mutagenesis primers (where the underlined nucleotides represent site mutations); Y537S: F-AAG AAC GTG GTG CCC CTC TCT GAC CTG CTG CTG GAG ATG (SEQ ID NO: 1), R-CAT CTC CAG CAG CAG GTC AGA GAG GGG CAC CAC GTT CTT (SEQ ID NO: 2); Y537N: F-AAG AAC GTG GTG CCC CTC AAT GAC CTG CTG CTG GAG ATG (SEQ ID NO: 3), R-CAT CTC CAG CAG CAG GTC ATT GAG GGG CAC CAC GTT CTT (SEQ ID NO: 4); Y537C: F-AAG AAC GTG GTG CCC CTC T GT GAC CTG CTG CTG GAG ATG (SEQ ID NO: 5), R-CAT CTC CAG CAG CAG GTC ACA GAG GGG CAC CAC GTT CTT (SEQ ID NO: 6); D538G: F-AAC GTG GTG CCC CTC TAT GGC CTG CTG CTG GAG ATG CTG (SEQ ID NO: 7), R-CAG CAT CTC CAG CAG CAG GCC ATA GAG GGG CAC CAC GTT (SEQ ID NO: 8). WT and mutant ESR1 cDNAs were cloned into the designation lentiviral vector pLenti6.3/V5-Dest (Invitrogen, Cat #V533-06). To make lentivirus, DNAs (WT and mutant ESR1) were co-transfected with packaging plasmids into Lenti-X 293T cells using TransIT (Mirus, Cat #MIR 2700). 48 h post-transfection, virus containing media was filtered and added to MCF7 cells in the presence of 8 µ/ml polybrene overnight. Two days following infection, cells were placed under selection with 10 µg/ml blasticidin for 2 weeks for stable expression.

In Vitro Proliferation Assays

MCF7-WT and -Y537S cells were seeded at 1500 cells/well in black-walled 96-well plates (assay plates, Costar, Cat #3904). In parallel, cells were also seeded in a separate 96-well plate (8 wells/cell line, control plate) for which a CTG (CellTiter-Glo (registered trademark) Luminescent Viability Assay, Promega, Cat #G7572) was measured the following day (day 0 reading). The day 0 reading was used for the $GI_{50}$ calculation at the termination of the experiment. The day following seeding, compounds were added to assay plates. Briefly, a 1:4 serial dilution was prepared in DMSO at 200× final concentration for a total of 10 concentrations (9 dilutions containing compound and one is DMSO only). Serially diluted compounds were pipetted into medium to prepare a compound-medium mix at 10× final concentration. 10 µl of compound-medium mix was added to MCF7-WT and -Y537S cells at 3 wells/concentration (triplicate for each concentration). On day 3, media/compound was removed and replaced with fresh media/compound as described above. On day 6, CTG was measured and compared to day 0 readings from control plate to assess $GI_{50}$.

Results

FIG. 19 shows that ectopic expression of $ER\alpha^{Y537S/N/C,D538G}$ in MCF7 cells conferred phenotypic resistance to currently marketed therapies tamoxifen (SERM), raloxifene (SERM) and fulvestrant (SERD). Similar observations were also recently published by several independent labs (Jeselsohn et al., (2014) Clin Cancer Res. April 1; 20 (7): 1757-67; Toy et al., (2013) Nat. Genet. 2013 December; 45(12):1439-45; Robinson et al., (2013) Nat. Genet. December; 45 (12): 1446-51; Merenbakh-Lamin et al., (2013) Cancer Res. December 1; 73(23): 6856-64; Yu et al., (2014) Science July 11; 345(6193): 216-20). Having confirmed that $ER\alpha^{MUT}$ drive resistance to current endocrine therapies, identification of novel compounds that would reduce proliferation of the $ER\alpha^{MUT}$-bearing MCF7 cells more efficaciously than the corresponding clinical compound 4-hydroxytamoxifen was sought. Using the WT and mutant viability assay as a screening tool, compounds were identified that were more potent towards the Y537S-bearing MCF7 line relative to 4-hydroxytamoxifen. The results of the viability assay screen for the compound (I) are as follows: $GI_{50}$ (WT): 0.34 nM; $GI_{50}$ (Y537S): 4.26 nM.

(Test Example 2) In Vivo Xenograft Methods

In the Test Example 2, references to compound (I) refers to a hydrochloride salt of the compound (I) obtained in Production Example 1q.

MCF7 Xenograft Study

The ESR1 wild-type human ER+ breast cancer cell line MCF7 (ATCC) was cultured in DMEM media supplemented with 10% FBS at 37° C. in a 5% CO2 atmosphere and kept in the exponential growth phase. The cells were collected in trypsin and resuspended in a 1:1 mixture of matrigel and HBSS at a final concentration of $5\times10^7$ cells/mL. A 0.2 mL aliquot of cells was injected subcutaneously into the $3^{rd}$ mammary fat pad of 6-8 week old female Balb/c nude mice, giving $1\times10^7$ cells/mouse. When the average tumor volume reached approximately 155 mm³, 92 animals were randomized prior to treatment.

Anti-tumor activity in the MCF7 xenograft model was examined using compound (I). The compound (I) was dosed orally every day at doses ranging from 1 to 30 mg/kg. Each treatment was started on Day 0 and the administration schedule was continued for 17 days. The administration volume was calculated from the individual mouse body weights prior to dose administration. The body weights were measured daily while the tumor volumes were measured twice a week. Tumor volumes (TV) were calculated based on the formula:

TV=length×width²×0.5 length: largest diameter of tumor (mm)
width: diameter perpendicular to length (mm)

The Tumor Growth Inhibition % (TGI) was calculated according to the following formula:

$$TumorGrowthInhibition\%\ (TGI) = \frac{\text{Average Control } TV \text{ Day } X - \text{Treatment } TV \text{ Day } X}{\text{Average Control } TV \text{ Day } X} \times 100 \qquad [\text{Math. 1}]$$

Where Day X is the endpoint measurement.

Y537S Positive PDx Xenograft Study

A Patient-Derived Xenograft (PDX) tumor model representing an ESR1-Y537S mutated human ER+ breast cancer, designated as PDX-Y537S, was propagated subcutaneously in immunocompromised mice. The tumors were excised within 60 days of implantation and processed to mixed tumor fragments. Solid tumor tissues were depleted of necrotic components, cut into 70 mg fragments, mixed with matrigel and subcutaneously implanted into the right flank of 6-12 week old female athymic Nude (Crl:NU(NCr)-Foxn1nu) mice. The precise number of fragments and volume of matrigel was determined on a case by case basis. When the average tumor volume reached approximately 200 mm³, animals were randomized prior to treatment. All of the primary human tumors utilized in this study had undergone approximately 7 passages in vivo.

Anti-tumor activity in the PDX-Y537S model was examined using the compound (I). Estrogen was not supplemented in the studies. The compound (I) was dosed orally every day at doses ranging from 3 to 200 mg/kg. Each treatment was started on Day 0 and the administration schedule was continued for up to 35 days. The administration volume was calculated from the individual mouse body weights prior to dose administration. The body weights were measured daily while the tumor volumes were measured twice a week. Tumor volumes were calculated based on the previously described formula.

WHIM20 Xenograft Study

The Patient-Derived Xenograft (PDX) tumor model, WHIM20, representing an ESR1-Y537S mutated human ER+breast cancer was propagated in mice. The tumors were excised and processed to mixed tumor fragments and the fragments were reimplanted subcutaneously into new recipient mice. For the current work, solid tumor tissues were depleted of necrotic components, cut into fragments, mixed with matrigel and subcutaneously implanted into the right flank of 6-8 week old female SCID-bg mice. The precise number of fragments and volume of matrigel was determined on a case by case basis. When the average tumor volume reached approximately 370 mm³, animals were randomized prior to treatment. All of the primary human tumors utilized in this study had undergone approximately 4 passages in vivo.

Anti-tumor activity in the WHIM20 patient derived xenograft model was examined using the compound (I). Estrogen was not supplemented in WHIM20 studies. The compound (I) was dosed orally every day at the indicated doses. Each treatment was started on Day 0 and the administration schedule was continued for the indicated days. The administration volume was calculated from the individual mouse body weights prior to dose administration. The body weights were measured daily while the tumor volumes were measured twice a week. Tumor volumes were calculated based on the previously described formula.

Statistical Analysis

Data are expressed as the mean±SEM for tumor volume and the mean±SEM for body weight. The differences in tumor volume during the study period between the vehicle treated and compound treated groups were analyzed by two-way analysis of variance (ANOVA) followed by the Dunnett multiple comparison post hoc test. Statistical analyses were performed using the GraphPad Prism (registered trademark) version 5.04 (GraphPad Software, La Jolla, Calif.).

Results (1)

FIG. 20 shows the antitumor and body weight effects of the compound (I) in the MCF7 subcutaneous xenograft model carrying wild-type ER grown in immunocompromised mice. The compound (I) inhibited xenograft growth in a dose dependent manner with 3 mg/kg QD, 10 mg/kg QD and 30 mg/kg QD treatments inhibiting growth on day 17 (TGI of 75%, 80% and 85% and $p<0.0001$ for all doses, respectively). The compound (I) treatment of 1 mg/kg QD×18 did not show a statistically meaningful difference from the control treated group (TGI of 36%, $p>0.05$). All doses and regimens were well tolerated with no significant body weight loss or clinical signs.

The compound (I) was given orally once daily for the duration of the study. Data represent the mean±SEM (Tumor Volume) or mean±SEM (Body Weight) (N=6 for treatment groups, N=8 for Vehicle control). *$p<0.0001$ versus vehicle control on Day 17 (Two-Way ANOVA followed by the Dunnett multiple comparison test).

Results (2)

FIG. 21 shows the antitumor and body weight effects of the compound (I) in a repeat study in the ER+ PDX-Y537S model bearing a heterozygous Y537S mutation. The compound (I) inhibited xenograft growth in a dose dependent manner with 3 mg/kg QD, 10 mg/kg QD, 30 mg/kg QD and 100 mg/kg QD treatments significantly inhibiting growth on day 28 (TGI of 61%, 85%, 81% and 84% and $p<0.001$, $p<0.0001$, $p<0.0001$ and $p<0.0001$, respectively). All doses were well tolerated with no significant body weight loss or clinical signs.

The compound (I) was given orally once daily for the duration of the study. Data represent the mean±SEM (Tumor Volume) or mean±SEM (Body Weight) (N=6 for the compound (I) and N=8 for vehicle). *$p<0.001$, **$p<0.0001$ versus vehicle control on Day 28 (Two-Way ANOVA followed by the Dunnett multiple comparison test).

Results (3)

FIG. 22 shows the anti-tumor and body weight effects of the compound (I) in the ER+ WHIM20 PDX model bearing a homozygous Y537S mutation. The compound (I) inhibited xenograft growth in a dose dependent manner with 10 mg/kg QD, 30 mg/kg QD and 100 mg/kg QD treatments significantly inhibiting growth on day 22 (TGI of 26%, 36%, and 48% and $p<0.05$, $p<0.01$ and $p<0.0001$, respectively). This dose of the compound (I) was tolerated in accordance with internal animal care and use committee guidelines.

The compound (I) was given orally once daily for the duration of the study. Data represent the mean±SEM (Tumor Volume) or mean±SEM (Body Weight) (N=8 for all groups). *$p<0.05$, $p<0.01$ and *$p<0.0001$ respectively versus vehicle control on Day 22 (Two-Way ANOVA followed by the Dunnett multiple comparison test).

The invention claimed is:

1. A crystal of hydrochloride salt of (E)-N,N-dimethyl-4-((2-((5-((Z)-4,4-trifluoro-1-(3-fluoro-1H-indazol-5-yl)-2-phenylbut-1-en-1-yl)pyridin-2-yl)oxy)ethyl)amino)but-2-enamide represented by the formula I, characterized by having one or more diffraction peaks at diffraction angles (2θ±0.2°) selected from the group consisting of 6.1°, 11.8°, 16.8°, 18.1° and 19.5° in a powder X-ray diffractometry formula I

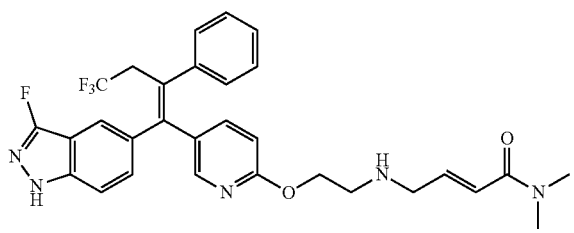

2. The crystal according to claim 1, characterized by having a diffraction peak at a diffraction angle (2θ±0.2°) of 18.1° in a powder X-ray diffractometry.

3. The crystal according to claim 1, characterized by having diffraction peaks at diffraction angles (2θ±0.2°) of 6.1°, 11.8° and 18.1° in a powder X-ray diffractometry.

4. A crystal of hydrochloride salt of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide represented by the formula I, characterized by having a powder X-ray diffraction pattern substantially the same as the powder X-ray diffraction pattern shown in FIG. 1 formula I

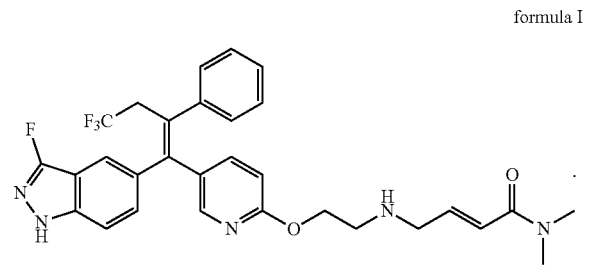 [SMILES: CN(C)C(=O)/C=C/CNCCOc1ccc(/C(=C(/CC(F)(F)F)c2ccccc2)c2ccc3[nH]nc(F)c3c2)cn1]

5. A crystal of hydrobromide salt of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide represented by the formula I, characterized by having one or more diffraction peaks at diffraction angles (2θ±0.2°) selected from the group consisting of 6.2°, 11.7°, 18.7°, 20.4° and 22.5° in a powder X-ray diffractometry formula I

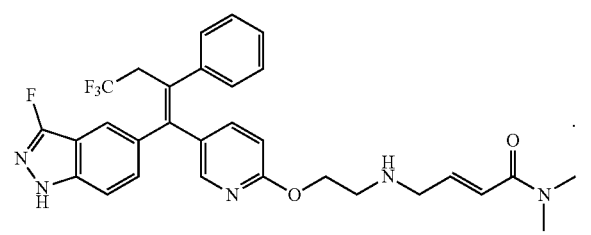

6. The crystal according to claim 5, characterized by having a diffraction peak at a diffraction angle (2θ±0.2°) of 18.7° in a powder X-ray diffractometry.

7. The crystal according to claim 5, characterized by having diffraction peaks at diffraction angles (2θ±0.2°) of 6.2°, 18.7° and 22.5° in a powder X-ray diffractometry.

8. A crystal of hydrobromide salt of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide represented by the formula I, characterized by having a powder X-ray diffraction pattern substantially the same as the powder X-ray diffraction pattern shown in FIG. 2 formula I

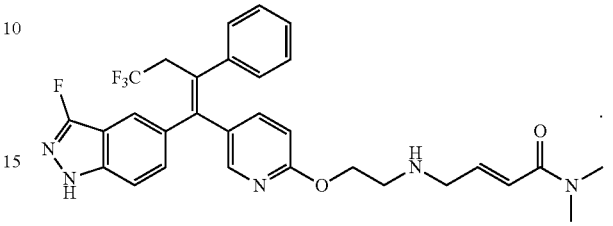

9. A crystal form A of maleate salt of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide represented by the formula I, characterized by having one or more diffraction peaks at diffraction angles (2θ±0.2°) selected from the group consisting of 16.7°, 17.9°, 21.2°, 22.9° and 24.9° in a powder X-ray diffractometry formula I

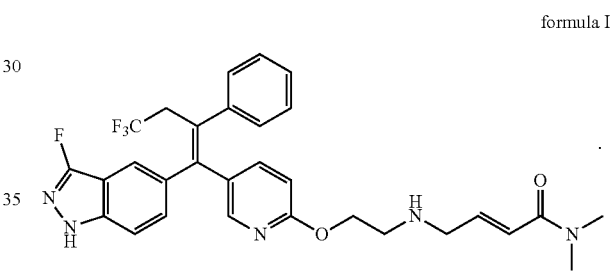

10. The crystal according to claim 9, characterized by having a diffraction peak at a diffraction angle (2θ±0.2°) of 24.9° in a powder X-ray diffractometry.

11. The crystal according to claim 9, characterized by having diffraction peaks at diffraction angles (2θ±0.2°) of 17.9°, 22.9° and 24.9° in a powder X-ray diffractometry.

12. A crystal form A of maleate salt of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide represented by the formula I, characterized by having a powder X-ray diffraction pattern substantially the same as the powder X-ray diffraction pattern shown in FIG. 3 formula I

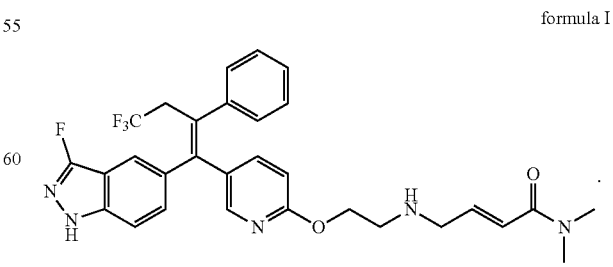

13. A crystal form B of maleate salt of (E)-N,N-dimethyl-4-((2-((5-((Z)-4,4,4-trifluoro-1-(3-fluoro-1H-indazol-5-yl)-

2-phenylbut-1-en-1-yl)pyridin-2-yl)oxy)ethyl)amino)but-2-enamide represented by the formula I, characterized by having one or more diffraction peaks at diffraction angles (2θ±0.2°) selected from the group consisting of 14.8°, 20.2°, 22.3° and 26.5° in a powder X-ray diffractometry

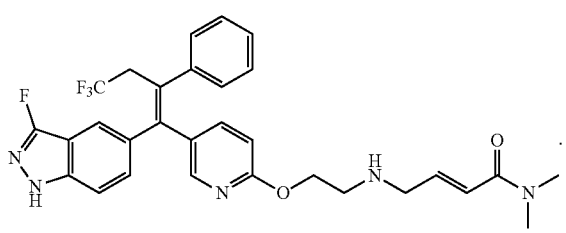

formula I

14. The crystal according to claim 13, characterized by having a diffraction peak at a diffraction angle (2θ±0.2°) of 22.3° in a powder X-ray diffractometry.

15. The crystal according to claim 13, characterized by having diffraction peaks at diffraction angles (2θ±0.2°) of 14.8°, 20.2° and 22.3° in a powder X-ray diffractometry.

16. A crystal form B of maleate salt of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide represented by the formula I, characterized by having a powder X-ray diffraction pattern substantially the same as the powder X-ray diffraction pattern shown in FIG. 4

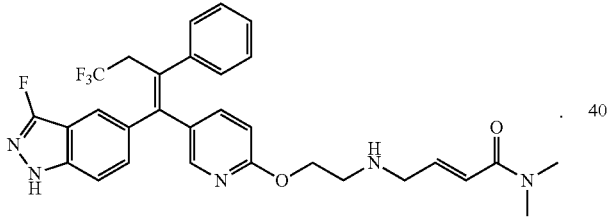

formula I

17. A crystal of L-mandelate salt of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide represented by the formula I, characterized by having one or more diffraction peaks at diffraction angles (2θ±0.2°) selected from the group consisting of 5.1°, 8.8°, 10.3°, 16.9° and 18.3° in a powder X-ray diffractometry

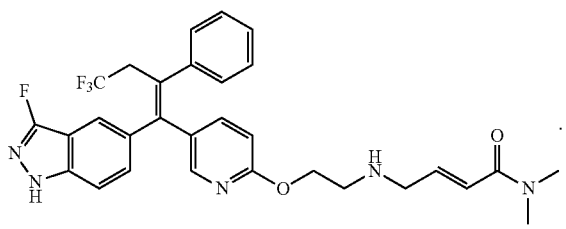

formula I

18. The crystal according to claim 17, characterized by having a diffraction peak at a diffraction angle (2θ±0.2°) of 18.3° in a powder X-ray diffractometry.

19. The crystal according to claim 17, characterized by having diffraction peaks at diffraction angles (2θ±0.2°) of 5.1°, 10.3° and 18.3° in a powder X-ray diffractometry.

20. A crystal of L-mandelate salt of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide represented by the formula I, characterized by having a powder X-ray diffraction pattern substantially the same as the powder X-ray diffraction pattern shown in FIG. 5

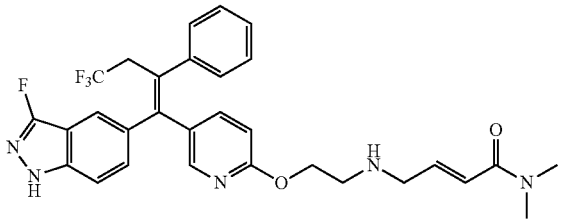

formula I

21. A crystal of benzenesulfonate salt of (E)-N,N-dimethyl-4-((2-((5-((Z)-4,4,4-trifluoro-1-(3-fluoro-1H-indazol-5-yl)-2-phenylbut-1-en-1-yl)pyridin-2-yl)oxy)ethyl)amino)but-2-enamide represented by the formula I, characterized by having one or more diffraction peaks at diffraction angles (2θ±0.2°) selected from the group consisting of 5.2°, 9.5°, 10.5°, 21.4° and 24.4° in a powder X-ray diffractometry formula I

22. The crystal according to claim 21, characterized by having a diffraction peak at a diffraction angle (2θ±0.2°) of 9.5° in a powder X-ray diffractometry.

23. The crystal according to claim 21, characterized by having diffraction peaks at diffraction angles (2θ±0.2°) of 5.2°, 9.5° and 10.5° in a powder X-ray diffractometry.

24. A crystal of benzenesulfonate salt of (E)-N,N-dimethyl-4-((2-((5-((Z)-4,4,4-trifluoro-1-(3-fluoro-1H-indazol-5-yl)-2-phenylbut-1-en-1-yl) pyridin-2-yl)oxy)ethyl)amino)but-2-enamide represented by the formula I, characterized by having a powder X-ray diffraction pattern substantially the same as the powder X-ray diffraction pattern shown in FIG. 6 formula I
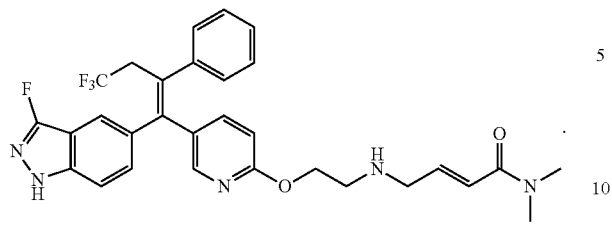
25. A pharmaceutical composition comprising the salt or the crystal thereof according to any one of claims 1, 3, 4, 5, 7, 8, 9, 11, 12, 13, 15, 16, 17, 19, 20, 21, 23, and 24.
* * * * *

SEQUENCE LISTING

```
<160> NUMBER OF SEQ ID NOS: 8

<210> SEQ ID NO 1
<211> LENGTH: 39
<212> TYPE: DNA
<213> ORGANISM: artificial sequence
<220> FEATURE:
<223> OTHER INFORMATION: mutagenesis primer

<400> SEQUENCE: 1
aagaacgtgg tgccctctc tgacctgctg ctggagatg                    39

<210> SEQ ID NO 2
<211> LENGTH: 39
<212> TYPE: DNA
<213> ORGANISM: artificial sequence
<220> FEATURE:
<223> OTHER INFORMATION: mutagenesis primer

<400> SEQUENCE: 2
catctccagc agcaggtcag agagggcac cacgttctt                    39

<210> SEQ ID NO 3
<211> LENGTH: 39
<212> TYPE: DNA
<213> ORGANISM: artificial sequence
```

```
<220> FEATURE:
<223> OTHER INFORMATION: mutagenesis primer

<400> SEQUENCE: 3
aagaacgtgg tgcccctcaa tgacctgctg ctggagatg                            39

<210> SEQ ID NO 4
<211> LENGTH: 39
<212> TYPE: DNA
<213> ORGANISM: artificial sequence
<220> FEATURE:
<223> OTHER INFORMATION: mutagenesis primer

<400> SEQUENCE: 4
catctccagc agcaggtcat tgaggggcac cacgttctt                            39

<210> SEQ ID NO 5
<211> LENGTH: 39
<212> TYPE: DNA
<213> ORGANISM: artificial sequence
<220> FEATURE:
<223> OTHER INFORMATION: mutagenesis primer

<400> SEQUENCE: 5
aagaacgtgg tgcccctctg tgacctgctg ctggagatg                            39

<210> SEQ ID NO 6
<211> LENGTH: 39
<212> TYPE: DNA
<213> ORGANISM: artificial sequence
<220> FEATURE:
<223> OTHER INFORMATION: mutagenesis primer

<400> SEQUENCE: 6
catctccagc agcaggtcac agaggggcac cacgttctt                            39

<210> SEQ ID NO 7
<211> LENGTH: 39
<212> TYPE: DNA
<213> ORGANISM: artificial sequence
<220> FEATURE:
<223> OTHER INFORMATION: mutagenesis primer

<400> SEQUENCE: 7
aacgtggtgc ccctctatgg cctgctgctg gagatgctg                            39

<210> SEQ ID NO 8
<211> LENGTH: 39
<212> TYPE: DNA
<213> ORGANISM: artificial sequence
<220> FEATURE:
<223> OTHER INFORMATION: mutagenesis primer

<400> SEQUENCE: 8
cagcatctcc agcagcaggc catagagggg caccacgtt                            39
```